(12) United States Patent
Liu et al.

(10) Patent No.: US 9,676,854 B2
(45) Date of Patent: Jun. 13, 2017

(54) ANTI-B7-H4 ANTIBODIES AND THEIR USES

(75) Inventors: Linda Liu, Clarksville, MD (US); Shannon Marshall, Baltimore, MD (US); Solomon Langermann, Baltimore, MD (US)

(73) Assignee: MedImmune, LLC, Gaithersburg, MD (US)

(*) Notice: Subject to any disclaimer, the term of this patent is extended or adjusted under 35 U.S.C. 154(b) by 466 days.

(21) Appl. No.: 14/239,117

(22) PCT Filed: Aug. 15, 2012

(86) PCT No.: PCT/US2012/050903
§ 371 (c)(1),
(2), (4) Date: Aug. 11, 2014

(87) PCT Pub. No.: WO2013/025779
PCT Pub. Date: Feb. 21, 2013

(65) Prior Publication Data
US 2014/0356364 A1    Dec. 4, 2014

Related U.S. Application Data

(60) Provisional application No. 61/523,819, filed on Aug. 15, 2011.

(51) Int. Cl.
*C07K 16/28* (2006.01)
*A61K 39/395* (2006.01)
*C07K 16/30* (2006.01)

(52) U.S. Cl.
CPC .......... *C07K 16/2827* (2013.01); *C07K 16/30* (2013.01); *C07K 2317/565* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| 6,962,980 | B2 | 11/2005 | Mitcham |
| 7,619,068 | B2 | 11/2009 | Pilkington |
| 7,622,565 | B2 | 11/2009 | Chen |
| 7,737,255 | B1 | 6/2010 | Salceda |
| 7,847,081 | B2 | 12/2010 | Chen |
| 7,875,702 | B2 | 1/2011 | Chen |
| 7,888,477 | B2 | 2/2011 | Bangur |
| 7,931,896 | B2 | 4/2011 | Chen |
| 2005/0202536 | A1 | 9/2005 | Chen |
| 2006/0003452 | A1 | 1/2006 | Humeau |
| 2007/0036783 | A1 | 2/2007 | Humeau |
| 2007/0122378 | A1 | 5/2007 | Freeman |
| 2007/0160578 | A1 | 7/2007 | Waldmann |
| 2007/0172504 | A1 | 7/2007 | Shirwan |
| 2007/0184473 | A1 | 8/2007 | Shirwan |
| 2007/0218032 | A1 | 9/2007 | Kwon |
| 2008/0050370 | A1 | 2/2008 | Glaser |
| 2008/0160036 | A1 | 7/2008 | Chen |
| 2008/0177039 | A1 | 7/2008 | Chen |
| 2008/0206235 | A1 | 8/2008 | Chen |
| 2009/0018315 | A1 | 1/2009 | Chen |
| 2009/0022747 | A1 | 1/2009 | Chen |
| 2009/0048122 | A1 | 2/2009 | Glaser |
| 2009/0087416 | A1 | 4/2009 | Chen |
| 2009/0118175 | A1 | 5/2009 | Macina |
| 2009/0136490 | A1* | 5/2009 | Pilkington ......... C07K 16/2827 424/133.1 |
| 2009/0142342 | A1 | 6/2009 | Chen |
| 2009/0176317 | A1 | 7/2009 | Kwon |
| 2009/0215084 | A1 | 8/2009 | Kwon |
| 2009/0275633 | A1 | 11/2009 | Esteller |
| 2010/0028450 | A1 | 2/2010 | Vasu |
| 2010/0092524 | A1 | 4/2010 | Taylor |
| 2010/0158936 | A1 | 6/2010 | Shirwan |
| 2010/0227335 | A1 | 9/2010 | Baker |
| 2010/0227343 | A1 | 9/2010 | Cheek |
| 2010/0240585 | A1 | 9/2010 | Shirwan |
| 2010/0256000 | A1 | 10/2010 | Ryu |
| 2011/0020325 | A1 | 1/2011 | Kwon |

(Continued)

FOREIGN PATENT DOCUMENTS

| EP | 2109455 | 10/2009 |
| EP | 2124998 | 12/2009 |

(Continued)

OTHER PUBLICATIONS

Rentero et al., Chimia 2011, 65: 843-845.*
Agarwal, et al., "The Role of Positive Costimulatory Molecules in Transplantation and Tolerance," Curr. Opin. Organ Transplant., 13:366-72 (2008).
Bignotti, et al., "Differential Gene Expression Profiles Between Tumor Biopsies and Short Term Primary Cultures of Ovarian Serous Carcinomas: Identification of Novel Molecular Biomarkers for Early Diagnosis and Therapy," Gynecol. Oncol., 103:405-16 (2006).
Brandt, et al., "The B7 family member B7-H6 is a tumor cell, ligand for the activating natural killer cell receptor NKp30 inhumans", J Exp Med., 206 (7):1495-503 (2009).

(Continued)

*Primary Examiner* — Ilia Ouspenski
(74) *Attorney, Agent, or Firm* — Melissa Hunter-Ensor; Leslie Serunian; Greenberg Traurig, LLP

(57) ABSTRACT

The present invention relates to antibodies (including anti-B7-H4 antibodies) and their antigen-binding fragments and to other molecules (including fusion proteins that bind to the cognate antigen/receptor, etc.) that are capable of immunospecifically binding to B7-H4 and the uses of such molecules in the diagnosis and the treatment of cancer and other diseases. The invention particularly concerns the use of such molecules to retard or prevent tumor growth, inhibit tumor-mediated suppression, eliminate tumors and/or deplete or block the activity of tumor associated macrophages ("TAMs") so as to alter their activity and/or decrease TAM—mediated immune suppression.

24 Claims, 11 Drawing Sheets

(56) References Cited

U.S. PATENT DOCUMENTS

2011/0085970 A1 4/2011 Terrett
2015/0315275 A1* 11/2015 Langermann ...... C07K 16/2827
424/133.1

FOREIGN PATENT DOCUMENTS

| WO | 2006007539 | 1/2006 |
|---|---|---|
| WO | 2006066229 | 6/2006 |
| WO | 2006121991 | 11/2006 |
| WO | 2006133396 | 12/2006 |
| WO | 2006138670 | 12/2006 |
| WO | 2007041694 | 4/2007 |
| WO | 2007067681 | 6/2007 |
| WO | 2007067682 | 6/2007 |
| WO | 2007082154 | 7/2007 |
| WO | 2007087341 | 8/2007 |
| WO | 2007109254 | 9/2007 |
| WO | 2007122369 | 11/2007 |
| WO | 2007124361 | 11/2007 |
| WO | 2008083228 | 7/2008 |
| WO | 2008083239 | 7/2008 |
| WO | 2008092153 | 7/2008 |
| WO | 2009073533 | 6/2009 |
| WO | 2009111315 | 9/2009 |
| WO | 2010102167 | 9/2010 |
| WO | 2010102177 | 9/2010 |

OTHER PUBLICATIONS

Carter, et al., "Cell Biology of HIV-1 Infection of Macrophages," Ann. Rev. Microbiol., 62:425-43 (2008).
Choi, et al., "Genomic Organization and Expression, Analysis of B7-H4, an Immune Inhibitory Molecule of the B7 Family," J. Immunol., 171:4650-4654 (2003).
Collins, et al., "The B7 Family of Immune-Regulatory Ligands," Genome Biol., 6:223,1-223.7 (2005).
Coyle, et al., "The Expanding B7 Superfamily: Increasing Complexity in Costimulatory Signals Regulating T Cell Function," Nature Immunol., 2(3):203-9 (2001).
Dave, et al., "Prediction of Survival in Follicular Lymphoma Based on Molecular Features of Tumor-Infiltrating Immune Cells," N. Engl. J. Med., 351:2159-69 (2004).
Dong, et al., "Immune Regulation by Novel Costimulatory Molecules," Immunolog. Res., 28(1):39-48 (2003).
Farinha, et al., "Analysis of Multiple Biomarkers Shows That Lymphoma-Associated Macrophage (LAM) Content Is an Independent Predictor of Survival in Follicular Lymphoma (FL)," Blood, 106:2169-74 (2005).
Flies, et al., "The New B7s: Playing a Pivotal Role in Tumor Immunity," J. Immunother., 30(3):251-60 (2007).
Greenwald, et al., "The B7 Family Revisited," Ann. Rev. Immunol., 23:515-48 (2005).
Gross, et al., "Identification and Distribution of the Costimulatory Receptor CD28 in the Mouse," J. Immunol., 149:380-8 (1992).
Korman, et al., "Checkpoint Blockade in Cancer Immunotherapy," Adv. Immunol., 90:297-339 (2007).
Krambeck, et al., "B7-H4 Expression in Renal Cell Carcinoma and Tumor Vasculature: Associations With Cancer Progression and Survival," PNAS, 103:10391-6 (2006).
Kryczek, et al., "B7-H4 Expression Identifies a Novel Suppressive Macrophage Population in Human Ovarian Carcinoma," J. Exp. Med., 203(4):871-881 (2006a).
Kryczek, et al., "Cutting Edge: Induction of B7-H4 on APCs Through IL-10: Novel Suppressive Mode for Regulatory T Cells," J. Immunol., 177(1):40-4 (2006b).
Kryczek, et al., "Relationship Between B7-H4, Regulatory T Cells, and Patient Outcome in Human Ovarian Carcinoma," Cancer Res., 67(18):8900-5 (2007).
Lenschow, et al., "CD28/B7 System of T Cell Costimulation," Ann. Rev. Immunol., 14:233-58 (1996).

Lepenies, et al., "The Role of Negative Costimulators During Parasitic Infections," Endocrine, Metabolic & Immune Disorders—Drug Targets, 8:279-88 (2008).
Lin, et al., "Clinical Significance of Tumor-Associated Macrophage Infiltration in Supraglottic Laryngeal Carcinoma," Chin. J. Cancer, 30(4):280-6 (2011).
Lindley, et al., "The Clinical Utility of Inhibiting CD28-Mediated Costimulation," Immunol. Rev., 229:307-21(2009).
Linsley, et al., "Intracellular Trafficking of CTLA4 and Focal Localization Towards Sites of TCR Engagement," Immunity., 4:535-43 (1996).
Liu, et al., "Tumor-Associated Macrophages Recruit CCR6+ Regulatory T Cells. And Promote the Development of Colorectal Cancer Via Enhancing CCL20 Production in Mice," PLoS One, 6(4):e19495 (2011).
Loke, et al., "Emerging Mechanisms of Immune Regulation: The Extended B7 Family and Regulatory T Cells." Arthritis Res. Ther., 6:208-14 (2004).
Noursadeghi, et al., "HIV-1 Infection of Mononuclear Phagocytic Cells: The Case for Bacterial Innate Immune Deficiency in AIDS," Lancet Infect. Dis., 6:794-804 (2006).
Nucera, et al., "The Interplay Between Macrophages and Angiogenesis in Development, Tissue Injury and Regeneration," Int. J. Dev. Biol., doi: 10.1387/ ijdb.103227sn (2011).
Pollard, "Trophic Macrophages in Development and Disease," Nat. Rev. Immunol., 9:259-70 (2009).
Prasad, et al., "B7S1, A Novel B7 Family Member That Negatively Regulates T Cell Activation," Immunity, 18:863-73 (2003).
Rigo, et al.,"Macrophages May Promote Cancer Growth Via a GM-CSF/HB-EGF Paracrine Loop That Is Enhanced by CXCL12," Molec. Cancer, 9(273):1-13 (2010).
Salceda, et al., "The Immunomodulatory Protein B7-H4 Is Overexpressed in Breast and Ovarian Cancers and Promotes Epithelial Cell Transformation," Exp. Cell Res., 306:128-41 (2005).
Schwartz, et al.,"Structural Basis for Co-Stimulation by the Human CTLA-4/ B7-2 Complex," Nature, 410:604-8 (2001).
Sharpe, et al., "The B7-CD28 Superfamily," Nature Rev. Immunol., 2:116-26 (2002).
Sica, et al., "B7-H4, A Molecule of the B7 Family, Negatively Regulates T Cell Immunity," Immunity, 18:849-61 (2003).
Simon, et al.,"B7-h4 Is a Novel Membrane-Bound Protein and a Candidate Serum and Tissue Biomarker for Ovarian Cancer," Cancer Res., 66:1570-5 (2006).
Solinas, et al., "Tumor-Associated Macrophages (TAM) As Major Players of the Cancer-Related Inflammation," J. Leukoc. Biol., 86(5):1065-73 (2009).
Stamper, et al., "Crystal Structure of the B7-1/CTLA-4 Complex That Inhibits Human Immune Responses," Nature, 410: 608-11 (2001).
Sun, et al., "B7-H3 and B7-H4 Expression in Non-Small-Cell Lung Cancer," Lung Cancer, 53:143-51 (2006).
Tringler, et al., "B7-H4 Is Highly Expressed in Ductal and Lobular Breast Cancer," Clin. Cancer Res., 11:1842-8 (2005).
Tringler, et al., "B7-H4 Overexpression in Ovarian Tumors," Gynecol. Oncol., 100 100:44-52 (2006).
Vergati, "The Consequence of Immune Suppressive Cells in the Use of Therapeutic Cancer Vaccines and Their Importance in Immune Monitoring," J. Biomed. Biotechnol., 182413 (2011).
Viglietta, et al., "Modulating Co-Stimulation," Neurotherapeutics, 4:666-75 (2007).
Wang, et al., "Co-Signaling Molecules of The B7-CD28 Family in Positive and Negative Regulation of T Lymphocyte Responses," Microbes Infect., 6:759-66 (2004).
Wang, et al., "VISTA, A Novel Mouse Ig Superfamily Ligand That Negatively Regulates T Cell Responses," J. Exp. Med., 10.1084/jem.20100619:1-16 (2011).
Wei, et al., "Tissue-Specific Expression of B7x Protects From CD4 T Cell-Mediated Autoimmunity," J. Exper. Med., 208(8):1683-94 (2011).
Zamarron, et al., "Dual Roles of Immune Cells and Their Factors in Cancer Development and Progression," Int. J. Biol. Sci., 7(5):651-8 (2011).

(56) References Cited

OTHER PUBLICATIONS

Zang, et al., "B7x: A Widely Expressed B7 Family Member That Inhibits T Cell Activation," PNAS, 100:10388-92 (2003).
Zhu, et al.,"B7-H4 Deficient Mice Display Augmented Neutrophil-Mediated Innate Immunity," Blood, 113:1759-69 (2009).
Qian, Y. et al., Jul. 2011, "Development of a Novel Monoclonal Antibody to B7-H4: Characterization and Biological Activity", European Journal of Medical Research, vol. 16, pp. 295-302.
Terrett, J. et al. "Preclinical development of anti B7-H4 therapeutic antibodies", Cancer Research, May 1, 2008, Retrieved from Internet URL: http://cancerres.aacrjournals.org/content/68/9_Supplement/4986, 3 pages.

* cited by examiner

SEQUENCE LISTING

```
<160> NUMBER OF SEQ ID NOS: 50

<210> SEQ ID NO 1
<211> LENGTH: 282
<212> TYPE: PRT
<213> ORGANISM: Homo sapiens

<400> SEQUENCE: 1

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Lys His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 2
```

-continued

```
<211> LENGTH: 283
<212> TYPE: PRT
<213> ORGANISM: Mus musculus

<400> SEQUENCE: 2

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
                20                  25                  30

Gly Lys His Phe Ile Thr Val Thr Phe Thr Ser Ala Gly Asn Ile
            35                  40                  45

Gly Glu Asp Gly Thr Leu Ser Cys Thr Phe Glu Pro Asp Ile Lys Leu
        50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
        275                 280

<210> SEQ ID NO 3
<211> LENGTH: 112
<212> TYPE: PRT
<213> ORGANISM: Mus musculus

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser His Ser Leu Val His Ser
                20                  25                  30

Asn Gly Asn Thr Tyr Leu His Trp Tyr Leu Gln Lys Pro Gly Gln Ser
            35                  40                  45

Pro Asn Leu Leu Ile Tyr Ile Val Ser Asn Arg Phe Ser Gly Val Pro
        50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
                100                 105                 110

<210> SEQ ID NO 4
<211> LENGTH: 116
<212> TYPE: PRT
<213> ORGANISM: Mus musculus

<400> SEQUENCE: 4

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser His
                20                  25                  30

Gly Met Ser Trp Val Arg Gln Thr Pro Glu Lys Arg Leu Asp Trp Val
            35                  40                  45

Ala Thr Ile Ser Asp Gly Gly Thr Tyr Thr Tyr Tyr Pro Val Asn Val
        50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Gly Gly Gly Ala Tyr Trp Gly Gln Gly Thr Leu Val
                100                 105                 110

Thr Val Ser Ala
        115

<210> SEQ ID NO 5
<211> LENGTH: 113
<212> TYPE: PRT
<213> ORGANISM: Mus musculus

<400> SEQUENCE: 5

Asp Ile Val Met Ser Gln Ser Pro Ser Ser Leu Ala Val Ser Val Gly
1               5                   10                  15

Glu Lys Val Thr Val Ser Cys Lys Ser Ser Gln Ser Leu Leu Tyr Ser
                20                  25                  30

Thr Asn Gln Arg Thr Tyr Leu Ala Trp Phe Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Thr Gly Thr Lys Leu Glu Leu
                100                 105                 110

Lys

<210> SEQ ID NO 6
<211> LENGTH: 115
<212> TYPE: PRT
<213> ORGANISM: Mus musculus -continued

```
<400> SEQUENCE: 6

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Lys Phe Thr Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Ser Thr Tyr Tyr Leu Asp Ser Leu
        50                  55                  60

Lys Ser Arg Phe Ile Ile Ser Arg Asp Asn Ala Lys Asn Ile Leu Tyr
65                  70                  75                  80

Leu Gln Met Asn Ser Leu Lys Ser Glu Asp Thr Ala Thr Tyr Tyr Cys
                85                  90                  95

Ala Arg Lys Gly Tyr Phe Asp Tyr Trp Gly Gln Gly Thr Thr Leu Thr
            100                 105                 110

Val Ser Ser
        115

<210> SEQ ID NO 7
<211> LENGTH: 110
<212> TYPE: PRT
<213> ORGANISM: Mus musculus

<400> SEQUENCE: 7

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Ile Asp Asn Tyr
                20                  25                  30

Gly Ile Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Phe Cys Gln Gln Ser Asp
                85                  90                  95

Glu Gly Arg Thr Phe Gly Gly Gly Thr Lys Leu Glu Ile Lys
            100                 105                 110

<210> SEQ ID NO 8
<211> LENGTH: 118
<212> TYPE: PRT
<213> ORGANISM: Mus musculus

<400> SEQUENCE: 8

Glu Val Gln Leu Val Glu Ser Gly Gly Asn Leu Val Lys Pro Gly Gly
1               5                   10                  15

Ser Leu Lys Leu Ser Cys Ala Ala Ser Gly Phe Thr Phe Ser Asn Ser
                20                  25                  30

Ala Met Ser Trp Val Arg Gln Thr Pro Glu Lys Arg Leu Glu Trp Val
            35                  40                  45

Ala Thr Ile Ser Asp Gly Gly Arg Tyr Thr Tyr Tyr Pro Asp Asn Val
        50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Leu Tyr Tyr Cys
```

```
                    85                  90                  95
Ala Arg Asp Arg Pro His Trp Tyr Phe Asp Val Trp Gly Thr Gly Ala
            100                 105                 110

Thr Val Thr Val Ser Ser
        115

<210> SEQ ID NO 9
<211> LENGTH: 16
<212> TYPE: PRT
<213> ORGANISM: Mus musculus

<400> SEQUENCE: 9

Arg Ser Ser His Ser Leu Val His Ser Asn Gly Asn Thr Tyr Leu His
1               5                   10                  15

<210> SEQ ID NO 10
<211> LENGTH: 17
<212> TYPE: PRT
<213> ORGANISM: Mus musculus

<400> SEQUENCE: 10

Lys Ser Ser Gln Ser Leu Leu Tyr Ser Thr Asn Gln Arg Thr Tyr Leu
1               5                   10                  15

Ala

<210> SEQ ID NO 11
<211> LENGTH: 15
<212> TYPE: PRT
<213> ORGANISM: Mus musculus

<400> SEQUENCE: 11

Arg Ala Ser Glu Ser Ile Asp Asn Tyr Gly Ile Ser Phe Met His
1               5                   10                  15

<210> SEQ ID NO 12
<211> LENGTH: 17
<212> TYPE: PRT
<213> ORGANISM: Artificial Sequence
<220> FEATURE:
<223> OTHER INFORMATION: Consensus Light Chain CDR1 of Anti-Human B7-H4
      Antibody
<220> FEATURE:
<221> NAME/KEY: MISC_FEATURE
<222> LOCATION: (1)..(1)
<223> OTHER INFORMATION: R or K
<220> FEATURE:
<221> NAME/KEY: MISC_FEATURE
<222> LOCATION: (2)..(2)
<223> OTHER INFORMATION: S or A
<220> FEATURE:
<221> NAME/KEY: MISC_FEATURE
<222> LOCATION: (4)..(4)
<223> OTHER INFORMATION: R, N, Q, E or H
<220> FEATURE:
<221> NAME/KEY: MISC_FEATURE
<222> LOCATION: (6)..(6)
<223> OTHER INFORMATION: L or I
<220> FEATURE:
<221> NAME/KEY: MISC_FEATURE
<222> LOCATION: (7)..(7)
<223> OTHER INFORMATION: Any amino acid
<220> FEATURE:
<221> NAME/KEY: MISC_FEATURE
<222> LOCATION: (8)..(8)
<223> OTHER INFORMATION: A, R, N, Q, E, H, K, M, S, T or Y
<220> FEATURE:
<221> NAME/KEY: MISC_FEATURE
<222> LOCATION: (9)..(9)
<223> OTHER INFORMATION: Absent or S
```

```
<220> FEATURE:
<221> NAME/KEY: MISC_FEATURE
<222> LOCATION: (10)..(10)
<223> OTHER INFORMATION: Absent or T
<220> FEATURE:
<221> NAME/KEY: MISC_FEATURE
<222> LOCATION: (11)..(11)
<223> OTHER INFORMATION: A, R, N, Q, E, H, K, M, S, T, or Y
<220> FEATURE:
<221> NAME/KEY: MISC_FEATURE
<222> LOCATION: (12)..(12)
<223> OTHER INFORMATION: A, R, N, D, Q, E, G, H, K, P, S, T, or W
<220> FEATURE:
<221> NAME/KEY: MISC_FEATURE
<222> LOCATION: (13)..(13)
<223> OTHER INFORMATION: A, R, N, D, C, Q, E, H, I, L, K, M, F, P, S, T,
     Y, or W
<220> FEATURE:
<221> NAME/KEY: MISC_FEATURE
<222> LOCATION: (14)..(14)
<223> OTHER INFORMATION: S or T
<220> FEATURE:
<221> NAME/KEY: MISC_FEATURE
<222> LOCATION: (15)..(15)
<223> OTHER INFORMATION: F or Y
<220> FEATURE:
<221> NAME/KEY: MISC_FEATURE
<222> LOCATION: (16)..(16)
<223> OTHER INFORMATION: L or M
<220> FEATURE:
<221> NAME/KEY: MISC_FEATURE
<222> LOCATION: (17)..(17)
<223> OTHER INFORMATION: A, R, N, D, Q, E, G, H, K, M, F, P, S, T, W or
     Y

<400> SEQUENCE: 12

Xaa Xaa Ser Xaa Ser Xaa Xaa Xaa Xaa Xaa Xaa Xaa Xaa Xaa Xaa Xaa
1               5                   10                  15

Xaa

<210> SEQ ID NO 13
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light chain CDR2 of Anti-Human B7-H4 Antibody
     2D1

<400> SEQUENCE: 13

Ile Val Ser Asn Arg Phe Ser
1               5

<210> SEQ ID NO 14
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light chain CDR2 of Anti-Human B7-H4 Antibody
     2E11

<400> SEQUENCE: 14

Trp Ala Ser Thr Arg Glu Ser
1               5

<210> SEQ ID NO 15
<211> LENGTH: 7
<212> TYPE: PRT
<213> ORGANISM: Mus musculus
```

```
<220> FEATURE:
<221> NAME/KEY: MISC_FEATURE
<222> LOCATION: (1)..(7)
<223> OTHER INFORMATION: Light chain CDR2 of Anti-Human B7-H4 Antibody
      2H9

<400> SEQUENCE: 15

Arg Ala Ser Asn Leu Glu Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Consensus Light Chain CDR2 of Anti-Human B7-H4
      Antibody
<220> FEATURE:
<221> NAME/KEY: MISC_FEATURE
<222> LOCATION: (1)..(1)
<223> OTHER INFORMATION: A, R, C, Q, E, H, I, L, K, M, F, S, T, W, Y, or
      V
<220> FEATURE:
<221> NAME/KEY: MISC_FEATURE
<222> LOCATION: (2)..(2)
<223> OTHER INFORMATION: A or V
<220> FEATURE:
<221> NAME/KEY: MISC_FEATURE
<222> LOCATION: (4)..(4)
<223> OTHER INFORMATION: N, S, or T
<220> FEATURE:
<221> NAME/KEY: MISC_FEATURE
<222> LOCATION: (5)..(5)
<223> OTHER INFORMATION: A, R, Q, L, K, M, S, T, or Y
<220> FEATURE:
<221> NAME/KEY: MISC_FEATURE
<222> LOCATION: (6)..(6)
<223> OTHER INFORMATION: A, R, N, D, Q, E, G, H, I, L, K, M, F, S, T, W,
      Y, or V

<400> SEQUENCE: 16

Xaa Xaa Ser Xaa Xaa Xaa Ser
1               5

<210> SEQ ID NO 17
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CD3 of Anti-Human B7-H4 Antibody
      2D1
<220> FEATURE:
<221> NAME/KEY: MISC_FEATURE
<222> LOCATION: (1)..(9)
<223> OTHER INFORMATION: Light Chain CDR3 of Anti-Human B7-H4 Antibody
      2D1

<400> SEQUENCE: 17

Ser Gln Ser Thr His Val Pro Pro Thr
1               5

<210> SEQ ID NO 18
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CD3 of Anti-Human B7-H4 Antibody
      2E11
<220> FEATURE:
```

```
<221> NAME/KEY: MISC_FEATURE
<222> LOCATION: (1)..(9)
<223> OTHER INFORMATION: Light Chain CDR3 of Anti-Human B7-H4 Antibody
      2E11

<400> SEQUENCE: 18

Gln Gln Tyr Tyr Asn Tyr Pro Leu Thr
1               5

<210> SEQ ID NO 19
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Light Chain CDR3 of Anti-Human B7-H4 Antibody
      2H9

<400> SEQUENCE: 19

Gln Gln Ser Asp Glu Gly Arg Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Consensus Light Chain CDR3 of Anti-Human B7-H4
      Antibody
<220> FEATURE:
<221> NAME/KEY: MISC_FEATURE
<222> LOCATION: (1)..(1)
<223> OTHER INFORMATION: N, D, Q, E, K, or S
<220> FEATURE:
<221> NAME/KEY: MISC_FEATURE
<222> LOCATION: (3)..(3)
<223> OTHER INFORMATION: A, R, N, C, Q, E, H, I, L, M, F, S, T, Y, or V
<220> FEATURE:
<221> NAME/KEY: MISC_FEATURE
<222> LOCATION: (3)..(3)
<223> OTHER INFORMATION: A, R, N, C, Q, E, H, I, L, M, F, S, T, Y, or V
<220> FEATURE:
<221> NAME/KEY: MISC_FEATURE
<222> LOCATION: (4)..(4)
<223> OTHER INFORMATION: A, R, N, D, C, Q, E, G, H, I, K, M, F, P, S, T,
      Y, or V
<220> FEATURE:
<221> NAME/KEY: MISC_FEATURE
<222> LOCATION: (5)..(5)
<223> OTHER INFORMATION: R, N, Q, E, or H
<220> FEATURE:
<221> NAME/KEY: MISC_FEATURE
<222> LOCATION: (6)..(6)
<223> OTHER INFORMATION: A, R, N, D, C, Q, E, G, H, K, M, F, P, S, T, W,
      Y, or V
<220> FEATURE:
<221> NAME/KEY: MISC_FEATURE
<222> LOCATION: (7)..(7)
<223> OTHER INFORMATION: Absent or P
<220> FEATURE:
<221> NAME/KEY: MISC_FEATURE
<222> LOCATION: (8)..(8)
<223> OTHER INFORMATION: A, R, N, D, C, Q, E, H, I, L, K, M, P, S, T, Y,
      or V

<400> SEQUENCE: 20

Xaa Gln Xaa Xaa Xaa Xaa Xaa Xaa Thr
1               5

<210> SEQ ID NO 21
<211> LENGTH: 10
<212> TYPE: PRT
```

```
<213> ORGANISM: Mus musculus
<220> FEATURE:
<221> NAME/KEY: MISC_FEATURE
<222> LOCATION: (1)..(10)
<223> OTHER INFORMATION: Heavy Chain CDR1 of Anti-Human B7-H4 Antibody
      2D1

<400> SEQUENCE: 21

Gly Phe Thr Phe Asn Ser His Gly Met Ser
1               5                   10

<210> SEQ ID NO 22
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Heavy Chain CDR1 of Anti-Human B7-H4 Antibody
      2E11

<400> SEQUENCE: 22

Gly Phe Lys Phe Thr Asp Tyr Tyr Met Ala
1               5                   10

<210> SEQ ID NO 23
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Heavy Chain CDR1 of Anti-Human B7-H4 Antibody
      2H9

<400> SEQUENCE: 23

Gly Phe Thr Phe Ser Asn Ser Ala Met Ser
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Consensus Heavy Chain CDR1 of Anti-Human B7-H4
      Antibody
<220> FEATURE:
<221> NAME/KEY: MISC_FEATURE
<222> LOCATION: (3)..(3)
<223> OTHER INFORMATION: A, R, N, D, Q, E, K, M, P, S, or T
<220> FEATURE:
<221> NAME/KEY: MISC_FEATURE
<222> LOCATION: (5)..(5)
<223> OTHER INFORMATION: N, S, or T
<220> FEATURE:
<221> NAME/KEY: MISC_FEATURE
<222> LOCATION: (6)..(6)
<223> OTHER INFORMATION: N, D, H, or S
<220> FEATURE:
<221> NAME/KEY: MISC_FEATURE
<222> LOCATION: (7)..(7)
<223> OTHER INFORMATION: A, R, N, Q, E, H, K, M, F, S, T, or Y
<220> FEATURE:
<221> NAME/KEY: MISC_FEATURE
<222> LOCATION: (8)..(8)
<223> OTHER INFORMATION: A, R, N, D, C, Q, E, G, H, K, M, F, P, S, T, W,
      Y, or V
<220> FEATURE:
<221> NAME/KEY: MISC_FEATURE
<222> LOCATION: (10)..(10)
<223> OTHER INFORMATION: S or A

<400> SEQUENCE: 24
```

Gly Phe Xaa Phe Xaa Xaa Xaa Xaa Met Xaa
1               5                   10

<210> SEQ ID NO 25
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Heavy Chain CDR2 of Anti-Human B7-H4 Antibody
      2D1

<400> SEQUENCE: 25

Thr Ile Ser Asp Gly Gly Thr Tyr Thr Tyr Tyr Pro Val Asn Val Lys
1               5                   10                  15

Gly

<210> SEQ ID NO 26
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Heavy Chain CDR2 of Anti-Human B7-H4 Antibody
      2E11

<400> SEQUENCE: 26

Asn Ile Asn Tyr Asp Gly Ser Ser Thr Tyr Tyr Leu Asp Ser Leu Lys
1               5                   10                  15

Ser

<210> SEQ ID NO 27
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Heavy Chain CDR2 of Anti-Human B7-H4 Antibody
      2H9

<400> SEQUENCE: 27

Thr Ile Ser Asp Gly Gly Arg Tyr Thr Tyr Tyr Pro Asp Asn Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Consensus Heavy Chain CDR2 of Anti-Human B7-H4
      Antibody
<220> FEATURE:
<221> NAME/KEY: MISC_FEATURE
<222> LOCATION: (1)..(1)
<223> OTHER INFORMATION: N, S, or T
<220> FEATURE:
<221> NAME/KEY: MISC_FEATURE
<222> LOCATION: (3)..(3)
<223> OTHER INFORMATION: N or S
<220> FEATURE:
<221> NAME/KEY: MISC_FEATURE
<222> LOCATION: (4)..(4)
<223> OTHER INFORMATION: A, R, N, D, C, Q, E, G, H, I, L, K, M, F, P, S,
      T, Y, or V -continued

```
<220> FEATURE:
<221> NAME/KEY: MISC_FEATURE
<222> LOCATION: (5)..(5)
<223> OTHER INFORMATION: N, D, G, or S
<220> FEATURE:
<221> NAME/KEY: MISC_FEATURE
<222> LOCATION: (7)..(7)
<223> OTHER INFORMATION: A, R, N, Q, E, K, M, S, or T
<220> FEATURE:
<221> NAME/KEY: MISC_FEATURE
<222> LOCATION: (8)..(8)
<223> OTHER INFORMATION: A, R, N, C, Q, E, H, I, L, K, M, F, S, T, Y,
      or V
<220> FEATURE:
<221> NAME/KEY: MISC_FEATURE
<222> LOCATION: (12)..(12)
<223> OTHER INFORMATION: A, R, N, C, Q, E, H, I, L, K, M, P, S, T, Y,
      or V
<220> FEATURE:
<221> NAME/KEY: MISC_FEATURE
<222> LOCATION: (13)..(13)
<223> OTHER INFORMATION: A, R, N, D, C, Q, E, G, H, I, K, M, F, P, S,
      T, Y, or V
<220> FEATURE:
<221> NAME/KEY: MISC_FEATURE
<222> LOCATION: (14)..(14)
<223> OTHER INFORMATION: S or N
<220> FEATURE:
<221> NAME/KEY: MISC_FEATURE
<222> LOCATION: (15)..(15)
<223> OTHER INFORMATION: I, L, M, or V
<220> FEATURE:
<221> NAME/KEY: MISC_FEATURE
<222> LOCATION: (17)..(17)
<223> OTHER INFORMATION: A, N, G, or S

<400> SEQUENCE: 28

Xaa Ile Xaa Xaa Xaa Gly Xaa Xaa Thr Tyr Tyr Xaa Xaa Xaa Xaa Lys
1               5                   10                  15

Xaa

<210> SEQ ID NO 29
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Heavy Chain CDR3 of Anti-Human B7-H4 Antibody
      2D1

<400> SEQUENCE: 29

Asp Gly Gly Gly Gly Ala Tyr
1               5

<210> SEQ ID NO 30
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Heavy Chain CDR3 of Anti-Human B7-H4 Antibody
      2E11

<400> SEQUENCE: 30

Lys Gly Tyr Phe Asp Tyr
1               5

<210> SEQ ID NO 31
<211> LENGTH: 9
<212> TYPE: PRT
```

```
<213> ORGANISM: Mus musculus
<220> FEATURE:
<221> NAME/KEY: MISC_FEATURE
<222> LOCATION: (1)..(9)
<223> OTHER INFORMATION: Heavy Chain CDR3 of Anti-Human B7-H4 Antibody
      2H9

<400> SEQUENCE: 31

Asp Arg Pro His Trp Tyr Phe Asp Val
1               5

<210> SEQ ID NO 32
<211> LENGTH: 9
<212> TYPE: PRT
<213> ORGANISM: Artificial Sequence
<220> FEATURE:
<223> OTHER INFORMATION: Consensus Heavy Chain CDR3 of Anti-Human B7-H4
      Antibody
<220> FEATURE:
<221> NAME/KEY: MISC_FEATURE
<222> LOCATION: (1)..(1)
<223> OTHER INFORMATION: N, D, Q, E, H, K, P, S, or T
<220> FEATURE:
<221> NAME/KEY: MISC_FEATURE
<222> LOCATION: (2)..(2)
<223> OTHER INFORMATION: A, R, N, D, Q, E, G, H, K, P, S, or T
<220> FEATURE:
<221> NAME/KEY: MISC_FEATURE
<222> LOCATION: (3)..(3)
<223> OTHER INFORMATION: A, R, N, D, C, Q, E, G, H, K, M, P, S, T, Y, or
      V
<220> FEATURE:
<221> NAME/KEY: MISC_FEATURE
<222> LOCATION: (4)..(4)
<223> OTHER INFORMATION: A, R, N, D, C, Q, E, G, H, K, M, F, P, S, T, W,
      Y or V
<220> FEATURE:
<221> NAME/KEY: MISC_FEATURE
<222> LOCATION: (5)..(5)
<223> OTHER INFORMATION: N, D, Q, E, H, K, P, S, or T
<220> FEATURE:
<221> NAME/KEY: MISC_FEATURE
<222> LOCATION: (6)..(6)
<223> OTHER INFORMATION: Absent or Y
<220> FEATURE:
<221> NAME/KEY: MISC_FEATURE
<222> LOCATION: (7)..(7)
<223> OTHER INFORMATION: Absent or F
<220> FEATURE:
<221> NAME/KEY: MISC_FEATURE
<222> LOCATION: (8)..(8)
<223> OTHER INFORMATION: A, R, N, D, Q, E, G, H, K, P, S, or T
<220> FEATURE:
<221> NAME/KEY: MISC_FEATURE
<222> LOCATION: (9)..(9)
<223> OTHER INFORMATION: I, L, M, F, Y, or V

<400> SEQUENCE: 32

Xaa Xaa Xaa Xaa Xaa Xaa Xaa Xaa Xaa
1               5

<210> SEQ ID NO 33
<211> LENGTH: 657
<212> TYPE: DNA
<213> ORGANISM: Artificial Sequence
<220> FEATURE:
<223> OTHER INFORMATION: Nucleotide Sequence Encoding Chimeric Human
      IgG4 Light Chain of Anti-B7-H4 Antibody 2D1

<400> SEQUENCE: 33
gatgttgtga tgacccaaac tccactctcc ctgcctgtca gtcttggaga tcaagcctcc      60
atctcttgca gatctagtca cagccttgta cacagtaatg gaaacaccta tttacattgg     120
```

| | | |
|---|---|---|
| tacctgcaga agccaggcca gtctccaaac ctcctgatct acatagtttc caaccgattt | 180 | |
| tctggggtcc cagacaggtt cagtggcagt ggatcaggga cagatttcac actcaagatc | 240 | |
| agcagagtgg aggctgagga tctgggagtt tatttctgct ctcaaagtac acatgttcct | 300 | |
| cccacgttcg gtgctgggac caagctggag ctgaagcgga ccgtggccgc cccagcgtg | 360 | |
| ttcatcttcc ctcccagcga cgagcagctg aagtctggca ccgccagcgt ggtgtgcctg | 420 | |
| ctgaacaact ctaccccccg cgaggccaag gtgcagtgga aggtggacaa cgccctgcag | 480 | |
| agcggcaaca gccaggagag cgtgaccgag caggactcca aggacagcac ctacagcctg | 540 | |
| agcagcaccc tgaccctgag caaggccgac tacgagaagc acaaggtgta cgcctgcgag | 600 | |
| gtgacccacc agggactgtc tagccccgtg accaagagct caaccggggg cgagtgc | 657 | |

```
<210> SEQ ID NO 34
<211> LENGTH: 219
<212> TYPE: PRT
<213> ORGANISM: Artificial Sequence
<220> FEATURE:
<223> OTHER INFORMATION: Amino Acid Sequence of Chimeric Human IgG4
      Light Chain of Anti-B78-H4 Antibody 2D1
<220> FEATURE:
<221> NAME/KEY: MISC_FEATURE
<222> LOCATION: (1)..(112)
<223> OTHER INFORMATION: Variable Domain

<400> SEQUENCE: 34

Asp Val Val Met Thr Gln Thr Pro Leu Ser Leu Pro Val Ser Leu Gly
1               5                   10                  15

Asp Gln Ala Ser Ile Ser Cys Arg Ser Ser His Ser Leu Val His Ser
            20                  25                  30

Asn Gly Asn Thr Tyr Leu His Trp Tyr Leu Gln Lys Pro Gly Gln Ser
        35                  40                  45

Pro Asn Leu Leu Ile Tyr Ile Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 1329
<212> TYPE: DNA
```

<213> ORGANISM: Artificial Sequence
<220> FEATURE:
<223> OTHER INFORMATION: Nucleotide Sequence Encoding Chimeric Human
      IgG4 Heavy Chain of Anti-B7-H4 Antibody 2D1

<400> SEQUENCE: 35

```
gaagtgcagc tggtggagtc tgggggaggc ttagtgaagc ctggagggtc cctgaaactc      60
tcctgtgcag cctctggatt cactttcaat agccatggca tgtcttgggt tcgccagact     120
ccggaaaaga ggctggactg ggtcgcaacc attagtgatg gtggtactta cacctactat     180
ccagtcaatg taaagggccg attcaccatc tccagagaca atgccaagaa caacctgtac     240
ctgcaaatga gccatctgaa gtccgaggac acagccatgt attactgtgc aagagatggg     300
ggggagggg cttactgggg ccaagggact ctggtcactg tctctgcagc tagcaccaag     360
ggtccatcgg tcttcccact ggcgccttgc tccaggagca cctccgagag cacagccgct     420
ctgggttgcc tggtcaagga ctacttcccc gaaccggtga cggtgtcgtg aactcaggt     480
gccctgacca gcggcgtgca ccttcccg gctgtcctac agtcctcagg actctactcc      540
ctcagcagcg tggtgaccgt gccctccagc agcttgggta cgaagaccta cacctgcaac     600
gtagatcaca agcccagcaa caccaaggtg gacaagagag ttgagtccaa atatggtcct     660
ccatgcccac catgcccagc acctgagttc ctggggtgga catcagtctt cctgttccca     720
ccaaaaccca aggacactct catgatctcc cggacccctg aggtcacgtg cgtcgtagtt     780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca agccaaagg gcagccacga    1020
gagccacagg tgtacaccct gcctccatcc caggaagaga tgaccaagaa ccaggtcagc    1080
ctgacctgcc tggtcaaagg cttctaccct agcgacatcg ccgtggagtg ggagagcaat    1140
gggcagccgg agaacaacta caagaccacg cctccagtgc tggactccga cggctccttc    1200
ttcctctaca gcaggctcac cgtggacaag agcaggtggc aggagggtaa tgtcttctca    1260
tgctccgtga tgcatgaggc tctgcacaac cactacacac agaagagcct gagcctgagc    1320
cccggaaag                                                              1329
```

<210> SEQ ID NO 36
<211> LENGTH: 443
<212> TYPE: PRT
<213> ORGANISM: Artificial Sequence
<220> FEATURE:
<223> OTHER INFORMATION: Amino Acid Sequence of Chimeric Human IgG4
      Heavy Chain of Anti-B7-H4 Antibody 2D1
<220> FEATURE:
<221> NAME/KEY: MISC_FEATURE
<222> LOCATION: (1)..(116)
<223> OTHER INFORMATION: Variable Domain

<400> SEQUENCE: 36

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser His
            20                  25                  30

Gly Met Ser Trp Val Arg Gln Thr Pro Glu Lys Arg Leu Asp Trp Val
        35                  40                  45

Ala Thr Ile Ser Asp Gly Gly Thr Tyr Thr Tyr Tyr Pro Val Asn Val
    50                  55                  60
```

Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Met Tyr Tyr Cys
             85                  90                  95

Ala Arg Asp Gly Gly Gly Ala Tyr Trp Gly Gln Gly Thr Leu Val
         100                 105                 110

Thr Val Ser Ala Ala Ser Thr Lys Gly Pro Ser Val Phe Pro Leu Ala
         115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 37
<211> LENGTH: 651
<212> TYPE: DNA
<213> ORGANISM: Artificial Sequence
<220> FEATURE:

<223> OTHER INFORMATION: Nucleotide Sequence Encoding Chimeric Human
      IgG4 Light Chain of Anti-B7-H4 Antibody 2H9

<400> SEQUENCE: 37

```
gacattgtgc tgacccaatc tccagcttct ttggctgtgt ctctagggca gagggccacc    60
atctcctgca gagccagcga aagtattgat aattatggca ttagtttat gcactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtggaga ctgatgatgt tgcaacctat ttctgtcagc aaagtgatga gggtcggacg   300
ttcggtggag gcaccaagct ggaaatcaag cggaccgtgg ccgcccccag cgtgttcatc   360
ttccctccca gcgacgagca gctgaagtct ggcaccgcca gcgtggtgtg cctgctgaac   420
aacttctacc ccgcgaggc caaggtgcag tggaaggtgg acaacgccct gcagagcggc   480
aacagccagg agagcgtgac cgagcaggac tccaaggaca gcacctacag cctgagcagc   540
accctgaccc tgagcaaggc cgactacgag aagcacaagg tgtacgcctg cgaggtgacc   600
caccagggac tgtctagccc cgtgaccaag agcttcaacc ggggcgagtg c            651
```

<210> SEQ ID NO 38
<211> LENGTH: 217
<212> TYPE: PRT
<213> ORGANISM: Artificial Sequence
<220> FEATURE:
<223> OTHER INFORMATION: Amino Acid Sequence of Chimeric Human IgG4
      Light Chain of Anti-B7-H4 Antibody 2H9
<220> FEATURE:
<221> NAME/KEY: MISC_FEATURE
<222> LOCATION: (1)..(110)
<223> OTHER INFORMATION: Variable Domain

<400> SEQUENCE: 38

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Ile Asp Asn Tyr
             20                  25                  30

Gly Ile Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Arg Thr Asp Phe Thr Leu Thr Ile Asn
 65                  70                  75                  80

Pro Val Glu Thr Asp Asp Val Ala Thr Tyr Phe Cys Gln Gln Ser Asp
                 85                  90                  95

Glu Gly Arg Thr Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
```

```
                195                 200                 205
Thr Lys Ser Phe Asn Arg Gly Glu Cys
    210                 215
```

<210> SEQ ID NO 39
<211> LENGTH: 1335
<212> TYPE: DNA
<213> ORGANISM: Artificial Sequence
<220> FEATURE:
<223> OTHER INFORMATION: Nucleotide Sequence Encoding Chimeric Human
      IgG4 Heavy Chain of Anti-B7-H4 Antibody 2H9

<400> SEQUENCE: 39

```
gaagtgcagc tggtggagtc tgggggaaac ttagtgaagc tggagggtc cctgaaactc      60 tcctgtgcag cctctggatt cactttcagt aactctgcca tgtcttgggt tcgccagact     120
ccggaaaaga ggctggagtg ggtcgcaacc attagtgatg gtggtcgtta cacctactat     180
ccagacaatg taaagggccg attcaccatc tccagagaca tgccaagaa caacctgtac     240 ctgcaaatga gccatctgaa gtctgaggac acagcccttt attactgtgc aagagatcga     300
ccccactggt acttcgatgt ctggggcaca ggggccacgg tcaccgtctc ctcagctagc     360
accaagggtc catcggtctt cccactggcg ccttgctcca ggagcacctc cgagagcaca     420
gccgctctgg gttgcctggt caaggactac ttccccgaac cggtgacggt gtcgtggaac     480
tcaggtgccc tgaccagcgg cgtgcacacc ttcccggctg tcctacagtc ctcaggactc     540
tactccctca gcagcgtggt gaccgtgccc tccagcagct gggtacgaa gacctacacc     600 tgcaacgtag atcacaagcc cagcaacacc aaggtggaca gagagttga gtccaaatat     660 ggtcctccat gcccaccatg cccagcacct gagttcctgg gtggaccatc agtcttcctg     720
ttcccaccaa aacccaagga cactctcatg atctcccgga cccctgaggt cacgtgcgtc     780
gtagttgacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccacgagagc cacaggtgta caccctgcct ccatcccagg aagagatgac caagaaccag    1080
gtcagcctga cctgcctggt caaaggcttc taccctagcg acatcgccgt ggagtgggag    1140
agcaatgggc agccggagaa caactacaag accacgcctc cagtgctgga ctccgacggc    1200
tccttcttcc tctacagcag gctcaccgtg gacaagagca ggtggcagga gggtaatgtc    1260
ttctcatgct ccgtgatgca tgaggctctg cacaaccact acacacagaa gagcctgagc    1320
ctgagccccg gaaag                                                    1335
```

<210> SEQ ID NO 40
<211> LENGTH: 445
<212> TYPE: PRT
<213> ORGANISM: Artificial Sequence
<220> FEATURE:
<223> OTHER INFORMATION: Amino Acid Sequence of Chimeric Human IgG4
      Heavy Chain of Anti-B7-H4 Antibody 2H9
<220> FEATURE:
<221> NAME/KEY: MISC_FEATURE
<222> LOCATION: (1)..(118)
<223> OTHER INFORMATION: Variable Domain

<400> SEQUENCE: 40

```
Glu Val Gln Leu Val Glu Ser Gly Gly Asn Leu Val Lys Pro Gly Gly
1               5                   10                  15
```

```
Ser Leu Lys Leu Ser Cys Ala Ala Ser Gly Phe Thr Phe Ser Asn Ser
             20                  25                  30

Ala Met Ser Trp Val Arg Gln Thr Pro Glu Lys Arg Leu Glu Trp Val
         35                  40                  45

Ala Thr Ile Ser Asp Gly Gly Arg Tyr Thr Tyr Tyr Pro Asp Asn Val
     50                  55                  60

Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Leu Tyr Tyr Cys
                 85                  90                  95

Ala Arg Asp Arg Pro His Trp Tyr Phe Asp Val Trp Gly Thr Gly Ala
             100                 105                 110

Thr Val Thr Val Ser Ser Ala Ser Thr Lys Gly Pro Ser Val Phe Pro
         115                 120                 125

Leu Ala Pro Cys Ser Arg Ser Thr Ser Glu Ser Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Lys Thr Tyr Thr Cys Asn Val Asp His Lys Pro Ser
         195                 200                 205

Asn Thr Lys Val Asp Lys Arg Val Glu Ser Lys Tyr Gly Pro Pro Cys
     210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                 245                 250                 255

Val Thr Cys Val Val Val Asp Val Ser Gln Glu Asp Pro Glu Val Gln
             260                 265                 270

Phe Asn Trp Tyr Val Asp Gly Val Glu Val His Asn Ala Lys Thr Lys
         275                 280                 285

Pro Arg Glu Glu Gln Phe Asn Ser Thr Tyr Arg Val Val Ser Val Leu
     290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                 325                 330                 335

Ala Lys Gly Gln Pro Arg Glu Pro Gln Val Tyr Thr Leu Pro Pro Ser
             340                 345                 350

Gln Glu Glu Met Thr Lys Asn Gln Val Ser Leu Thr Cys Leu Val Lys
         355                 360                 365

Gly Phe Tyr Pro Ser Asp Ile Ala Val Glu Trp Glu Ser Asn Gly Gln
     370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                 405                 410                 415

Glu Gly Asn Val Phe Ser Cys Ser Val Met His Glu Ala Leu His Asn
             420                 425                 430
```

His Tyr Thr Gln Lys Ser Leu Ser Leu Ser Pro Gly Lys
        435                 440                 445

<210> SEQ ID NO 41
<211> LENGTH: 660
<212> TYPE: DNA
<213> ORGANISM: Artificial Sequence
<220> FEATURE:
<223> OTHER INFORMATION: Nucleotide Sequence Encoding Chimeric Human
      IgG4 Light Chain of Anti-B7-H4 Antibody 2E11

<400> SEQUENCE: 41

```
gacatcgtga tgagccagag ccctagcagc ctggccgtgt ccgtgggaga gaaagtgacc      60
gtgtcctgca agagcagcca gtccctgctg tactccacca accagagaac ctacctggcc     120
tggttccagc agaagcccgg ccagtctccc aagctgctga tctactgggc cagcaccaga     180
gaaagcggcg tgcccgacag attcacaggc agcggctctg gcaccgactt cacccctgaca    240 atcagcagcg tgaaggccga ggacctggct gtgtactact gccagcagta ctacaactac     300
ccctgaccct tcggcaccgg caccaagctg gaactgaaga aaccgtggc cgctcccagc      360 gtgttcatct cccacctag cgacgagcag ctgaagtccg gcacagcctc tgtcgtgtgc      420
ctgctgaaca acttctaccc ccgcgaggcc aaggtgcagt ggaaggtgga caacgccctg     480
cagagcggca acagccagga aagcgtgacc gagcaggaca gcaaggactc cacctacagc     540
ctgagcagca ccctgaccct gagcaaggcc gactacgaga agcacaaggt gtacgcctgc     600
gaagtgaccc accagggcct gtctagcccc gtgaccaaga gcttcaacag aggcgagtgc     660
```

<210> SEQ ID NO 42
<211> LENGTH: 220
<212> TYPE: PRT
<213> ORGANISM: Artificial Sequence
<220> FEATURE:
<223> OTHER INFORMATION: Amino Acid Sequence of Chimeric Human IgG4
      Light Chain of Anti-B7-H4 Antibody 2E11
<220> FEATURE:
<221> NAME/KEY: MISC_FEATURE
<222> LOCATION: (1)..(113)
<223> OTHER INFORMATION: Variable Domain

<400> SEQUENCE: 42

Asp Ile Val Met Ser Gln Ser Pro Ser Ser Leu Ala Val Ser Val Gly
1               5                   10                  15

Glu Lys Val Thr Val Ser Cys Lys Ser Ser Gln Ser Leu Leu Tyr Ser
            20                  25                  30

Thr Asn Gln Arg Thr Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Thr Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu

| | | | | 145 | | | | 150 | | | | 155 | | | | 160 |

Gln Ser Gly Asn Ser Gln Glu Ser Val Thr Glu Gln Asp Ser Lys Asp
                  165                  170                  175

Ser Thr Tyr Ser Leu Ser Ser Thr Leu Thr Leu Ser Lys Ala Asp Tyr
          180                  185                  190

Glu Lys His Lys Val Tyr Ala Cys Glu Val Thr His Gln Gly Leu Ser
        195                  200                  205

Ser Pro Val Thr Lys Ser Phe Asn Arg Gly Glu Cys
     210                  215                  220

<210> SEQ ID NO 43
<211> LENGTH: 1323
<212> TYPE: DNA
<213> ORGANISM: Artificial Sequence
<220> FEATURE:
<223> OTHER INFORMATION: Nucleotide Sequence Encoding Chimeric Human
    IgG4 Heavy Chain of Anti-B7-H4 Antibody 2E11

<400> SEQUENCE: 43

```
gaagtgaagc tggtggaatc tgagggcggc ctggtgcagc ctggcagcag catgaagctg      60
agctgtaccg ccagcggctt caagttcacc gactactaca tggcctgggt gcgacaggtg     120
cccgagaagg gactggaatg gtggccaac atcaactacg acggcagctc cacctactac     180
ctggacagcc tgaagtccag attcatcatc agcagagaca cgccaagaa catcctgtac     240
ctgcagatga actccctgaa gtctgaggac accgctacct actactgcgc cagaaagggc     300
tacttcgact actggggcca gggcaccacc ctgacagtgt ctagcgccag cacaaagggc     360
cccagcgtgt tccctctggc cccttgtagc agaagcacca gcgagtctac agccgccctg     420
ggctgcctcg tgaaggacta cttccccgag ccgtgaccg tgtcctggaa ctctggcgct     480
ctgacctctg gggtgcacac cttccctgcc gtgctgcagt ctagcggcct gtactctctg     540
agcagcgtcg tgacagtgcc agcagcagc ctgggcacca agacctacac ctgtaacgtg     600
gaccacaagc ccagcaacac caaggtggac aagagagtgg aatctaagta cggccctccc     660
tgccccccct tgtcctgctcc tgaatttctg ggcggaccct ccgtgtttct gttcccccca     720
aagcccaagg acaccctgat gatcagcaga accccgaag tgacctgcgt ggtggtggac     780
gtgtccagg aagatcccga ggtgcagttc aattggtacg tggacggcgt ggaagtgcac     840
aacgctaaga ccaagcccag agaggaacag ttcaacagca cctacagagt ggtgtccgtg     900
ctgacagtgc tgcatcagga ctggctgaac ggcaaagagt acaagtgcaa ggtgtccaac     960
aagggcctgc ctagcagcat cgaaaagacc atcagcaagg ccaagggcca gccccggaa    1020
ccccaggtgt acacactgcc tccaagccag gaagagatga ccaagaacca ggtgtccctg    1080
acctgtctcg tgaaaggctt ctaccccctc cgatatcgccg tggaatggga gagcaacggc    1140
cagcccgaga caactacaa gaccacccc cctgtgctgg actccgatgg ctcattcttc    1200
ctgtacagca gactgaccgt ggacaagtcc aggtggcagg aaggcaacgt gttcagctgc    1260
agcgtgatgc acgaggccct gcacaaccac tacacccaga agtccctgag cctgagcccc    1320
ggc                                                                 1323
```

<210> SEQ ID NO 44
<211> LENGTH: 441
<212> TYPE: PRT
<213> ORGANISM: Artificial Sequence
<220> FEATURE:
<223> OTHER INFORMATION: Amino Acid Sequence of Chimeric Human IgG4
    Heavy Chain of Anti-B7-H4 Antibody 2E11

```
<220> FEATURE:
<221> NAME/KEY: MISC_FEATURE
<222> LOCATION: (1)..(115)
<223> OTHER INFORMATION: Variable Domain

<400> SEQUENCE: 44

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Lys Phe Thr Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Asn Ser Leu Lys Ser Glu Asp Thr Ala Thr Tyr Tyr Cys
                85                  90                  95

Ala Arg Lys Gly Tyr Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380
```

```
Asn Tyr Lys Thr Thr Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440
```

```
<210> SEQ ID NO 45
<211> LENGTH: 60
<212> TYPE: DNA
<213> ORGANISM: Artificial Sequence
<220> FEATURE:
<223> OTHER INFORMATION: Polynucleotide Encoding Leader Sequence

<400> SEQUENCE: 45
atggagaccg acaccctgct gctctgggtg ctgctgctct gggtgcccgg ctccaccgga    60

<210> SEQ ID NO 46
<211> LENGTH: 20
<212> TYPE: PRT
<213> ORGANISM: Artificial Sequence
<220> FEATURE:
<223> OTHER INFORMATION: Leader Sequence

<400> SEQUENCE: 46

Met Glu Thr Asp Thr Leu Leu Leu Trp Val Leu Leu Leu Trp Val Pro
1               5                   10                  15

Gly Ser Thr Gly
            20

<210> SEQ ID NO 47
<211> LENGTH: 60
<212> TYPE: DNA
<213> ORGANISM: Artificial Sequence
<220> FEATURE:
<223> OTHER INFORMATION: Polynucleotide Encoding Leader Sequence

<400> SEQUENCE: 47
atgagcgtgc ccacacaggt gctgggactg ctgctgctgt ggctgaccga cgccagatgc    60

<210> SEQ ID NO 48
<211> LENGTH: 20
<212> TYPE: PRT
<213> ORGANISM: Artificial Sequence
<220> FEATURE:
<223> OTHER INFORMATION: Leader Sequence

<400> SEQUENCE: 48

Met Ser Val Pro Thr Gln Val Leu Gly Leu Leu Leu Leu Trp Leu Thr
1               5                   10                  15

Asp Ala Arg Cys
            20

<210> SEQ ID NO 49
<211> LENGTH: 57
<212> TYPE: DNA
<213> ORGANISM: Artificial Sequence
<220> FEATURE:
<223> OTHER INFORMATION: Polynucleotide Encoding Leader Sequence

<400> SEQUENCE: 49
atggaatggt cctgggtgtt cctgttcttc ctgagcgtga ccaccggcgt gcacagc       57
```

```
<210> SEQ ID NO 50
<211> LENGTH: 19
<212> TYPE: PRT
<213> ORGANISM: Artificial Sequence
<220> FEATURE:
<223> OTHER INFORMATION: Leader Sequence

<400> SEQUENCE: 50

Met Glu Trp Ser Trp Val Phe Leu Phe Phe Leu Ser Val Thr Thr Gly
1               5                   10                  15

Val His Ser
```

ANTI-B7-H4 ANTIBODIES AND THEIR USES

CROSS-REFERENCE TO RELATED APPLICATIONS

This application is a §371 application of the International Application No. PCT/US2012/050903 entitled "Anti-B7-H4 Antibodies and Their Uses", filed in the United States Receiving Office for the PCT on Aug. 15, 2012, which claims the benefit of and priority to U.S. Patent Application No. 61/523,819 filed Aug. 15, 2011, which application is herein incorporated by reference in its entirety.

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Field of the Invention

The present invention relates to anti-B7-H4 antibodies and their antigen-binding fragments and to other molecules that are capable of immunospecifically binding to B7-H4 (including fusion proteins that bind to the cognate antigen/receptor, etc.) and the uses of such molecules in the diagnosis and the treatment of cancer and other diseases. The invention particularly concerns the use of such molecules to retard or prevent tumor growth, inhibit tumor-mediated suppression, eliminate tumors and/or deplete or block the activity of tumor-associated macrophages ("TAMs") so as to alter their activity and/or decrease TAM-mediated immune suppression.

Description of Related Art

A. Cell Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T cells, and the release of various cytokines in response to the recognition of an antigen (Dong, C. et al. (2003) "*Immune Regulation by Novel Costimulatory Molecules*," Immunolog. Res. 28(1): 39-48).

The ability of T cells to optimally mediate an immune response against an antigen requires two distinct signaling interactions (Viglietta, V. et al. (2007) "*Modulating Co-Stimulation*," Neurotherapeutics 4:666-675; Korman, A. J. et al. (2007) "*Checkpoint Blockade in Cancer Immunotherapy*," Adv. Immunol. 90:297-339). First, antigen that has been arrayed on the surface of antigen-presenting cells (APC) must be presented to an antigen-specific naive CD4+ T cell. Such presentation delivers a signal via the T cell receptor (TCR) that directs the T cell to initiate an immune response that will be specific to the presented antigen. Second, a series of co-stimulatory signals, mediated through interactions between the APC and distinct T cell surface molecules, triggers first the activation and proliferation of the T cells and ultimately their inhibition. Thus, the first signal confers specificity to the immune response whereas the second signal serves to determine the nature, magnitude and duration of the response.

The immune system is tightly controlled by co-stimulatory ligands and receptors. These molecules provide the second signal for T cell activation and provide a balanced network of positive and negative signals to maximize immune responses against infection while limiting immunity to self (Wang, L. et al. (Mar. 7, 2011) "*VISTA, A Novel Mouse Ig Superfamily Ligand That Negatively Regulates T Cell Responses*," J. Exp. Med. 10.1084/jem.20100619:1-16; Lepenies, B. et al. (2008) "*The Role Of Negative Costimulators During Parasitic Infections*," Endocrine, Metabolic & Immune Disorders—Drug Targets 8:279-288). Of particular importance is binding between the B7.1 (CD80) and B7.2 (CD86) ligands of the APC and the CD28 and CTLA-4 receptors of T-lymphocytes (Sharpe, A. H. et al. (2002) "*The B7-CD28 Superfamily*," Nature Rev. Immunol. 2:116-126; Dong, C. et al. (2003) "*Immune Regulation by Novel Costimulatory Molecules*," Immunolog. Res. 28(1):39-48; Lindley, P. S. et al. (2009) "*The Clinical Utility Of Inhibiting CD28-Mediated Costimulation*," Immunol. Rev. 229:307-321). Binding of B7.1 or of B7.2 to CD28 stimulates T cell activation; binding of B7.1 or B7.2 to CTLA4 inhibits such activation (Dong, C. et al. (2003) "*Immune Regulation by Novel Costimulatory Molecules*," Immunolog. Res. 28(1): 39-48; Lindley, P. S. et al. (2009) "*The Clinical Utility Of Inhibiting CD28-Mediated Costimulation*," Immunol. Rev. 229:307-321; Greenwald, R. J. et al. (2005) "*The B7 Family Revisited*," Ann. Rev. Immunol. 23:515-548). CD28 is constitutively expressed on the surface of T cells (Gross, J., et al. (1992) "*Identification And Distribution Of The Costimulatory Receptor CD28 In The Mouse*," J. Immunol. 149: 380-388), whereas CTLA4 expression is rapidly up-regulated following T-cell activation (Linsley, P. et al. (1996) "*Intracellular Trafficking Of CTLA4 And Focal Localization Towards Sites Of TCR Engagement*," Immunity 4:535-543). Since CTLA4 is the higher affinity receptor (Sharpe, A. H. et al. (2002) "*The B7-CD28 Superfamily*," Nature Rev. Immunol. 2:116-126), binding first initiates T cell proliferation (via CD28) and then inhibits it (via nascent expression of CTLA4), thereby dampening the effect when proliferation is no longer needed.

Further investigations into the ligands of the CD28 receptor have led to the identification and characterization of a set of related B7 molecules (the "B7 Superfamily") (Coyle, A. J. et al. (2001) "*The Expanding B7 Superfamily: Increasing Complexity In Costimulatory Signals Regulating T Cell Function*," Nature Immunol. 2(3):203-209; Sharpe, A. H. et al. (2002) "*The B7-CD28 Superfamily*," Nature Rev. Immunol. 2:116-126; Greenwald, R. J. et al. (2005) "*The B7 Family Revisited*," Ann. Rev. Immunol. 23:515-548; Collins, M. et al. (2005) "*The B7 Family Of Immune-Regulatory Ligands*," Genome Biol. 6:223.1-223.7; Loke, P. et al. (2004) "*Emerging Mechanisms Of Immune Regulation: The Extended B7 Family And Regulatory T Cells*." Arthritis Res. Ther. 6:208-214; Korman, A. J. et al. (2007) "*Checkpoint Blockade in Cancer Immunotherapy*," Adv. Immunol. 90:297-339; Flies, D. B. et al. (2007) "*The New B7s: Playing a Pivotal Role in Tumor Immunity*," J. Immunother. 30(3): 251-260; Agarwal, A. et al. (2008) "*The Role Of Positive Costimulatory Molecules In Transplantation And Tolerance*," Curr. Opin. Organ Transplant. 13:366-372; Lenschow, D. J. et al. (1996) "*CD28/B7 System of T Cell Costimulation*," Ann. Rev. Immunol. 14:233-258; Wang, S. et al. (2004) "*Co-Signaling Molecules Of The B7-CD28 Family In Positive And Negative Regulation Of T Lympho-*

*cyte Responses*," Microbes Infect. 6:759-766). There are at least eight members of the family: B7.1 (CD80), B7.2 (CD86), the inducible co-stimulator ligand (ICOS-L; B7-H2), the programmed death-1 ligand (PD-L1; B7-H1), the programmed death-2 ligand (PD-L2; B7-DC), B7-H3 (B7-RP2), B7-H4 (also referred to as B7x and B7S1; Sica, G. L. et al. (2003) "*B7-H4, A Molecule Of The B7 Family, Negatively Regulates T Cell Immunity*," Immunity 18:849-861; Zang, X. et al. (2003) *B7x: A Widely Expressed B7 Family Member That Inhibits T Cell Activation*," Proc. Natl. Acad. Sci. (USA) 100:10388-10392; Prasad, D. V. et al. (2003) *B7S1, A Novel B7 Family Member That Negatively Regulates T Cell Activation*," Immunity 18:863-873) and B7-H6 (Brandt, C. S. et al. (2009) "*The B7 family member B7-H6 is a tumor cell ligand for the activating natural killer cell receptor NKp30 in humans*", J Exp Med. 206(7):1495-503).

B. B7-H4 cDNA encoding the human B7-H4 protein was identified and cloned from placental cDNA (Sica, G. L. et al. (2003) "*B7-H4, A Molecule Of The B7 Family, Negatively Regulates T Cell Immunity*," Immunity 18:849-861; Zang, X. et al. (2003) *B7x: A Widely Expressed B7 Family Member That Inhibits T Cell Activation*," Proc. Natl. Acad. Sci. (USA) 100:10388-10392). B7-H4 is discussed in U.S. Pat. Nos. 7,931,896; 7,875,702; 7,847,081; 7,622,565; in United States Patent Publications Nos. 2011/0085970; 2011/0020325; 2010/0256000; 2010/0240585; 2010/0227343; 2010/0227335; 2010/0158936; 2010/0092524; 2010/0028450; 2009/0275633; 2009/0215084; 2009/0176317; 2009/0142342; 2009/0118175; 2009/0087416; 2009/0048122; 2009/0022747; 2009/0018315; 2008/0206235; 2008/0160036; 2008/0177039; 2008/0050370; 2007/0218032; 2007/0184473; 2007/0172504; 2007/0160578; 2007/0122378; 2007/0036783; 2006/0003452; in European Patent Publications Nos. EP 2124998 and EP 2109455; and in PCT Patent Publications WO 2011/026132A2; WO 2011/026122A2; WO 2011/005566A2; WO 2010/144295A1; WO 2010/102177A1; WO 2010/102167A1; WO 2009/111315A2; WO 2009/073533A2; WO 2008/092153A2; WO 2008/083239A2; WO 2008/083228A2; WO 2007/124361A2; WO 2007/122369A2; WO 2007/109254A2; WO 2007/087341A2; WO 2007/082154A2; WO 2007/067682A2; WO 2007/067681A2; WO 2007/041694A2; WO 2006/138670A2; WO 2006/133396A2; WO 2006/121991A2; WO 2006/066229A2; and WO 2006/007539A1.

Anti-B7-H4 antibodies are disclosed in U.S. Pat. Nos. 7,888,477; 7,737,255; 7,619,068; 6,962,980, and in United States Patent Publication No. 20080199461.

The B7-H4 protein possesses 282 amino acid residues, which have been categorized as comprising an amino terminal extracellular domain, a large hydrophobic transmembrane domain and a very short intracellular domain (consisting of only 2 amino acid residues). Like other B7 family members, B7-H4 possesses a pair of Ig-like regions in its extracellular domain. The B7-H4 protein has an overall structure of a type I transmembrane protein. The protein has minimal (about 25%) homology with other B7 family members (Zang, X. et al. (2003) *B7x: A Widely Expressed B7 Family Member That Inhibits T Cell Activation*," Proc. Natl. Acad. Sci. (USA) 100:10388-10392).

The human B7-H4 cDNA sequence has been used to identify a murine B7-H4 homolog. The level of identity between the murine and human orthologs (approximately 87%) suggests that B7-H4 is highly conserved evolutionarily (Sica, G. L. et al. (2003) "*B7-H4, A Molecule Of The B7 Family, Negatively Regulates T Cell Immunity*," Immunity 18: 849-861; Zang, X. et al. (2003) *B7x: A Widely Expressed B7 Family Member That Inhibits T Cell Activation*," Proc. Natl. Acad. Sci. (USA) 100:10388-10392). The extensive homology increases to 91% for the IgV domains of the proteins, which are involved in binding the B7-H4 receptor (Stamper, C. C. et al. (2001) "*Crystal Structure Of The B7-1/CTLA-4 Complex That Inhibits Human Immune Responses*," Nature 410: 608-611; Schwartz, J. C. et al. (2001) "*Structural Basis For Co-Stimulation By The Human CTLA-4/B7-2 Complex*," Nature 410:604-608).

In contrast to other B7 members, B7-H4 mRNA is widely expressed. Its expression has been found in the brain, heart, kidney, liver, lung, ovary, pancreas, placenta, prostate, skeletal muscle, skin, small intestine, spleen, stomach, testis, thymus, thymus, and uterus (Sica, G. L. et al. (2003) "*B7-H4, A Molecule Of The B7 Family, Negatively Regulates T Cell Immunity*," Immunity 18:849-861; Zang, X. et al. (2003) *B7x: A Widely Expressed B7 Family Member That Inhibits T Cell Activation*," Proc. Natl. Acad. Sci. (USA) 100:10388-10392; Prasad, D. V. et al. (2003) *B7S1, A Novel B7 Family Member That Negatively Regulates T Cell Activation*," Immunity 18:863-873; Prasad, D. V. et al. (2003) *B7S1, A Novel B7 Family Member That Negatively Regulates T Cell Activation*," Immunity 18:863-873).

Despite the widespread expression of B7-H4 mRNA, the presence of B7-H4 protein on the surface of normal cells seems to be limited (Sica, G. L. et al. (2003) "*B7-H4, A Molecule Of The B7 Family, Negatively Regulates T Cell Immunity*," Immunity 18:849-861; Choi, I. H. et al. (2003) "*Genomic Organization And Expression Analysis Of B7-H4, An Immune Inhibitory Molecule Of The B7 Family*," J. Immunol. 171:4650-4654). Although freshly isolated human T cells, B cells, monocytes, and dendritic cells do not express B7-H4 on their cell surfaces (as determined via FACS analysis), its expression can be induced on such cells after in vitro stimulation lipopolysaccharides (LPS), phytohemagglutinin (PHA), gamma interferon (IFN-γ), phorbol 12-myristate 13-acetate (PMA), or ionomycin (Sica, G. L. et al. (2003) "*B7-H4, A Molecule Of The B7 Family, Negatively Regulates T Cell Immunity*," Immunity 18:849-861). The finding of such a wide distribution of B7-H4 expression suggests that the function of B7-H4 is quite distinct from that of other inhibitory B7 molecules (see, Zang, X. et al. (2003) *B7x: A Widely Expressed B7 Family Member That Inhibits T Cell Activation*," Proc. Natl. Acad. Sci. (USA) 100:10388-10392).

Consistent with this suggestion and the observation that the extracellular domain of B7-H4 has only about 25% amino acid homology with other B7 family members, B7-H4 does not bind to known B7 family receptors (i.e., CTLA-4, ICOS, PD-1 or CD28). Efforts to identify a B7-H4-specific receptor have revealed that such a receptor is expressed on activated T cells (Sica, G. L. et al. (2003) "*B7-H4, A Molecule Of The B7 Family, Negatively Regulates T Cell Immunity*," Immunity 18:849-861). Binding of B7-H4 fusion protein to its putative receptor on T cells was found to significantly inhibit T cell proliferation and cytokine (IL-2 and IL-10) production and such inhibition was found to be non-reversible by CD28 co-stimulation (Zang, X. et al. (2003) *B7x: A Widely Expressed B7 Family Member That Inhibits T Cell Activation*," Proc. Natl. Acad. Sci. (USA) 100:10388-10392; Prasad, D. V. et al. (2003) *B7S1, A Novel B7 Family Member That Negatively Regulates T Cell Activation*," Immunity 18:863-873). B7-H4 has been found to arrest cell cycle progression of T cells in $G_0/G_1$ phase (Sica, G. L. et al. (2003) "*B7-H4, A Molecule Of The B7 Family, Negatively Regulates T Cell Immunity*,"

Immunity 18:849-861) suggesting that the protein mediates its inhibitory effects by arresting the cell cycle rather than by inducing apoptosis.

Anti-B7-H4 antibodies have been found to greatly increase the levels of IL-2 production by spleen cells in vitro, and to lead to a stronger immune response in vivo (Prasad, D. V. et al. (2003) *B7S1, A Novel B7 Family Member That Negatively Regulates T Cell Activation,*" Immunity 18:863-873; Zang, X. et al. (2003) *B7x: A Widely Expressed B7 Family Member That Inhibits T Cell Activation,*" Proc. Natl. Acad. Sci. (USA) 100:10388-10392; Prasad, D. V. et al. (2003) *B7S1, A Novel B7 Family Member That Negatively Regulates T Cell Activation,*" Immunity 18:863-873).

An absence of B7-H4 has been demonstrated to lead to resistance to *Listeria monocytogenes* infection through the direct regulation of the growth of neutrophil progenitors (Zhu, G. et al. (2009) "*B7-H4 Deficient Mice Display Augmented Neutrophil-Mediated Innate Immunity,*" Blood 113:1759-1769; Wei, J. et al. (2011) "*Tissue-Specific Expression Of B7x Protects From CD4 T Cell Mediated Autoimmunity,*" J. Exper. Med. 208(8):1683-1694). As such B7-H4 has been proposed to play a role in immunity, especially autoimmunity and resistance to infection. Thus agonist anti-B7-H4 antibodies and soluble B7-H4 protein have been proposed for the treatment of inflammatory disorders (U.S. Pat. No. 7,931,896; United States Patent Publications Nos. 2007/0122378; 2008/0160036; 2009/0142342; and 2011/0020325; European Patent Publication No. EP 2124998; PCT Patent Publications Nos. WO 2006/133396; WO 2007/041694; WO 2008/083228; WO 2009/111315; WO 2010/144295; WO 2011/005566; WO 2011/026122; and WO 2011/026132).

The in vivo significance of B7-H4 is additionally demonstrated by the high levels of B7-H4 expression found in numerous tumor tissues, for example, human ovarian cancers (Choi, I. H. et al. (2003) "*Genomic Organization And Expression Analysis Of B7-H4, An Immune Inhibitory Molecule Of The B7 Family,*" J. Immunol. 171:4650-4654; Kryczek, I. et al. (2006) "*B7-H4 Expression Identifies A Novel Suppressive Macrophage Population In Human Ovarian Carcinoma,*" J. Exp. Med. 203(4):871-881; Bignotti, E. et al. (2006) "*Differential Gene Expression Profiles Between Tumor Biopsies And Short Term Primary Cultures Of Ovarian Serous Carcinomas: Identification Of Novel Molecular Biomarkers For Early Diagnosis And Therapy,*" Gynecol. Oncol. 103:405-416; Tringler, B. et al. (2006) "*B7-H4 Overexpression In Ovarian Tumors,*" Gynecol. Oncol. 100: 44-52; Simon, I. et al. (2006) "*B7-h4 Is A Novel Membrane-Bound Protein And A Candidate Serum And Tissue Biomarker For Ovarian Cancer,*" Cancer Res. 66:1570-1575; Salceda, S. et al. (2005) "*The Immunomodulatory Protein B7-H4 Is Overexpressed In Breast And Ovarian Cancers And Promotes Epithelial Cell Transformation,*" Exp. Cell Res. 306:128-141), non-small-cell lung cancer (Sun, Y. et al. (2006) "*B7-H3 And B7-H4 Expression In Non-Small-Cell Lung Cancer,*" Lung Cancer 53:143-151), ductal and lobular breast cancer (Salceda, S. et al. (2005) "*The Immunomodulatory Protein B7-H4 Is Overexpressed In Breast And Ovarian Cancers And Promotes Epithelial Cell Transformation,*" Exp. Cell Res. 306:128-141; Tringler, B. et al. (2005) "*B7-H4 Is Highly Expressed In Ductal And Lobular Breast Cancer,*" Clin. Cancer Res. 11:1842-1848), and renal cell carcinoma (Krambeck, A. E. et al. (2006) "*B7-H4 Expression In Renal Cell Carcinoma And Tumor Vasculature: Associations With Cancer Progression And Survival,*" Proc. Natl. Acad. Sci. (USA) 103:10391-10396). The expression of B7-H4 on tumor cells has been found to correlate with adverse clinical and pathologic features, including tumor aggressiveness (Krambeck, A. E. et al. (2006) "*B7-H4 Expression In Renal Cell Carcinoma And Tumor Vasculature: Associations With Cancer Progression And Survival,*" Proc. Natl. Acad. Sci. (U.S.A.) 103(2): 10391-10396).

C. Tumor-Associated Macrophages (TAMs)

The association between inflammation and cancer dates back more than a century to observations noting infiltration of large numbers of white blood cells into tumor sites (Balkwill, F. et al. (2001) "*Inflammation And Cancer: Back To Virchow?,*" Lancet 357:539-545; Coussens, L. M. et al. (2002) "*Inflammation and Cancer,*" Nature 420:860-867). Several studies have now identified two main pathways linking inflammation and cancer: an intrinsic and an extrinsic pathway (Allavena, P. et al. (2008) "*Pathways Connecting Inflammation and Cancer,*" Curr. Opin. Genet. Devel. 18:3-10; Colotta, F. (2009) "*Cancer-Related Inflammation, The Seventh Hallmark of Cancer: Links to Genetic Instability,*" Carcinogenesis 30(7): 1073-1081; Porta, C. et al. (2009) "*Cellular and Molecular Pathways Linking Inflammation and Cancer,*" Immunobiology 214:761-777). The intrinsic pathway includes genetic alterations that lead to inflammation and carcinogenesis, whereas the extrinsic pathway is characterized by microbial/viral infections or autoimmune diseases that trigger chronic inflammation in tissues associated with cancer development. Both pathways activate pivotal transcription factors of inflammatory mediators (e.g., NF-κB, STAT3, and HIF-1) and result in the recruitment of leukocytes that play a key role in inflammation (Solinas, G. et al. (2009) "*Tumor-Associated Macrophages (TAM) As Major Players Of The Cancer-Related Inflammation,*" J. Leukoc. Biol. 86(5):1065-1073).

TAMs provide a link between inflammation and cancer. Macrophages are immune system cells derived from activated blood monocytes. They are primarily recognized as participating in inflammatory responses induced by pathogens or tissue damage by acting to remove (i.e., phagocytose) pathogens, dead cells, cellular debris, and various components of the extra-cellular matrix (ECM). Macrophages have been found to constitute an important constituent in the tumor microenvironment and to represent up to 50% of the tumor mass In addition to mediating phagocytosis, macrophages secrete pro-angiogenic growth factors and matrix-remodeling proteases, and thus play a role in the development of the vascular infrastructure (i.e., angiogenesis) needed for tumor development and growth (Pollard, J.W. (2009) "*Trophic Macrophages In Development And Disease,*" Nat. Rev. Immunol. 9:259-270). As such, the presence of macrophages within a tumor appears to assist the growth of the tumor. A number of studies provide evidence that the presence of tumor-associated macrophages within the tumor is a negative prognostic factor of survival (Farinha, P. et al. (2005) "*Analysis Of Multiple Biomarkers Shows That Lymphoma-Associated Macrophage (LAM) Content Is An Independent Predictor Of Survival In Follicular Lymphoma (FL),*" Blood 106:2169-2174; Dave, S. S. et al. (2004) "*Prediction Of Survival In Follicular Lymphoma Based On Molecular Features Of Tumor-Infiltrating Immune Cells,*" N. Engl. J. Med. 351:2159-2169; Solinas, G. et al. (2009) "*Tumor-Associated Macrophages (TAM) As Major Players Of The Cancer-Related Inflammation,*" J. Leukoc. Biol. 86(5):1065-1073).

B7-H4 has been shown to be over-expressed in TAMs including those present in ovarian tumors (Kryczek, I. et al. (2006) "*B7-H4 Expression Identifies A Novel Suppressive*

*Macrophage Population In Human Ovarian Carcinoma,*" J. Exp. Med. 203(4):871-881; Kryczek, I. et al. (2007) "*Relationship Between B7-H4, Regulatory T Cells, And Patient Outcome In Human Ovarian Carcinoma,*" Cancer Res. 67(18):8900-8905).

Despite all prior advances in the treatment of inflammation and cancer, a need remains for compositions capable of providing enhanced immunotherapy for the treatment of cancer. The present invention is directed to such compositions and their use to treat cancer and other diseases and conditions.

SUMMARY OF THE INVENTION

The present invention relates to anti-B7-H4 antibodies and their antigen-binding fragments and to other molecules that are capable of immunospecifically binding to B7-H4 (including fusion proteins that bind to the cognate antigen/receptor, etc.) and the uses of such molecules in the diagnosis and the treatment of cancer and other diseases. The invention particularly concerns the use of such molecules to retard or prevent tumor growth, inhibit tumor-mediated suppression, eliminate tumors and/or to modulate or deplete TAMs so as to alter their activity and/or decrease TAM-mediated immune suppression.

In detail, the invention provides a molecule, comprising an antigen-binding fragment of an antibody that immunospecifically binds to human B7-H4, and preferably the embodiment wherein such B7-H4 binding molecule is able to bind to B7-H4 arrayed on the surface of a live cell and/or wherein such B7-H4 binding molecule is able to bind to B7-H4 expressed at an endogenous concentration.

The invention provides a molecule, comprising an antigen-binding fragment of an antibody, wherein the molecule immunospecifically binds to human B7-H4. The invention particularly provides such a molecule that immunospecifically binds to human B7-H4:

(I) arrayed on the surface of a cell (especially a live cell);
(II) arrayed on the surface of a cell (especially a live cell) at an endogenous concentration;
(III) arrayed on the surface of a live cell, and modulates binding between B7-H4 and its cellular receptor;
(IV) arrayed on the surface of a live cell, and inhibits immune suppression by tumor-associated macrophages;
(V) arrayed on the surface of a live cell, and modulates an activity of a tumor-associated macrophage;
(VI) arrayed on the surface of a live tumor cell and inhibits tumor-mediated suppression; or
(VII) arrayed on the surface of a live tumor cell and causes tumor-specific cell lysis.

The invention further concerns the embodiments of such molecules wherein such molecules are detectably labeled or comprises a conjugated toxin, drug, receptor, enzyme, receptor ligand. The invention further concerns the embodiments of all such molecules wherein the molecule is capable of being internalized into the cell and of mediating the death of the cell.

The invention further concerns the embodiments of all such molecules wherein the live cell is a tumor cell, a pathogen-infected cell or a macrophage.

The invention further concerns the embodiments of all such molecules wherein the molecule is an antibody, and wherein the antibody is:

(I) a monoclonal antibody, a human antibody, a chimeric antibody or a humanized antibody; or
(II) a bispecific, trispecific or multispecific antibody.

The invention further concerns the embodiments of all such molecules wherein the molecule has ADCC activity and is capable of direct tumor killing activity and/or inhibiting TAM- or tumor-mediated suppression.

The invention further concerns the embodiments of all such molecules wherein the molecule is a bispecific, trispecific or multispecific antibody that is capable of binding B7-H4 and a different molecule on the same cell.

The invention further concerns the embodiments of all such molecules wherein the antigen-binding fragment comprises six CDRs, and wherein:

(I) the six CDRs comprise at least one consensus CDR of the CDRs of anti-B7-H4 antibodies: 2D1, 2E11 and 2H9, with all remaining CDRs selected from:
  (A) the three light chain and the three heavy chain CDRs of anti-B7-H4 antibody 2D1;
  (B) the three light chain and the three heavy chain CDRs of anti-B7-H4 antibody 2E11; or
  (C) the three light chain and the three heavy chain CDRs of anti-B7-H4 antibody 2H9;
or
(II) the six CDRs are:
  (A) the three light chain and the three heavy chain CDRs of anti-B7-H4 antibody 2D1;
  (B) the three light chain and the three heavy chain CDRs of anti-B7-H4 antibody 2E11; or
  (C) the three light chain and the three heavy chain CDRs of anti-B7-H4 antibody 2H9.

The invention further provides a pharmaceutical composition for the treatment of cancer or infectious disease, comprising a therapeutically effective or prophylactically effective amount of any of the above-described molecules, and a physiologically acceptable carrier or excipient, wherein the molecule antagonizes a B7-H4-mediated suppression to up-modulate an immune response.

The invention further includes the use of such pharmaceutical composition for the treatment of cancer or infectious disease (especially a chronic viral infection) in a subject exhibiting a symptom of the cancer or infectious disease or for the prevention of cancer or infectious disease in a subject in advance of the exhibition of the symptom.

The invention further provides a pharmaceutical composition for the treatment of inflammation, comprising a therapeutically effective or prophylactically effective amount of any of the above-described molecules, and a physiologically acceptable carrier or excipient, wherein the molecule enhances B7-H4-mediated suppression to down-modulate an immune response.

The invention further includes the use of such pharmaceutical composition for the treatment of inflammation (especially an autoimmune disease, a graft vs host disease, a host vs graft disease, or a transplantation rejection response, and the use is the treatment of the autoimmune disease, a graft vs host disease, a host vs graft disease, or a transplantation rejection response)

The invention further includes the use of any of the above-described molecules in a cytologic assay for diagnosing the presence of a disease (especially cancer or a disease affecting T cell number or health) in a subject, wherein the cytologic assay comprises assaying cells of the subject for their ability to bind to the molecule.

The invention further includes the use of any of the above-described molecules to determine the suitability of a subject for treatment of a tumor with an anti-cancer agent, wherein the use comprises determining the effective or actual concentration of tumor-associated macrophages in the tumor, and particularly wherein the dose of the anti-cancer agent or the treatment with the anti-cancer agent is set or adjusted based on the determined effective or actual concentration of the tumor-associated macrophages.

The invention further includes the use of a therapeutically effective amount of any of the above-described pharmaceutical compositions in treating cancer in a patient identified as exhibiting an elevated effective concentration of B7-H4-expressing tumor-associated macrophages.

The invention further includes such uses wherein the treatment of the tumor or the cancer additionally comprises chemotherapy, a hormonal therapy, a biological therapy, an immunotherapy, a radiation therapy or surgery.

The invention additionally concerns the embodiment of such B7-H4 binding molecule, wherein the cell (or live cell) is a tumor cell, a pathogen-infected cell or a macrophage.

The invention additionally concerns the embodiment of such B7-H4 binding molecule, wherein the molecule modulates binding between B7-H4 and its cellular receptor.

The invention particularly concerns the embodiment of such B7-H4 binding molecules wherein the antigen-binding fragment comprises six CDRs, wherein the CDRs comprise at least one consensus CDR of the CDRs of anti-B7-H4 antibodies: 2D1, 2E11 and 2H9, with all remaining CDRs selected from:
(A) the three light chain and the three heavy chain CDRs of anti-B7-H4 antibody 2D1;
(B) the three light chain and the three heavy chain CDRs of anti-B7-H4 antibody 2E11; or
(C) the three light chain and the three heavy chain CDRs of anti-B7-H4 antibody 2H9.

The invention particularly concerns the embodiment of such B7-H4 binding molecules wherein the six CDRs are:
(A) the three light chain and the three heavy chain CDRs of anti-B7-H4 antibody 2D1;
(B) the three light chain and the three heavy chain CDRs of anti-B7-H4 antibody 2E11; or
(C) the three light chain and the three heavy chain CDRs of anti-B7-H4 antibody 2H9.

The invention particularly concerns the embodiment of all such B7-H4 binding molecules wherein the molecule is a monoclonal antibody, a human antibody, a chimeric antibody or a humanized antibody. The invention further concerns the embodiment of such antibodies wherein the antibody is a bispecific, trispecific or multispecific antibody.

The invention further concerns the embodiment of all such B7-H4 binding molecules wherein the molecule is detectably labeled or comprises a conjugated toxin, drug, receptor, enzyme, receptor ligand.

The invention particularly concerns the embodiment of all such B7-H4 binding molecules wherein the molecule depletes tumor associated macrophages or modulates their activity.

The invention is additionally directed to a pharmaceutical composition for the treatment of cancer, comprising a therapeutically effective amount of any of the above-described molecules, and a physiologically acceptable carrier or excipient. The invention is additionally directed to a method for treating cancer in a subject exhibiting a symptom of the disease which comprises administering to the subject, a therapeutically effective amount of such pharmaceutical composition. The invention is additionally directed to the embodiment of such method wherein the dose of the anti-cancer agent or the treatment with the anti-cancer agent is set or adjusted based on the determined effective or actual concentration of the tumor-associated macrophages. The invention is additionally directed to a method of treating a tumor in a patient identified as exhibiting an elevated effective concentration of B7-H4-expressing tumor-associated macrophages, which comprises providing to the patient a therapeutically effective amount of such pharmaceutical composition. The invention is additionally directed to the embodiments of such methods wherein the method additionally comprises combining the treatment with chemotherapy, a hormonal therapy, a biological therapy, an immunotherapy, a radiation therapy or surgery. The invention is additionally directed to a method for prophylactically treating such cancer which comprises administering to a subject in advance of exhibiting a symptom of the disease a prophylactically effective amount of such pharmaceutical composition.

The invention is additionally directed to a method for determining the suitability of a subject for treatment of a tumor with an anti-cancer agent, wherein the method comprises employing any of the above-described molecules to determine the effective or actual concentration of tumor associated macrophages in the tumor.

The invention is additionally directed to a pharmaceutical composition for the treatment of an infectious disease (especially a chronic viral disease), comprising a therapeutically effective is additionally directed to a method for prophylactically treating such inflammatory disease which comprises administering to a subject in advance of exhibiting a symptom of the disease a prophylactically effective amount of such pharmaceutical composition.

The invention is additionally directed to a method for diagnosing a disease (especially cancer, or a disease affecting T cell number or health) in a subject comprising assaying cells of the subject for their ability to bind to a molecule, comprising an antigen-binding fragment of an antibody that immunospecifically binds to human B7-H4, and preferably the embodiment wherein such B7-H4 binding molecule is able to bind to B7-H4 arrayed on the surface of a live cell and/or wherein such B7-H4 binding molecule is able to bind to B7-H4 expressed at an endogenous concentration, and particularly concerns the embodiment wherein the method provides a cytologic assay for diagnosing the presence of the disease in the subject.

DETAILED DESCRIPTION OF THE INVENTION

Figure 1:
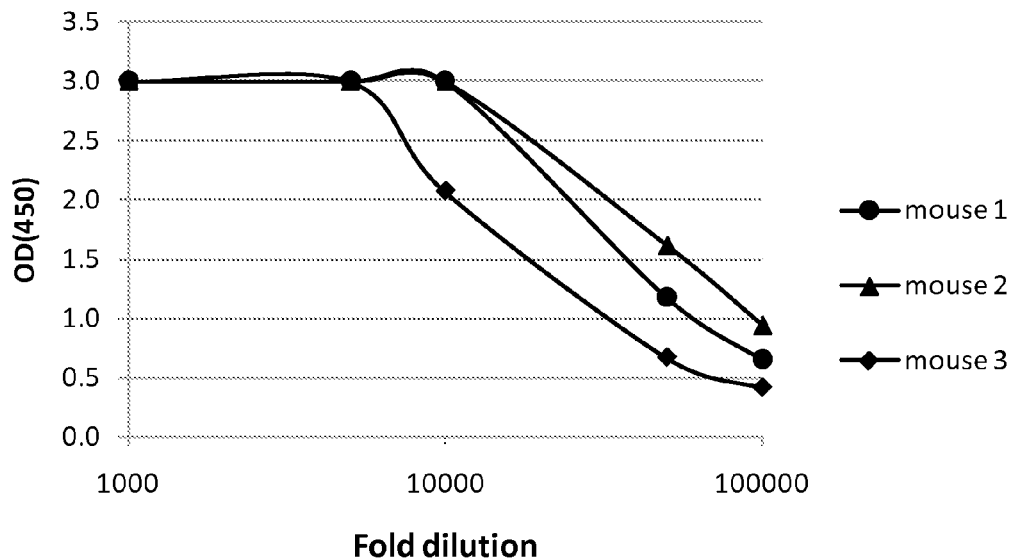
FIG. 1 shows the detection of anti-B7-H4 antibody (as measured by $OD_{450}$) by serum from 3 individual mice immunized with a murine B7-H4Ig construct.

As discussed above, incipient tumors need to generate their own vasculature to enable oxygen and nourishment delivery to the expanding tumor cells. Thus, the progression of tumors requires coordinated signaling between tumor cells and non-malignant cells in the tumor microenvironment (Kaler, P. et al. (2010) "*Tumor Associated Macrophages Protect Colon Cancer Cells from TRAIL-Induced Apoptosis through IL-1β-Dependent Stabilization of Snail in Tumor Cells,*" PLos ONE 5(7):e11700 1-13). It is now well established that TAMs, as well as neutrophils, fibroblasts and other cells cooperate with tumor cells to facilitate angiogenesis in tumors (Nucera, S. et al. (2011) "*The Interplay Between Macrophages And Angiogenesis In Development, Tissue Injury And Regeneration,*" Int. J. Dev. Biol. doi: 10.1387/ijdb.103227sn; Zamarron, B. F. et al. (2011) "*Dual Roles Of Immune Cells And Their Factors In Cancer Development And Progression,*" Int. J. Biol. Sci. 7(5):651-658; Liu, J. et al. (2011) "*Tumor-Associated Macrophages Recruit CCR6+Regulatory T Cells And Promote The Development Of Colorectal Cancer Via Enhancing CCL20 Production In Mice,*" PLoS One. 6(4):e19495; Rigo, A. et al. (2010) "*Macrophages May Promote Cancer Growth Via A GM-CSF/HB-EGF Paracrine Loop That Is Enhanced By CXCL12,*" Molec. Cancer 9(273):1-13; Lin, J. Y. et al. (2011) "*Clinical Significance Of Tumor-Associated Macrophage Infiltration In Supraglottic Laryngeal Carcinoma,*" Chin. J. Cancer 30(4):280-286; Vergati, M. (2011) "*The Consequence Of Immune Suppressive Cells In The Use Of Therapeutic Cancer Vaccines And Their Importance In Immune Monitoring,*" J. Biomed. Biotechnol. 2011:182413).

The high levels of B7-H4 expression found in numerous tumor tissues, for example, human ovarian cancers, points to a key role for B7-H4 in mediating immune suppression. TAMs expressing B7-H4 have been found to suppress tumor-associated antigen-specific T cell immunity (Kryczek, I. et al. (2006) "*B7-H4 Expression Identifies A Novel Suppressive Macrophage Population In Human Ovarian Carcinoma,*" J. Exp. Med. 203(4):871-881). The intensity of B7-H4 expression in TAMs correlates significantly with Treg cell numbers in the tumor. Furthermore, B7-H4 expressed on TAMs, is associated with poor patient outcome (Kryczek, I. et al. (2006) "*B7-H4 Expression Identifies A Novel Suppressive Macrophage Population In Human Ovarian Carcinoma,*" J. Exp. Med. 203(4):871-881). Previously published data also showed that TAMs spontaneously produce chemokine CCL22 that mediates Treg cell trafficking into the tumor, and Treg cell-induced B7-H4 expression on antigen-presenting cells (APC), including TAMs themselves (Kryczek, I. et al. (2006) "*Cutting Edge: Induction Of B7-H4 On APCs Through IL-10: Novel Suppressive Mode For Regulatory T Cells,*" J. Immunol. 177(1):40-44). Taken together, such findings suggest that TAMs expressing B7-H4 play a very important role on immune suppression in the tumor microenvironment allowing the tumor to avoid detection by the immune system ("immune evasion"). By blocking $B_7$-$H_4$, modulating its surface expression, modulating $B_7$-$H_4$-mediated signal transduction, or depleting TAMs' $B_7$-$H_4$, molecules (including anti-B7-H4 antibodies) that are capable of immunospecifically binding to B7-H4, or preventing interaction with its native receptor, provide a novel strategy as an effective immunotherapy for cancer.

The present invention thus relates to antibodies (including anti-B7-H4 antibodies) and their antigen-binding fragments and to other molecules (including proteins and fusion proteins that bind to the cognate antigen/receptor, etc.) that are capable of immunospecifically binding to B7-H4 (especially human B7-H4) and their uses in the diagnosis and the treatment of cancer and other diseases. The invention particularly concerns the use of such molecules to retard or prevent tumor growth, inhibit tumor-mediated suppression, eliminate tumors and/or to deplete or block the activity of TAMs to decrease TAM-mediated immune suppression.

In particular, the present invention provides anti-B7-H4 antibodies that can be used to target TAMs and screen for various functional activities, including modulating the interaction between B7-H4 and its putative receptor(s), modulation of B7-H4 levels and attenuation of negative signaling and/or depletion of B7-H4 positive cells. Using recombinant DNA technology, B7-H4 antibodies can be engineered to comprise Fc domains having little or no Fc receptor (FcR) binding activity, enhanced antibody-dependent cell-mediated cytotoxicity (ADCC) or enhanced complement dependent cytotoxicity (CDC) activities. Such recombinant antibodies may be used as modulatory molecules to decrease or prevent B7-H4 on the TAMs from interacting with inhibitory receptor(s) on T cells or other cells in the tumor microenvironment, thereby releasing T cells or other functional cells from B7-H4 check point ("break")/suppressive signaling. Fc functional recombinant B7-H4 antibody may induce ADCC or CDC causing depletion of the TAMs expressing B7-H4, which potentially releases T cells or other functional cells from check point, in addition to other activities such as B7-H4 modulation from the surface of suppressive cells, or direct killing of B7-H4 expressing cells. Anti-B7-H4 antibodies with ADCC activity may be particularly useful for simultaneously depleting B7-H4-expressing tumor cells and inhibiting TAM-mediated immune suppression.

The sequence of human B7-H4 is (SEQ ID NO:1):

```
MASLGQILFW SIISIIIILA GAIALIIGFG ISGKHSITVT

TVASAGNIGE DGILSCTFEP DIKLSDIVIQ WLKEGVLGLV

HEFKEGKDEL SEQDEMFRGR TAVFADQVIV GNASLRLKNV
```

```
QLTDAGTYKC YIITSKGKGN ANLEYKTGAF SMPEVNVDYN

ASSETLRCEA PRWFPQPTVV WASQVDQGAN FSEVSNTSFE

LNSENVTMKV VSVLYNVTIN NTYSCMIEND IAKATGDIKV

TESEIKRRSH LQLLNSKASL CVSSFFAISW ALLPLSPYLM

LK
```

The sequence of murine B7-H4 is (SEQ ID NO:2):

```
MASLGQIIFW SIINIIIILA GAIALIIGFG ISGKHFITVT

TFTSAGNIGE DGTLSCTFEP DIKLNGIVIQ WLKEGIKGLV

HEFKEGKDDL SQQHEMFRGR TAVFADQVVV GNASLRLKNV

QLTDAGTYTC YIRTSKGKGN ANLEYKTGAF SMPEINVDYN

ASSESLRCEA PRWFPQPTVA WASQVDQGAN FSEVSNTSFE

LNSENVTMKV VSVLYNVTIN NTYSCMIEND IAKATGDIKV

TDSEVKRRSQ LQLLNSGPSP CVFSSAFVAG WALLSLSCCL

MLR
```

As used herein, a molecule is said to be able to "immunospecifically bind" a second molecule if such binding exhibits the specificity and affinity of an antibody to its cognate antigen. Antibodies are said to be capable of "immunospecifically binding" to a target region or conformation ("epitope") of an antigen (and in particular, the antigen B7-H4) if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region. A molecule is said to "physiospecifically bind" a second molecule if such binding exhibits the specificity and affinity of a receptor to its cognate binding ligand. B7-H4 molecules (e.g., B7-H4 proteins or fusion molecules, etc.) are said to be capable of "physiospecifically binding" to a target region or conformation ("epitope") of a receptor or of B7-H4 if such binding involves the B7-H4—Receptor recognition sites. A molecule may be capable of physiospecifically binding to more than one other molecule.

The molecules of the present invention have the ability to "deplete" (i.e., partially or completely decrease) the concentration of TAMs present within a tumor or block the activity of TAMs. Such depletion may relate to the absolute numbers of macrophages present within (or recruited to) a tumor, or it may relate to the concentration of active macrophages (i.e., the concentration of macrophages within or recruited to a tumor that possesses a capability to mediate a pro-angiogenic or pro-tumorigenic effect). Preferably, such depletion will provide at least a 10% change in a measurable immune system activity (for example, macrophage count, angiogenic potential, vascularization, macrophage viability, etc.), more preferably, at least a 50% change in such activity, or at least a 2-fold, 5-fold, 10-fold, or still more preferably, at least a 100-fold change in such activity.

As used herein the term "modulate" relates to a capacity to alter an effect or result. In particular, the invention relates to molecules (especially antibodies or their antigen-binding fragments that immunospecifically bind human B7-H4 or molecules that physiospecifically bind B7-H4 or its cognate receptor) that are capable of modulating the binding between B7-H4 and its cognate receptor and/or of modulating the signal transduction that occurs as a consequence of B7-H4—cognate receptor binding. Such modulation may be partial (i.e., attenuating, but not abolishing, an activity of B7-H4) or it may completely abolish such activity (e.g., neutralize the ability of B7-H4 to mediate signal transduction). Modulation may include internalization of the receptor following binding of the antibody or a reduction in expression of the receptor on the target cell. In a further embodiment, such modulation may enhance or otherwise agonize the interaction between B7-H4 and its cognate receptor, facilitating B7-H4—cognate receptor binding or signal transduction. In a still further embodiment, such modulation may alter the nature of the interaction between B7-H4 and its cognate receptor so as to alter the nature of the elicited signal transduction. For example, the molecules of the present invention can, by binding to B7-H4 alter the ability of such molecules to bind to other receptors and thereby alter their overall activity. Preferably, such modulation will provide at least a 10% change in a measurable immune system activity, more preferably, at least a 50% change in such activity, or at least a 2-fold, 5-fold, 10-fold, or still more preferably, at least a 100-fold change in such activity. Such modulation may therefore result in attenuating or in completely abolishing the ability of B7-H4 (for example, on tumor cells) to bind to its cognate receptor and therefore decrease (or prevent) the inhibition of the immune response mediated by B7-H4. As such, the present invention provides a treatment for cancer, infectious disease, and other diseases in which an enhanced immune response is desired. Alternatively, B7-H4-binding molecules may exert a modulating activity on tumor specific B7-H4 (as well as TAMs) that could impact the growth, development, viability, activity, etc. of the tumor directly.

As used herein, the "co-stimulatory" signals that are mediated by B7-H4 encompass positive co-stimulatory signals (e.g., signals that result in enhancing an activity) and negative co-stimulatory signals (e.g., signals that result in inhibiting an activity).

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region comprises a "hypervariable region" whose residues are responsible for antigen binding. The hypervariable region comprises amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.*

196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies of the invention). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that comprise the antibody's "variable region" antigen recognition site, and exhibit an ability to immunospecifically bind antigen. Such fragments include Fab', $F(ab')_2$, Fv, single chain (ScFv),and mutants thereof, naturally occurring variants, and fusion proteins comprising the antibody's "variable region" antigen recognition site and a heterologous protein (e.g., a toxin, an antigen recognition site for a different antigen, an enzyme, a receptor or receptor ligand, etc.). As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

Human, chimeric or humanized antibodies are particularly preferred for in vivo use in humans, however, murine antibodies or antibodies of other species may be advantageously employed for many uses (for example, in vitro or in situ detection assays, acute in vivo use, etc.). Completely human antibodies are particularly desirable for therapeutic treatment of human subjects.

Human antibodies can be made by a variety of methods known in the art including phage display methods using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a polypeptide of the invention. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

The invention particularly concerns "humanized antibodies" (see, e.g., European Patent Nos. EP 239,400, EP 592, 106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J.*

*Immunol.* 169:1119-1125; Caldas et al., 2000, *Protein Eng.* 13:353-360; Morea et al., 2000, *Methods* 20:267-79; Baca et al., 1997, *J. Biol. Chem.* 272:10678-10684; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-973; Jones et al., 1986, *Nature* 321:522-525; Reichmann et al., 1988, *Nature* 332: 323-329; and Presta, 1992, *Curr. Op. Struct. Biol.* 2:593-596). As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

In a particularly preferred embodiment, the antibodies and antigen-binding fragments of the present invention are selected for their ability to bind to TAMs and to thereby deplete such cells or modulate their activity.

The antibodies used in the methods of the present invention may be monospecific. Of particular interest are bispecific antibodies, trispecific antibodies or antibodies of greater multispecificity that exhibit specificity to different immune system targets in addition to B7-H4. For example, such antibodies may bind to both B7-H4 and to an antigen that is important for targeting the antibody to a particular cell type or tissue (for example, to an antigen associated with a cancer antigen of a tumor being treated). In another embodiment, such multispecific antibody binds to molecules (receptors or ligands) involved in alternative immunomodulatory pathways, such as B7-H1, PD-1, CTLA4, TIM3, TIM4, OX40, CD40, GITR, 4-1-BB, LIGHT or LAGS, in order to enhance the immunomodulatory effects and combine multiple mechanisms of action, such as ligand blocking and direct tumor targeting, in one molecule. For example, B7-H1 is also expressed on TAMs and a bi-specific antibody targeting both B7-H1 and B7-H4 would provide enhanced inhibition of TAM-mediated immune suppression, as well as enhanced inhibition of tumor-mediated B7-H1+ and B7-H4+ immune suppression. Furthermore, a bi-specific antibody targeting both PD-1 and B7-H4 would inhibit TAM-mediated immune suppression, inhibit tumor-mediated immune suppression (through both the B7-H4 and PD-1 pathways), reinvigorate exhausted T cells to enhance effector CTL recognition, and redirect/target effector CTL to tumor via a PD-1:B7-H4 "bridge." Furthermore, the multispecific antibody may bind to effecter molecules such as cytokines (e.g., IL-7, IL-15, IL-12, IL-4 TGF-beta, IL-10, IL-17, IFNg, Flt3, BLys) and chemokines (e.g., CCL21), which may be particularly relevant for modulating both acute and chronic immune responses. Likewise, an internalizing or toxin-conjugated antibody capable of binding B7-H4 may be employed to mediate the intracellular uptake and induced killing of tumor cells that express B7-H4.

Macrophages have been shown to contribute significantly to the initial steps of HIV infection (Carter, C. A. et al. (2008) "*Cell Biology Of HIV-1 Infection Of Macrophages*," Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS*," Lancet Infect. Dis. 6:794-804). Accordingly antibodies (particularly if conjugated to a toxin) that bind B7-H4 and a macrophage-specific marker such as CD14, CD68, CD163, TLR2 etc.) have utility in preventing HIV infection.

DNA sequences coding for preferred human acceptor famework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "*Structural Determinants In The Sequences Of Immunoglobulin Variable Domain*," *J. Mol. Biol.* 278: 457-479 for a listing of human framework regions).

A humanized or chimeric antibody of the invention may comprise substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, an antibody of the invention also comprises at least a portion of an immunoglobulin constant region (Fc), typically that of a human immunoglobulin. The constant domains of the antibodies of the invention may be selected with respect to the proposed function of the antibody, in particular the effector function which may be required. In some embodiments, the constant domains of the antibodies of the invention are (or comprise) human IgA, IgD, IgE, IgG or IgM domains. In a specific embodiment, human IgG constant domains, especially of the IgG1 and IgG3 isotypes are used, when the humanized antibodies of the invention is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the antibody of the invention is intended for therapeutic purposes and antibody effector function is not required. The invention encompasses Fc constant domains comprising one or more amino acid modifications which alter antibody effector functions such as those disclosed in U.S. Patent Application Publication Nos. 2005/0037000 and 2005/0064514.

In some embodiments, the antibody of the invention contains both the light chain as well as at least the variable domain of a heavy chain. In other embodiments, the antibody of the invention may further comprise one or more of the CH1, hinge, CH2, CH3, and CH4 regions of the heavy chain. The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain may be of the $IgG_2$ class. The antibody of the invention may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, *Nature* 332:323).

The antibodies of the present invention may be produced by any method known in the art useful for the production of polypeptides, e.g., in vitro synthesis, recombinant DNA production, and the like. Preferably, the humanized antibodies are produced by recombinant DNA technology. The antibodies of the invention may be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric antibodies of the invention may comprise the following: a) constructing, by conventional molecular biology methods, an expression vector that encodes and expresses an antibody heavy chain in which the CDRs and variable region of a murine anti-human B7-H4 monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human B7-H4 monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized antibodies of the invention may comprise the following: a) constructing, by conventional molecular biology methods, an expression vector that encodes and expresses an anti-human B7-H4 heavy chain in which the CDRs and a minimal portion of the variable region framework that are required to retain donor antibody binding specificity are derived from a non-human immunoglobulin, such as a murine anti-human B7-H4 monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as a murine anti-human B7-H4 monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant antibody of the invention may be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the above-described antibodies can be used to generate anti-idiotype antibodies using techniques well known to those skilled in the art (see, e.g., Greenspan, N. S. et al. (1989) "*Idiotypes: Structure And Immunogenicity,*" FASEB J. 7:437-444; and Nisinoff, A. (1991) "*Idiotypes: Concepts And Applications,*" J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman, U. et al. (1995) "*Phage Display Of Disulfide-Stabilized Fv Fragments,*" J. Immunol. Methods, 182:41-50, 1995; Ames, R. S. et al. (1995) "*Conversion Of Murine Fabs Isolated From A Combinatorial Phage Display Library To Full Length Immunoglobulins,*" J. Immunol. Methods, 184:177-186; Kettleborough, C. A. et al. (1994) "*Isolation Of Tumor Cell-Specific Single-Chain Fv From Immunized Mice Using Phage-Antibody Libraries And The Re-Construction Of Whole Antibodies From These Antibody Fragments,*" Eur. J. Immunol., 24:952-958, 1994; Persic, L. et al. (1997) "*An Integrated Vector System For The Eukaryotic Expression Of Antibodies Or Their Fragments After Selection From Phage Display Libraries,*" Gene, 187:9-18; Burton, D. R. et al. (1994) "*Human Antibodies From Combinatorial Libraries,*" Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art (such as those disclosed in PCT Publication WO 92/22324; Mullinax, R. L. et al. (1992) "*Expression Of A Heterodimeric Fab Antibody Protein In One Cloning Step,*" BioTechniques, 12(6):864-869; and Sawai et al. (1995) "*Direct Production Of The Fab Fragment Derived From The Sperm Immobilizing Antibody Using Polymerase Chain Reaction And cDNA Expression Vectors,*" Am. J. Reprod. Immunol. 34:26-34; and Better, M. et al. (1988) "*Escherichia coli Secretion Of An Active Chimeric Antibody Fragment,*" Science 240:1041-1043). Examples of techniques which can be used to produce single-chain Fvs and antibodies include those described in U.S. Pat. Nos. 4,946,778 and 5,258,498; Huston, J. S. et al. (1991) "*Protein Engineering Of Single-Chain Fv Analogs And Fusion Proteins,*" Methods in Enzymology 203:46-88; Shu, L. et al., "*Secretion Of A Single-Gene-Encoded Immunoglobulin From Myeloma Cells,*" Proc. Natl. Acad. Sci. (USA) 90:7995-7999; and Skerra. A. et al. (1988) "*Assembly Of A Functional Immunoglobulin Fv Fragment In Escherichia coli,*" Science 240:1038-1040.

Phage display technology can be used to increase the affinity of an antibody of the invention for B7-H4. This technique would be useful in obtaining high affinity antibodies that could be used in the combinatorial methods of the invention. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "*Antibody Engineering By Codon-Based Mutagenesis In A Filamentous Phage Vector System,*" J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "*Stepwise In Vitro Affinity Maturation Of Vitaxin, An Alphav Beta3-Specific Humanized Mab,*" Proc. Natl. Acad. Sci. (USA) 95(11):6037-6042; Yelton, D. E. et al. (1995) "*Affinity Maturation Of The BR96 Anti-Carcinoma Antibody By Codon-Based Mutagenesis,*" J. Immunol. 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarily Determining Regions In The Center Of The Antibody Binding Site,*" J. Mol. Biol. 263:551-567). The invention thus contemplates the use of random mutagenesis to identify improved CDRs. Phage display technology can be used to increase (or decrease) CDR affinity.

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV*-1 *gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "Affinity maturation of antibodies assisted by in silico modeling," Proc. Natl. Acad. Sci. (USA) 105(26): 9029-9034.

The invention particularly contemplates the production and use of "derivatives" of any of the above-described antibodies and their antigen-binding fragments.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. Such amino acids may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1 - - - 6) *Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277 (30): 26733-26740).

In some embodiments, a humanized antibody is a derivative. Such a humanized antibody comprises amino acid residue substitutions, deletions or additions in one or more non-human CDRs. The humanized antibody derivative may have substantially the same binding, stronger binding, or weaker binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Substitutions, additions or deletions in the derivatized antibodies may be in the Fc region of the antibody and may thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821. In some embodiments, the invention encompasses antibodies whose Fc region will have been deleted (for example, an Fab or F(ab)2, etc.) or modified so that the molecule will exhibit diminished or no Fc receptor (FcR) binding activity, or will exhibit enhanced antibody-dependent cell-mediated cytotoxicity (ADCC) or complement dependent cytotoxicity (CDC) activities. In some embodiments, the invention encompasses antibodies that have altered affinity for an activating FcγR, e.g., FcγRIIIA. Preferably such modifications also have an altered Fc-mediated effector function. Modifications that affect Fc-mediated effector function are well known in the art (see U.S. Pat. No. 6,194,551, and WO 00/42072). In one particular embodiment, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized antibodies of the invention may be engineered to increase biological half-lives (see, e.g. U.S. Pat. No. 6,277,375). For example, humanized antibodies of the invention may be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The antibodies of the invention may also be modified by the methods and coupling agents described by Davis et al. (See U.S. Pat. No. 4,179,337) in order to provide compositions that can be injected into the mammalian circulatory system with substantially no immunogenic response.

The invention encompasses modification of framework residues of the humanized antibodies of the invention. Residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) *"Reshaping Human Antibodies For Therapy,"* Nature 332:323-327).

The present invention also encompasses anti-human B7-H4 antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct, but may occur through linker sequences.

In one embodiment such heterologous molecules are polypeptides having at least 10, at least 20, at least 30, at least 40, at least 50, at least 60, at least 70, at least 80, at least 90 or at least 100 amino acids. Such heterologous molecules may alternatively be enzymes, hormones, cell surface receptors, drug moieties, such as: macrophage-specific targeting reagents (such as the intracellular carboxylesterase, hCE1 (Needham, L. A. et al. (2011) *"Drug Targeting To Monocytes And Macrophages Using Esterase-Sensitive Chemical Motif,"* J. Pharmacol. Exp. Ther. DOI:10.1124/jpet.111.183640), chitin and chitosan (Muzzarelli, R. A. (2010) *"Chitins And Chitosans As Immunoadjuvants And Non-Allergenic Drug Carriers,"* Mar Drugs 8(2):292-312), galactosylated low-density lipoprotein (Wu, F. et al. (009) *"Galactosylated LDL Nanoparticles: A Novel Targeting Delivery System To Deliver Antigen To Macrophages And Enhance Antigen Specific T Cell Responses,"* Molec. Pharm. 6(5):1506-1517), N-formyl-Met-Leu-Phe (fMLF), a macrophage-specific chemo-attractant (Wan, L. et al. (2008) *"Optimizing Size And Copy Number For PEG-Fmlf (N-Formyl-Methionyl-Leucyl-Phenylalanine) Nanocarrier Uptake By Macrophages,"* Bioconjug. Chem. 19(1):28-38), maleylated or mannosylated protein, such as maleylated albumin (Anatelli, F. et al. (2006) *"Macrophage-Targeted Photosensitizer Conjugate Delivered By Intratumoral Injection,"* Mol Pharm. 3(6):654-664; Bansal, P. et al. (1999) *"MHC Class I-Restricted Presentation Of Maleylated Protein Binding To Scavenger Receptors,"* J. Immunol. 162(8): 4430-4437); see also Mukhopadhyay, A. et al. (2003) *"Intracellular Delivery Of Drugs To Macrophages,"* Adv. Biochem. Eng. Biotechnol. 84:183-209), toxins (such as abrin, ricin A, pseudomonas exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF"), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

In another embodiment, the molecules of the present invention can be conjugated to a second antibody to form an antibody heteroconjugate as described by Segal in U.S. Pat. No. 4,676,980. Such heteroconjugate antibodies may additionally bind to haptens (such as fluorescein, etc.), or to cellular markers (e.g., 4-1-BB, B7-H1, PD-1, CD4, CD8, CD14, CD25, CD27, CD40, CD68, CD163, CTLA4, GITR, LAG-3, OX40, TIM3, TIM4, TLR2, LIGHT, etc.) or to cytokines (e.g., IL-4, IL-7, IL-10, IL-12, IL-15, IL-17, TGF-beta, IFNg, Flt3, BLys) or chemokines (e.g., CCL21), etc.

The Fc portion of the fusion protein may be varied by isotype or subclass, may be a chimeric or hybrid, and/or may be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al. (1997) "*Humanized Porcine VCAM-Specific Monoclonal Antibodies With Chimeric IgG2/G4 Constant Regions Block Human Leukocyte Binding To Porcine Endothelial Cells,*" Mol. Immun. 34(6):441-452, Swann, P. G. (2008) "*Considerations For The Development Of Therapeutic Monoclonal Antibodies,*" Curr. Opin. Immun. 20:493-499 (2008), and Presta, L. G. (2008) "*Molecular Engineering And Design Of Therapeutic Antibodies,*" Curr. Opin. Immun. 20:460-470. In some embodiments the Fc region is the native IgG1, IgG2, or IgG4 Fc region. In some embodiments the Fc region is a hybrid, for example a chimeric consisting of IgG2/IgG4 Fc constant regions. Modifications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region may include the entire hinge region, or less than the entire hinge region.

The therapeutic outcome in patients treated with rituximab (a chimeric mouse/human IgG1 monoclonal antibody against CD20) for non-Hodgkin's lymphoma or Waldenstrom's macroglobulinemia correlated with the individual's expression of allelic variants of Fcy receptors with distinct intrinsic affinities for the Fc domain of human IgG1. In particular, patients with high affinity alleles of the low affinity activating Fc receptor CD16A (FcγRIIIA) showed higher response rates and, in the cases of non-Hodgkin's lymphoma, improved progression-free survival. In another embodiment, the Fc domain may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduced binding to FcγR, which increases their half-life. Representative IgG2-4 hybrids and IgG4 mutants are described in Angal, S. et al. (1993) "*A Single Amino Acid Substitution Abolishes The Heterogeneity Of Chimeric Mouse/Human (Igg4) Antibody,*" Molec. Immunol. 30(1):105-108; Mueller, J. P. et al. (1997) "*Humanized Porcine VCAM-Specific Monoclonal Antibodies With Chimeric Igg2/G4 Constant Regions Block Human Leukocyte Binding To Porcine Endothelial Cells,*" Mol. Immun. 34(6): 441-452; and U.S. Pat. No. 6,982,323. In some embodiments the IgG1 and/or IgG2 domain is modified; for example, Angal, S. et al. describe IgG1 and IgG2 variants in which serine 241 is replaced with proline.

In a preferred embodiment, the Fc domain contains amino acid insertions, deletions or substitutions that enhance binding to CD16A. A large number of substitutions in the Fc domain of human IgG1 that increase binding to CD16A and reduce binding to CD32B are known in the art and are described in Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors,*" Cancer Res. 57(18):8882-8890. Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination. In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297Q substitution, as this mutation abolishes FcR binding.

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; and Thorpe et al. (1982) "*The Preparation And Cytotoxic Properties Of Antibody-Toxin Conjugates,*" Immunol. Rev. 62:119-158.

Any of the molecules of the present invention can be fused to marker sequences, such as a peptide, to facilitate purification. In preferred embodiments, the marker amino acid sequence is a hexa-histidine peptide, the hemagglutinin "HA" tag, which corresponds to an epitope derived from the influenza hemagglutinin protein (Wilson, I. A. et al. (1984) "*The Structure Of An Antigenic Determinant In A Protein,*" Cell, 37:767-778) and the "flag" tag (Knappik, A. et al. (1994) "*An Improved Affinity Tag Based On The FLAG Peptide For The Detection And Purification Of Recombinant Antibody Fragments,*" Biotechniques 17(4):754-761).

The present invention also encompasses antibodies or their antigen-binding fragments that are conjugated to a diagnostic or therapeutic agent, or another molecule for which serum half-life is desired to be increased. The antibodies can be used diagnostically (in vivo, in situ or in vitro) to, for example, monitor the development or progression of a disease, disorder or infection as part of a clinical testing procedure to, e.g., determine the efficacy of a given treatment regimen or to select patients more likely to respond to a particular therapy (such as those with high levels of infiltrating TAMs, and especially those expressing high levels of B7-H4).

In particular, most cancers in humans grow as solid tumors composed of cancer cells intertwined with a supporting group of structures (stroma) that are required for the survival, growth and progression of the tumor. The major components in tumor stroma are fibroblasts, neovasculature and immune cells, including macrophages. Such tumor-associated macrophages are not only one of the most important components of the tumor stroma, but comprise the antigen presenting cells (APC) that are critical for initiating and maintaining tumor-associated antigen (TAA)-specific T cell immunity.

Tumor environmental macrophages markedly outnumber the other APCs, such as dendritic cells (DCs), that are present within tumors, and represent a prominent subpopulation of APCs in solid tumors (Kryczek, I. et al. (2006) "*B7-H4 Expression Identifies A Novel Suppressive Macrophage Population In Human Ovarian Carcinoma*," J. Exper. Med. 203(4):871-881). Tumor environmental macrophages that are B7-H4$^+$ significantly suppress T cell activation. B7-H4$^-$ macrophages can be converted into B7-H4$^+$ macrophages by IL-10 and IL-6 in vitro (Kryczek, I. et al. (2006) "*Cutting Edge: Induction Of B7-H4 On APCs Through IL-10: Novel Suppressive Mode For Regulatory T Cells*," J. Immunol. 177(1):40-44). Since high levels of IL-10 and IL-6 are found in the ovarian tumor environment, the ability of such cytokines to induce B7-H4 expression is considered to be relevant to the increased suppression of T cell activation seen in aggressive tumors. Importantly, such suppressive activity can be reduced by GM-CSF or IL-4, two dendritic cell differentiation cytokines, which act to block B7-H4 expression. Such suppressive activity can also be reduced by blocking B7-H4 activity with the compositions of the present invention.

Although the phenotype and the role in tumor immunity played by dendritic cells has been investigated, such studies have not elucidated the roles played by B7-H4$^+$ and B7-H4$^-$ macrophages within the tumor environment of patients with cancer. The antibodies of the present invention have utility in elucidating the roles played by B7-H4$^+$ and B7-H4$^-$ macrophages and as a means for evaluating the clinical prognosis of tumors in patients (i.e., the extent of B7-H4$^+$ macrophages to total macrophages correlates with tumor aggressiveness and the severity of cancer). Such evaluations are particularly useful in conjunction with determinations of the extent of B7-H1$^+$ macrophages to total macrophages, since tumor B7-H1 expression and positive tumor B7-H4 expression are independently associated with death from cancer (Krambeck, A. E. et al. (2006) "*B7-H4 Expression In Renal Cell Carcinoma And Tumor Vasculature: Associations With Cancer Progression And Survival*," Proc. Natl. Acad. Sci. (U.S.A.) 103(2): 10391-10396).

Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the antibody to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho) indium ($^{115}$In, $^{113}$In, $^{112}$In, $^{111}$In), iodine ($^{131}$I, $^{125}$I, $^{123}$I, $^{121}$I), lanthanium ($^{140}$La) lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re) rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The molecules of the present invention may be attached to solid supports, which are particularly useful for immunoassays or purification of the target antigen or of other molecules that are capable of binding to target antigen that has been immobilized to the support via binding to an antibody or antigen-binding fragment of the present invention. Such solid supports include, but are not limited to, glass, cellulose, polyacrylamide, nylon, polystyrene, polyvinyl chloride or polypropylene.

The present invention additionally includes nucleic acid molecules (DNA or RNA) that encode any such antibodies, fusion proteins or fragments, as well as vector molecules (such as plasmids) that are capable of transmitting or of replicating such nucleic acid molecules. The nucleic acids can be single-stranded, double-stranded, may contain both single-stranded and double-stranded portions.

A. Preferred B7-H4 Modulators of the Present Invention

The B7-H4 modulators of the present invention comprise immunospecific or physiospecific B7-H4-binding molecules (and particularly, anti-B7-H4 antibodies and antigen-binding fragments) that possess sufficient ability to modulate an activity of B7-H4 arrayed on the surface of a macrophage (especially when such B7-H4 is expressed at an endogenous concentration). The term "endogenous concentration" refers to the level at which a molecule is natively expressed (i.e., in the absence of expression vectors or recombinant promoters) by a cell (which may be a normal, cancer or infected cell).

In one embodiment, such modulation will be caused by the binding of such modulators to B7-H4 (preferably as endogenously expressed and arrayed). In an alternative embodiment, such modulation will comprise enhancing or otherwise facilitating the binding of endogenously expressed and arrayed B7-H4

(1) Preferred Anti-Human B7-H4 Antibodies and Their CDRs

In accordance with the present invention, such molecules can be produced by screening hybridoma lines for those that produce antibody that are immunospecific for human B7-H4, and then optionally screening amongst such lines for those exhibiting modulating activity (e.g., neutralizing activity, agonizing activity, altered signal transducing activity, etc.). The invention particularly provides anti-human B7-H4 clones: 2D1, 2E11 and 2H9.

The antibodies expressed by the anti-human B7-H4 clones were sequenced to reveal their variable domains. Several clones were found to have variant ("Var") light or heavy chains. CDR sequences are shown in bold and underlined:

```
Anti-Human B7-H4 Clone 2D1
Light Chain Variable Region:
                                            (SEQ ID NO: 3)
DVVMTQTPLS LPVSLGDQAS ISCRSSHSLV HSNGNTYLHW

YLQKPGQSPN LLIYIVSNRF SGVPDRFSGS GSGTDFTLKI

SRVEAEDLGV YFCSQSTHVP PTFGAGTKLE LK
```

```
Heavy Chain Variable Region:
                                            (SEQ ID NO: 8)
EVQLVESGGN LVKPGGSLKL SCAASGFTFS NSAMSWVRQT

PEKRLEWVAT ISDGGRYTYY PDNVKGRFTI SRDNAKNNLY

LQMSHLKSED TALYYCARDR PHWYFDVWGT GATVTVSS
```

(2) Consensus CDRs of the Anti-Human B7-H4 Antibodies of the Present Invention

Analyses of the CDRs of the identified antibodies were conducted in order to identify consensus CDR sequences and likely variant CDR sequences that would provide similar binding attributes. Such variant CDRs were computed using Blosum62.iij analysis according to Table 1. Table 1 presents the Blosum62.iij substitution scores. The higher the score the more conservative the substitution and thus the more likely the substitution will not affect function.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | -1 | -2 | -2 | 0 | -1 | -1 | 0 | -2 | -1 | -1 | -1 | -1 | -2 | -1 | +1 | 0 | -3 | -2 | 0 |
| R | -1 | +5 | 0 | -2 | -3 | +1 | 0 | -2 | 0 | -3 | -2 | +2 | -1 | -3 | -2 | -1 | -1 | -3 | -2 | -3 |
| N | -2 | 0 | +6 | +1 | -3 | 0 | 0 | 0 | +1 | -3 | -3 | 0 | -2 | -3 | -2 | +1 | 0 | -4 | -2 | -3 |
| D | -2 | -2 | +1 | +6 | -3 | 0 | +2 | -1 | -1 | -3 | -4 | -1 | -3 | -3 | -1 | 0 | -1 | -4 | -3 | -3 |
| C | 0 | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0 | 0 | -3 | +5 | +2 | -2 | 0 | -3 | -2 | +1 | 0 | -3 | -1 | 0 | -1 | -2 | -1 | -2 |
| E | -1 | 0 | 0 | +2 | -4 | +2 | +5 | -2 | 0 | -3 | -3 | +1 | -2 | -3 | -1 | 0 | -1 | -3 | -2 | -2 |
| G | 0 | -2 | 0 | -1 | -3 | -2 | -2 | +6 | -2 | -4 | -4 | -2 | -3 | -3 | -2 | 0 | -2 | -2 | -3 | -3 |
| H | -2 | 0 | +1 | -1 | -3 | 0 | 0 | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0 | -3 | -2 | -1 | -3 | -1 | +3 |
| L | -1 | -2 | -3 | -4 | -1 | -2 | -3 | -4 | -3 | +2 | +4 | -2 | +2 | 0 | -3 | -2 | -1 | -2 | -1 | +1 |
| K | -1 | +2 | 0 | -1 | -3 | +1 | +1 | -2 | -1 | -3 | -2 | +5 | -1 | -3 | -1 | 0 | -1 | -3 | -2 | -2 |
| M | -1 | -1 | -2 | -3 | -1 | 0 | -2 | -3 | -2 | +1 | +2 | -1 | +5 | 0 | -2 | -1 | -1 | -1 | -1 | +1 |
| F | -2 | -3 | -3 | -3 | -2 | -3 | -3 | -3 | -1 | 0 | 0 | -3 | 0 | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0 | -1 | 0 | 0 | 0 | -1 | -2 | -2 | 0 | -1 | -2 | -1 | +4 | +1 | -3 | -2 | -2 |
| T | 0 | -1 | 0 | -1 | -1 | -1 | -1 | -2 | -2 | -1 | -1 | -1 | -1 | -2 | -1 | +1 | +5 | -2 | -2 | 0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0 | -3 | -3 | -3 | -1 | -2 | -2 | -3 | -3 | +3 | +1 | -2 | +1 | -1 | -2 | -2 | 0 | -3 | -1 | +4 |

```
Heavy Chain Variable Region:
                                            (SEQ ID NO: 4)
EVQLVESGGG LVKPGGSLKL SCAASGFTFN SHGMSWVRQT

PEKRLDWVAT ISDGGTYTYY PVNVKGRFTI SRDNAKNNLY

LQMSHLKSED TAMYYCARDG GGGAYWGQGT LVTVSA

Anti-Human B7-H4 Clone 2E11
Light Chain Variable Region:
                                            (SEQ ID NO: 5)
DIVMSQSPSS LAVSVGEKVT VSCKSSQSLL YSTNQRTYLA

WFQQKPGQSP KLLIYWASTR ESGVPDRFTG SGSGTDFTLT

ISSVKAEDLA VYYCQQYYNY PLTFGTGTKL ELK

Heavy Chain Variable Region:
                                            (SEQ ID NO: 6)
EVKLVESEGG LVQPGSSMKL SCTASGFKFT DYYMAWVRQV

PEKGLEWVAN INYDGSSTYY LDSLKSRFII SRDNAKNILY

LQMNSLKSED TATYYCARKG YFDYWGQGTT LTVSS

Anti-Human B7-H4 Clone 2H9
Light Chain Variable Region:
                                            (SEQ ID NO: 7)
DIVLTQSPAS LAVSLGQRAT ISCRASESID NYGISFMHWY

QQKPGQPPKL LIYRASNLES GIPARFSGSG SRTDFTLTIN

PVETDDVATY FCQQSDEGRT FGGGTKLEIK
```

The present invention permits the formation of novel antibodies and antigen-binding fragments having 1, 2, 3, 4, 5 or 6 variant CDRs. Because the methods of the present invention have identified a substantial number of distinct CDRs, the invention permits a recognition of CDR residues that are likely to be required in any variant of a particular identified CDR. Such residues are shown in boldface in Table 2 and Table 3. For those residues that are found to vary among the compared CDRs, the substitution scores of Table 1 provide a means for determining the identities of permitted substitutions. For example, if a particular residue of a particular CDR is found to vary as R or S, then since R and S have a substitution score of −1, any substitution of R or S having a substitution score of −1 or greater are as likely as the observed variants (R or S) (or are more likely than R or S) to create a variant CDR having binding attributes that are sufficiently similar to those of the particular CDR to permit the variant CDR to be employed in lieu thereof so as to form a functional anti-B7-H4 antibody or antigen-binding fragment. For each position, the selection of a residue having a higher substitution score is preferred over the selection of a residue having a lower substitution score.

Table 2 presents an analysis of the light chain CDRs of the anti-B7-H4 antibodies and provides the consensus sequence of the observed and preferred variant light chain anti-B7-H4 CDRs of the present invention.

TABLE 2

Anti-B7-H4 Light Chain CDRs

| Antibody | Sequence | SEQ ID NO |
|---|---|---|
| *Light Chain CDR1* | | |
| 2D1 | R S SH SL V H S   N G N T Y L H | 9 |
| 2E11 | K S SQ SL L Y S T N Q R T Y L A | 10 |
| 2H9 | R A SE SI D N   Y G I S F M H | 11 |
| Light Chain CDR1 Consensus Sequence: | $X_1X_2\mathbf{S}X_3\mathbf{S}X_4X_5X_6X_7X_8X_9X_{10}X_{11}X_{12}X_{13}X_{14}X_{15}$ | 12 |

$X_1$ is R or K or a substitution having an equal or greater substitution score (i.e., ≥ +2): R or K
$X_2$ is S or A or a substitution having an equal or greater substitution score (i.e., ≥ +1): S or A
$X_3$ is Q, H or E or a substitution having an equal or greater substitution score (i.e., ≥ 0): R, N, Q, E or H
$X_4$ is L or I or a substitution having an equal or greater substitution score (i.e., ≥ +2): L or I
$X_5$ is V, L or D or a substitution having an equal or greater substitution score (i.e., ≥ -4): any amino acid
$X_6$ is H, Y or N or a substitution having an equal or greater substitution score (i.e., ≥ -2): A, R, N, Q,E,H,K,M, S,T or Y
$X_7$ is absent or is S
$X_8$ is absent or is T
$X_9$ is N or Y or a substitution having an equal or greater substitution score (i.e., ≥ -2): A, R, N, Q, E, H, K, M, S, T or Y
$X_{10}$ is G or Q or a substitution having an equal or greater substitution score (i.e., ≥ -2): A, R, N, D, Q, E, G, H, K, P, S, T or W
$X_{11}$ is N, R or I or a substitution having an equal or greater substitution score (i.e., ≥ -3): A, R, N, D, C, Q, E, H, I, L, K, M, F, P, S, T, Y or V
$X_{12}$ T or S or a substitution having an equal or greater substitution score (i.e., ≥ +1): S or T
$X_{13}$ is F or Y or a substitution having an equal or greater substitution score (i.e., ≥ +3): F or Y
$X_{14}$ is L or M or a substitution having an equal or greater substitution score (i.e., ≥ +2): L or M
$X_{15}$ is H or A or a substitution having an equal or greater substitution score (i.e., ≥ -2): A, R, N, D, Q, E, G, H, K, M, F, P, S, T, W or Y

| | Light Chain CDR2 | |
|---|---|---|
| 2D1 | I V SN R F S | 13 |
| 2E11 | W A ST R E S | 14 |
| 2H9 | R A SN L E S | 15 |
| Light Chain CDR2 Consensus Sequence: | $x_1x_2\mathbf{S}X_3X_4X_5\mathbf{S}$ | 16 |

$X_1$ is I, W or R or a substitution having an equal or greater substitution score (i.e., ≥ -3): A, R, C, Q, E, H, I, L, K, M, F, S, T, W, Y or V
$X_2$ is V or A or a substitution having an equal or greater substitution score (i.e., ≥ 0): A or V
$X_3$ is N or T or a substitution having an equal or greater substitution score (i.e., ≥ 0): N, S or T
$X_4$ is R or L or a substitution having an equal or greater substitution score (i.e., ≥ -2): A, R, Q, L, K, M, S, T or Y
$X_5$ is F or E or a substitution having an equal or greater substitution score (i.e., ≥ -3): A, R, N, D, Q, E, G, H, I, K, M, F, S, T, W, Y or V

TABLE 2-continued

Anti-B7-H4 Light Chain CDRs

| Antibody | Sequence | SEQ ID NO |
|---|---|---|
| *Light Chain CDR3* | | |
| 2D1 | S QS T H V P P T | 17 |
| 2E11 | Q QY Y N Y P L T | 18 |
| 2H9 | Q QS D E G   R T | 19 |
| Light Chain CDR3 Consensus Sequence: | $X_1\mathbf{Q}X_2X_3X_4X_5X_6X_7\mathbf{T}$ | 20 |

$X_1$ is S or Q or a substitution having an equal or greater substitution score (i.e., ≥ 0): N, D, Q, E, K or S
$X_2$ is S or Y or a substitution having an equal or greater substitution score (i.e., ≥ -2): A, R, N, C, Q, E, H, I, L, K, M, F, S, T, Y or V
$X_3$ is T, Y or D or a substitution having an equal or greater substitution score (i.e., ≥ -3): A, R, N, D, C, Q, E, G, H, I, K, M, F, P, S, T, Y or V
$X_4$ is H, N or E or a substitution having an equal or greater substitution score (i.e., ≥ 0): R, N, Q, E or H
$X_5$ is V, Y or G or a substitution having an equal or greater substitution score (i.e., ≥ -3): A, R, N, D, C, Q, E, G, H, K, M, F, P, S, T, W, Y or V
$X_6$ is P or is absent
$X_7$ is P, L or R or a substitution having an equal or greater substitution score (i.e., ≥ -3): A, R, N, D, C, Q, E, H, I, L, K, M, P, S, T, Y or V Table 3 presents an analysis of the heavy chain CDRs of the anti-B7-H4 antibodies and provides the consensus sequence of the observed and preferred variant anti-B7-H4 heavy chain CDRs of the present invention.

TABLE 3

Anti-B7-H4 Heavy Chain CDRs

| Antibody | Sequence | SEQ ID NO |
|---|---|---|
| *Heavy Chain CDR1* | | |
| 2D1 | GFT FN S H G MS | 21 |
| 2E11 | GFK FT D Y Y MA | 22 |
| 2H9 | GFT FS N S A MS | 23 |
| Heavy Chain CDR1 Consensus Sequence: | $\mathbf{GF}X_1\mathbf{F}X_2X_3X_4X_5\mathbf{M}X_6$ | 24 |

$X_1$ is T or K or a substitution having an equal or greater substitution score (i.e., ≥ -1): A, R, N, D, Q, E, K, M, P, S or T
$X_2$ is T, N or S or a substitution having an equal or greater substitution score (i.e., ≥ 0): N, S or T
$X_3$ is D, S or N or a substitution having an equal or greater substitution score (i.e.,≥ +1): N, D, H or S TABLE 3-continued Anti-B7-H4 Heavy Chain CDRs

| Antibody | Sequence | SEQ ID NO |
|---|---|---|
| $X_4$ is Y, H or S or a substitution having an equal or greater substitution score (i.e., ≥ -2): A, R, N, Q, E, H, K, M, F, S, T or Y $X_5$ is Y, A or G or a substitution having an equal or greater substitution score (i.e., ≥ -3): A, R, N, D, C, Q, E, G, H, K, M, F, P, S, T, W, Y or V $X_6$ is S or A or a substitution having an equal or greater substitution score (i.e., ≥ +1): S or A | | |
| Heavy Chain CDR2 | | |
| 2D1 | T IS D G GT Y TYYP V N V KG | 25 |
| 2E11 | N IN Y D GS S TYYL D S L KS | 26 |
| 2H9 | T IS D G GR Y TYYP D N V KG | 27 |
| Heavy Chain CDR2 Consensus Sequence: | $X_1IX_2X_3X_4GX_5X_6TYYX_7X_8X_9X_{10}KX_{11}$ | 28 |

$X_1$ is T or N or a substitution having an equal or greater substitution score (i.e., ≥ 0): N, S or T
$X_2$ is N or S or a substitution having an equal or greater substitution score (i.e., ≥ +1): N or S
$X_3$ is D or Y or a substitution having an equal or greater substitution score (i.e., ≥ -3): A, R, N, D, C, Q, E, G, H, I, L, K, M, F, P, S, T, Y or V
$X_4$ is G or D or a substitution having an equal or greater substitution score (i.e., ≥ -1): N, D, G or S
$X_5$ is T, S or R or a substitution having an equal or greater substitution score (i.e., ≥ -1): A, R, N, Q, E, K, M, S or T
$X_6$ is Y or S or a substitution having an equal or greater substitution score (i.e., ≥ -2): A, R, N, C, Q, E, H, I, L, K, M, F, S, T, Y or V
$X_7$ is P or L or a substitution having an equal or greater substitution score (i.e., ≥ -3): A, R, N, C, Q, E, H, I, L, K, M, P, S, T, Y or V
$X_8$ is V or D or a substitution having an equal or greater substitution score (i.e., ≥ -3): A, R, N, D, C, Q, E, G, H, I, K, M, F, P, S, T, Y or V
$X_9$ is S or N or a substitution having an equal or greater substitution score (i.e., ≥ +1): S or N
$X_{10}$ is V or L or a substitution having an equal or greater substitution score (i.e., ≥ +1): I, L, M or V
$X_{11}$ is G or S or a substitution having an equal or greater substitution score (i.e., ≥ 0): A, N, G or S

| Heavy Chain CDR3 | | |
|---|---|---|
| 2D1 | D G G G G    A Y | 29 |
| 2E11 | K G Y F    D Y | 30 |
| 2H9 | D R P H W Y F D V | 31 |
| Heavy Chain CDR3 Consensus Sequence | $X_1X_2X_3X_4X_5X_6X_7X_8X_9$ | 32 |

$X_1$ is D or K or a substitution having an equal or greater substitution score (i.e., ≥ -1): N, D, Q, E, H, K, P, S or T
$X_2$ is G or R or a substitution having an equal or greater substitution score (i.e., ≥ -2): A, R, N, D, Q, E, G, H, K, P, S or T
$X_3$ is G, Y or P or a substitution having an equal or greater substitution score (i.e., ≥ -3): A, R, N, D, C, Q, E, G, H, K, M, P, S, T, Y or V
$X_4$ is G, F or H or a substitution having an equal or greater substitution score (i.e., ≥ -3): A, R, TABLE 3-continued Anti-B7-H4 Heavy Chain CDRs

| Antibody | Sequence | SEQ ID NO |
|---|---|---|
| N, D, C, Q, E, G, H, K, M, F, S, T, W, Y or V $X_5$ is absent or is D or K or a substitution having an equal or greater substitution score (i.e., ≥ -1): N, D, Q, E, H, K, P, S or T $X_6$ is absent or Y $X_7$ is absent or F $X_8$ is D or A or a substitution having an equal or greater substitution score (i.e., ≥ -2): A, R, N, D, Q, E, G, H, K, P, S or T $X_9$ is Y or V or a substitution having an equal or greater substitution score (i.e., ≥ -1): I, L, M, F, Y or V | | |

Thus, in addition to antibodies and antigen-binding fragments thereof that possess the CDRs of the anti-B7-H4 antibodies: 2D1, 2E11 and 2H9, the invention additionally provides antibodies and antigen-binding fragments thereof that possess CDRs having the above-described light and/or heavy chain consensus sequences.

The present invention encompasses antibodies or fragments thereof comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the mouse monoclonal antibody produced by any of the above clones, and which exhibit immunospecific binding to B7-H4. The present invention further encompasses antibodies or fragments thereof that comprise a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the above-listed clones and which exhibit immunospecific binding to B7-H4. The determination of percent identity of two amino acid sequences can be determined by BLAST protein comparison. In a preferred embodiment, the antibody is a humanized immunoglobulin molecule (e.g., an antibody, diabody, fusion protein, etc.) that comprises one, two or three light chain CDRs and one, two or three heavy chain CDRs (most preferably three light chain CDRs and three heavy chain CDRs), wherein the light chain CDRs include:
  (1) the light chain CDR1
  (2) the light chain CDR2
  (3) the light chain CDR3
  (4) the light chain CDR1 and the light chain CDR2
  (5) the light chain CDR1 and the light chain CDR3
  (6) the light chain CDR2 and the light chain CDR3 or
  (7) the light chain CDR1, the light chain CDR2 and the light chain CDR3
of any of the above-described anti-B7-H4 antibodies or of the above-identified consensus light chain sequences. In an alternative preferred embodiment, the humanized immunoglobulin molecule comprises one, two or three light chain CDRs and one, two or three heavy chain CDRs (most preferably three light chain CDRs and three heavy chain CDRs), wherein the heavy chain CDRs include:
  (1) the heavy chain CDR1
  (2) the heavy chain CDR2
  (3) the heavy chain CDR3
  (4) the heavy chain CDR1 and the heavy chain CDR2

(5) the heavy chain CDR1 and the heavy chain CDR3
(6) the heavy chain CDR2 and the heavy chain CDR3
or
(7) the heavy chain CDR1, the heavy chain CDR2 and the heavy chain CDR3 of any of the above-described anti-B7-H4 antibodies or the above-identified consensus heavy chain sequences. In a particularly preferred embodiment, the antibody is a humanized immunoglobulin molecule that comprises one, two or three light chain CDRs and one, two or three heavy chain CDRs (most preferably three light chain CDRs and three heavy chain CDRs), wherein the light chain CDRs include:
(1) the light chain CDR1
(2) the light chain CDR2
(3) the light chain CDR3
(4) the light chain CDR1 and the light chain CDR2
(5) the light chain CDR1 and the light chain CDR3
(6) the light chain CDR2 and the light chain CDR3
or
(7) the light chain CDR1, the light chain CDR2 and the light chain CDR3 of any of the above described antibodies or the above-identified consensus light chain sequences, and wherein the heavy chain CDRs include:
(1) the heavy chain CDR1
(2) the heavy chain CDR2
(3) the heavy chain CDR3
(4) the heavy chain CDR1 and the heavy chain CDR2
(5) the heavy chain CDR1 and the heavy chain CDR3
(6) the heavy chain CDR2 and the heavy chain CDR3
or
(7) the heavy light chain CDR1, the heavy light chain CDR2 and the heavy chain CDR3 of any of the above described antibodies or the above-identified consensus light chain sequences.

In a specific embodiment, an antibody or an antigen-binding fragment thereof of the present invention will comprise one, two, three, four, five, or more preferably, all 6 CDRs of the above-described preferred antibodies and will exhibit the ability to bind to human B7-H4.

B. Therapeutic and Prophylactic Uses of the Preferred Compositions of the Present Invention The invention particularly concerns antibodies that immunospecifically bind to B7-H4 in a recipient subject. As used herein, a "subject" is preferably a mammal such as a non-primate (e.g., cows, pigs, horses, cats, dogs, rats, etc.) or a primate (e.g., monkey and human), and most preferably a human. The invention thus particularly relates to humanized antibodies, and antigen-binding fragments thereof, that immunospecifically bind to human B7-H4.

In a preferred embodiment, such molecules are capable of depleting TAMs in a recipient human or in human tissue (in situ or ex vivo) or of modulating the activity of such TAMs. Depletion of TAMs or a beneficial reduction in B7-H4 levels can be monitored by IHC of tumor tissues using the anti-B7-H4 antibody of the invention or another TAM-specific marker, or a reduction in B7-H4 mRNA levels by PCR, in-situ hybridization or another other method known to one skilled in the art. Patients likely to benefit from treatment with an anti-B7-H4 antibody of the invention will express the target B7-H4 protein, either on tumor or TAMs, and this can be assessed by IHC of tumor samples, FACs, in-situ hybridization or another other method known to one skilled in the art.

As used herein, the terms "treat," "treating," "treatment" and "therapeutic use" refer to the elimination, reduction or amelioration of one or more symptoms of a disease or disorder exacerbated by the interactions of B7-H4 with its receptor(s), or by the expression of B7-H4 or its presence arrayed on the surface of a cell. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means that amount of therapeutic agent alone, or in combination with other therapies, that provides a therapeutic benefit in the treatment or management of a disease, e.g., sufficient to enhance the therapeutic efficacy of a therapeutic antibody sufficient to treat or manage a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the Physician's Desk Reference ($56^{th}$ Ed., 2002).

1. Uses of Up-Modulators of the Immune System

In a preferred embodiment, such antibodies and fragments bind to B7-H4 to disrupt binding between B7-H4 and its receptor(s) (for example, by binding at one or more sites proximal to and disruptive of the binding site of B7-H4 and its receptor, or at a region whose conformation is disrupted by such binding and thus becomes impaired in its ability to bind to receptor, etc.). As discussed above, interactions between B7-H4 and its receptor inhibit the proliferation of T cells and reduce inflammation, including the production of multiple cytokines (Zang, X. et al. (2003) *B7x: A Widely Expressed B7 Family Member That Inhibits T Cell Activation*," Proc. Natl. Acad. Sci. (USA) 100:10388-10392; Prasad, D. V. et al. (2003) *B7S1, A Novel B7 Family Member That Negatively Regulates T Cell Activation*," Immunity 18:863-873). Thus, in a preferred embodiment, the administration of the molecules of the present invention to a subject up-modulates immune responses of the subject by antagonizing normal B7-H4 binding to its receptor.

Up-modulation of the immune system is particularly desirable in the treatment of cancers and chronic infections, and thus the present invention has utility in the treatment of such disorders. B7-H4 is over-expressed upon HIV infection (Carter, C. A. et al. (2008) "*Cell Biology Of HIV-1 Infection Of Macrophages,*" Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS,*" Lancet Infect. Dis. 6:794-804). Hence, the anti-B7-H4 antibodies of the present invention have particular utility as therapeutics for HIV infection and AIDS treatment. As used herein, the term "cancer" refers to a neoplasm or tumor resulting from abnormal uncontrolled growth of cells. As used herein, cancer explicitly includes, leukemias and lymphomas. The term refers to a disease involving cells that have the potential to metastasize to distal sites and exhibit phenotypic traits that differ from those of non-cancer cells, for example, formation of colonies in a three-dimensional substrate such as soft agar or the formation of tubular networks or weblike matrices in a three-dimensional basement membrane or extracellular matrix preparation. Non-cancer cells do not form colonies in soft agar and form distinct sphere-like structures in three-dimensional basement membrane or extracellular matrix preparations.

Cancers and related disorders that can be treated or prevented by methods and compositions of the present invention include, but are not limited to, the following: leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

Similar to its application to tumors as discussed above, the antibodies and antigen-binding fragments of the present invention can be used alone, or as an adjuvant, in combination with vaccines or with antimibrobial agents, to stimulate the immune response against toxins or self-antigens or against pathogens (e.g., viruses, such as HIV, HTLV, hepatitis virus, influenza virus, respiratory syncytial virus, vaccinia virus, rabies virus; bacteria, such as those of *Mycobacteria, Staphylococci, Streptococci, Pneumonococci, Meningococci, Conococci, Klebsiella, Proteus, Serratia, Pseudomonas, Legionella, Corynebacteria, Salmonella, Vibrio, Clostridia, Bacilli, Pasteurella, Leptospirosis, Bordatella,* and particularly such pathogens associated with cholera, tetanus, botulism, anthrax, plague, and Lyme disease; or fungal or parasitic pathogens, such as *Candida (albicans, krusei, glabrata, tropicalis,* etc.), *Cryptococcus, Aspergillus (fumigatus, niger,* etc.), Genus *Mucorales (mucor, absidia, rhizophus), Sporothrix (schenkii), Blastomyces (dermatitidis), Paracoccidioides (brasiliensis), Coccidioides (immitis)* and *Histoplasma (capsulatum), Entamoeba, histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Toxoplasma gondi,* etc.)., *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia,* or *Trypanosoma,* etc. Thus, the antibodies and antigen-binding fragments of the present invention have utility in the treatment of infectious disease.

As indicated above, a particularly preferred use of the antibodies and antigen-binding fragments of the present invention is to bind to and preferably block TAMs so as to modulate their immune suppressive activity or deplete their concentration in a tumor or in peripheral blood. In one embodiment such modulation or depletion is accomplished using anti-B7-H4 antibodies that bind to a site so as to impair or disrupt normal B7-H4 function. As a consequence of such disruption, TAMs activity is decreased (modulated), and/or the actual or effective (functional) concentration of macrophages in the tumor is depleted. Alternatively, such modulation or depletion is accomplished using anti-B7-H4 antibodies that are conjugated to a toxin, such that their binding to a TAM leads to the death of the macrophage. Preferably, in either embodiment, the sequence of the Fc region of the antibody will have been deleted (for example, an Fab or F(ab)$_2$, etc.) or modified so that the molecule will exhibit diminished or no Fc receptor (FcR) binding activity, or will exhibit enhanced antibody-dependent cell-mediated cytotoxicity (ADCC) or complement dependent cytotoxicity (CDC) activities. Antibodies having diminished or no Fc receptor binding activity will work as a blocker that prevent B7-H4 on the TAMs from interacting with inhibitory Fc receptor(s) on T cells in the tumor microenvironment. On the other hand, the use of antibodies having Fc regions that exhibit enhanced induction of ADCC or CDC cause depletion of the TAMs depleting B7-H4.

2. Uses of Down-Modulators of the Immune System

In an alternative embodiment, agonist antibodies that bind directly to the receptor and result in signal transduction associated with binding of endogenous B7-H4 (or other ligands) or enhance binding between such antibodies and such receptor/ligand and have utility as agonists of B7-H4 signaling in order to inhibit immune responses. Preferably, such molecules will immunospecifically bind to the B7-H4 binding molecules of the present invention. Such molecules thus have utility in the treatment of inflammation and autoimmune disease. Similarly, the anti-B7-H4 antibodies of the present invention may be employed to produce anti-idiotypic peptides or antibodies (Wallmann, J. et al. (2010) "*Anti-Ids in Allergy: Timeliness of a Classic Concept*," World Allergy Organiz. J. 3(6):195-201; Nardi, M. et al. (2000) "*Antiidiotype Antibody Against Platelet Anti-GpIIIa Contributes To The Regulation Of Thrombocytopenia In HIV-1-ITP Patients,*" J. Exp. Med. 191(12):2093-2100) or mimetics (Zang, Y. C. et al. (2003) "*Human Anti-Idiotypic T Cells Induced By TCR Peptides Corresponding To A Common CDR3 Sequence Motif In Myelin Basic Protein-Reactive T Cells,*" Int. Immunol. 15(9):1073-1080; Loiarro, M. et al. (Epub 2010 Apr. 8) "*Targeting TLR/IL-JR Signalling In Human Diseases,*" Mediators Inflamm. 2010:674363) of B7-H4. Such molecules serve as surrogates for B7-H4, and thus their administration to a subject down-modulates the immune system of such subject by mimicking or facilitating B7-H4 binding.

Down-modulation of the immune system is desirable in the treatment of inflammatory and auto-immune diseases, a response to transplantation rejection, graft vs host disease or host vs graft disease. Examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal aristis/giant cell arteritis, ulcerative colitis, uveitis, vasculitides such as dermatitis herpetiformis vasculitis, vitiligo, and Wegener's granulomatosis.

Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacterial infections.

Thus, the antibodies and antigen-binding fragments of the present invention have utility in the treatment of inflammatory and auto-immune diseases, a response to transplantation rejection, graft vs host and host vs graft diseases.

C. Methods of Administration

Various delivery systems are known and can be used to administer the therapeutic or prophylactic compositions of the present invention, e.g., encapsulation in liposomes, microparticles, microcapsules, recombinant cells capable of expressing the antibody or fusion protein, receptor-mediated endocytosis (see, e.g., Wu and Wu, 1987, J. Biol. Chem. 262:4429-4432), construction of a nucleic acid as part of a retroviral or other vector, etc.

Methods of administering an immunoglobulin molecule of the invention (e.g., an antibody, diabody, fusion protein, etc.) include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering an antibody of the invention, care must be taken to use materials to which the antibody or the fusion protein does not absorb.

In some embodiments, the humanized or chimeric antibodies of the invention are formulated in liposomes for targeted delivery of the antibodies of the invention. Liposomes are vesicles comprised of concentrically ordered phopsholipid bilayers which encapsulate an aqueous phase. Liposomes typically comprise various types of lipids, phospholipids, and/or surfactants. The components of liposomes are arranged in a bilayer configuration, similar to the lipid arrangement of biological membranes. Liposomes are particularly preferred delivery vehicles due, in part, to their biocompatibility, low immunogenicity, and low toxicity. Methods for preparation of liposomes are known in the art and are encompassed within the invention, see, e.g., Epstein et al., 1985, Proc. Natl. Acad. Sci. USA, 82: 3688; Hwang et al., 1980 Proc. Natl. Acad. Sci. USA, 77: 4030-4; U.S. Pat. Nos. 4,485,045 and 4,544,545.

The invention also encompasses methods of preparing liposomes with a prolonged serum half-life, i.e., enhanced circulation time, such as those disclosed in U.S. Pat. No. 5,013,556. Preferred liposomes used in the methods of the invention are not rapidly cleared from circulation, i.e., are not taken up into the mononuclear phagocyte system (MPS). The invention encompasses sterically stabilized liposomes which are prepared using common methods known to one skilled in the art. Although not intending to be bound by a particular mechanism of action, sterically stabilized liposomes contain lipid components with bulky and highly flexible hydrophilic moieties, which reduces the unwanted reaction of liposomes with serum proteins, reduces oposonization with serum components and reduces recognition by MPS. Sterically stabilized liposomes are preferably prepared using polyethylene glycol. For preparation of liposomes and sterically stabilized liposome, see, e.g., Bendas et al., 2001 BioDrugs, 15(4): 215-224; Allen et al., 1987 FEBS Lett. 223: 42-6; Klibanov et al., 1990 FEBS Lett., 268: 235-7; Blum et al., 1990, Biochim. Biophys. Acta., 1029: 91-7; Torchilin et al., 1996, J. Liposome Res. 6: 99-116; Litzinger et al., 1994, Biochim. Biophys. Acta, 1190: 99-107; Maruyama et al., 1991, Chem. Pharm. Bull., 39: 1620-2; Klibanov et al., 1991, Biochim Biophys Acta, 1062; 142-8; Allen et al., 1994, Adv. Drug Deliv. Rev, 13: 285-309. The invention also encompasses liposomes that are adapted for specific organ targeting, see, e.g., U.S. Pat. No. 4,544,545, or specific cell targeting, see, e.g., U.S. Patent Application Publication No. 2005/0074403. Particularly useful liposomes for use in the compositions and methods of the invention can be generated by reverse phase evaporation method with a lipid composition comprising phosphatidylcholine, cholesterol, and PEG derivatized phosphatidylethanolamine (PEG-PE). Liposomes are extruded through filters of defined pore size to yield liposomes with the desired diameter. In some embodiments, a fragment of an antibody of the invention, e.g., F(ab'), may be conjugated to the liposomes using previously described methods, see, e.g., Martin et al., 1982, *J. Biol. Chem.* 257: 286-288.

The humanized or chimeric antibodies of the invention may also be formulated as immunoliposomes. Immunoliposomes refer to a liposomal composition, wherein an antibody of the invention or a fragment thereof is linked, covalently or non-covalently to the liposomal surface. The chemistry of linking an antibody to the liposomal surface is known in the art and encompassed within the invention, see, e.g., U.S. Pat. No. 6,787,153; Allen et al., 1995, Stealth Liposomes, Boca Rotan: CRC Press, 233-44; Hansen et al., 1995, *Biochim. Biophys. Acta,* 1239: 133-144. In most preferred embodiments, immunoliposomes for use in the methods and compositions of the invention are further sterically stabilized. Preferably, the humanized antibodies of the invention are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art may be used, see, e.g., J. Thomas August, ed., 1997, Gene Therapy: Advances in Pharmacology, Volume 40, Academic Press, San Diego, Calif., p. 399-435. For example, a functional group on an antibody molecule may react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry,* 35: 1100-1105; Loughrey et al., 1987, *Biochim. Biophys. Acta,* 901: 157-160; Martin et al., 1982, *J. Biol. Chem.* 257: 286-288; Martin et al., 1981, *Biochemistry,* 20: 4429-38. Although not intending to be bound by a particular mechanism of action, immunoliposomal formulations comprising an antibody of the invention are particularly effective as therapeutic agents, since they deliver the antibody to the cytoplasm of the target cell, i.e., the cell comprising the receptor to which the antibody binds. The immunoliposomes preferably have an increased half-life in blood, specifically target cells, and can be internalized into the cytoplasm of the target cells thereby avoiding loss of the therapeutic agent or degradation by the endolysosomal pathway.

The immunoliposomal compositions of the invention comprise one or more vesicle forming lipids, an antibody of the invention or a fragment or derivative thereof, and, optionally, a hydrophilic polymer. A vesicle forming lipid is preferably a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations of the invention are known to one skilled in the art and encompassed within the invention. In some embodiments, the immunoliposomal compositions further comprise a hydrophilic polymer, e.g., polyethylene glycol, and ganglioside GM1, which increases the serum half-life of the liposome. Methods of conjugating hydrophilic polymers to liposomes are well known in the art and encompassed within the invention. For a review of immunoliposomes and methods of preparing them, see, e.g., U.S. Patent Application Publication No. 2003/0044407; PCT International Publication No. WO 97/38731, Vingerhoeads et al., 1994, *Immunomethods,* 4: 259-72; Maruyama, 2000, *Biol. Pharm. Bull.* 23(7): 791-799; Abra et al., 2002, *Journal of Liposome Research,* 12(1&2): 1-3; Park, 2002, *Bioscience Reports,* 22(2): 267-281; Bendas et al., 2001 *BioDrugs,* 14(4): 215-224, J. Thomas August, ed., 1997, Gene Therapy: Advances in Pharmacology, Volume 40, Academic Press, San Diego, Calif., p. 399-435.

The invention also provides that the humanized or chimeric antibodies of the invention are packaged in a hermetically sealed container, such as an ampoule or sachette, indicating the quantity of antibody. In one embodiment, the antibodies of the invention are supplied as a dry sterilized lyophilized powder or water free concentrate in a hermetically sealed container and can be reconstituted, e.g., with water or saline to the appropriate concentration for administration to a subject. Preferably, the antibodies of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies of the invention should be stored at between 2 and 8° C. in their original container and the antibodies should be administered within 12 hours, preferably within 6 hours, within 5 hours, within 3 hours, or within 1 hour after being reconstituted. In an alternative embodiment, antibodies of the invention are supplied in liquid form in a hermetically sealed container indicating the quantity and concentration of the antibody, fusion protein, or conjugated molecule. Preferably, the liquid form of the antibodies are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the antibodies.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations comprising one or more antibodies of the invention. See, e.g., U.S. Pat. No.

4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Intl. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760. In one embodiment, a pump may be used in a controlled release system (See Langer, supra; Sefton, 1987, *CRC Crit. Ref Biomed. Eng.* 14:20; Buchwald et al., 1980, Surgery 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, *Ann. Neurol.* 25:351; Howard et al., 1989, *J. Neurosurg.* 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533). Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Intl. Symp. Control Rel. Bioact. Mater.* 24:759-760.

In a specific embodiment wherein the therapeutic or prophylactic composition of the invention is a nucleic acid encoding an antibody of the invention or an antigen-binding fragment thereof, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

Treatment of a subject with a therapeutically or prophylactically effective amount of antibodies of the invention can include a single treatment or, preferably, can include a series of treatments.

D. Combination Therapies

The invention further encompasses administering the molecules of the invention in combination with other therapies known to those skilled in the art for the treatment or prevention of cancer, autoimmune disease, infectious disease or intoxication, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more agents, therapeutic antibodies or other agents known to those skilled in the art for the treatment and/or prevention of cancer, autoimmune disease, infectious disease or intoxication. Such agents include for example, any of the above-discussed biological response modifiers, cytotoxins, antimetabolites, alkylating agents, antibiotics, or anti-mitotic agents, as well as immunotherapeutics (such as ERBITUX™ (also known as IMC-C225) (ImClone Systems Inc.), a chimerized monoclonal antibody against EGFR; HERCEPTIN® (Trastuzumab) (Genentech, CA) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3™ is a humanized anti-ICAM3 antibody (ICOS Pharm); IDEC-114™ is a primatized anti-CD80 antibody (IDEC Pharm/Mitsubishi); ZEVALIN™ is a radiolabelled murine anti-CD20 antibody (IDEC/Schering AG); IDEC-131™ is a humanized anti-CD40L antibody (IDEC/Eisai); IDEC-151™ is a primatized anti-CD4 antibody (IDEC); IDEC-152™ is a primatized anti-CD23 antibody (IDEC/Seikagaku); SMART anti-CD3 is a humanized anti-CD3 IgG (Protein Design Lab); 5G1.1™ is a humanized anti-complement factor 5 (C5) antibody (Alexion Pharm); IDEC-151™ is a primatized anti-CD4 IgG1 antibody (IDEC Pharm/SmithKline Beecham); MDX-CD4™ is a human anti-CD4 IgG antibody (Medarex/Eisai/Genmab); CDP571™ is a humanized anti-TNF-α IgG4 antibody (Celltech); LDP-02™ is a humanized anti-α4β7 antibody (LeukoSite/Genentech); OrthoClone OKT4 A™ is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33™ is a human anti-CD64 (FcγR) antibody (Medarex/Centeon); rhuMab-E25™ is a humanized anti-IgE IgG1 antibody (Genentech/Norvartis/Tanox Biosystems); IDEC-152™ is a primatized anti-CD23 antibody (IDEC Pharm); ABX-CBL™ is a murine anti CD-147 IgM antibody (Abgenix); BTI-322™ is a rat anti-CD2 IgG antibody (Medimmune/Bio Transplant); Orthoclone/OKT3™ is a murine anti-CD3 IgG2a antibody (ortho Biotech); SIMULECT™ is a chimeric anti-CD25 IgG1 antibody (Novartis Pharm); LDP-01™ is a humanized anti-β$_2$-integrin IgG antibody (LeukoSite); Anti-LFA-1™ is a murine anti CD18 F(ab')$_2$ (Pasteur-Merieux/Immunotech); CAT-152™ is a human anti-TGF-β$_2$ antibody (Cambridge Ab Tech); and Corsevin M™ is a chimeric anti-Factor VII antibody (Centocor), etc.). In another embodiment the molecules of the invention are administered in combination with molecules that disrupt or enhance alternative immunomodulatory pathways (such as CTLA4, TIM3, TIM4, OX40, CD40, GITR, 4-1-BB, B7-H1, PD-1, LIGHT or LAG3) or modulate the activity of effecter molecules such as cytokines (e.g., IL-4, IL-7, IL-10, IL-12, IL-15, IL-17, GF-beta, IFNg, Flt3, BLys) and chemokines (e.g., CCL21) in order to enhance the immunomodulatory effects. In yet another embodiment, the molecules of the invention are administered in combination with molecules that activate different stages or aspects of the immune response in order to achieve a broader immune response. For example, blocking TAM-mediated immune suppression with an anti-B7-H4 molecule may be combined with a molecule that enhances T cell activation or priming in order to achieve a more robust immune response.

In certain embodiments, one or more molecules of the invention are administered to a mammal, preferably a human, concurrently with one or more other therapeutic agents useful for the treatment of cancer. The term "concurrently" is not limited to the administration of prophylactic or therapeutic agents at exactly the same time, but rather it is meant that a molecule of the invention and the other agent are administered to a mammal in a sequence and within a time interval such that the molecule of the invention can act together with the other agent to provide an increased benefit than if they were administered otherwise. For example, each prophylactic or therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect, or in a regimen that has been shown to provide therapeutic benefit. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active, or the pharmacodynamics effects are present. One skilled in the art would be able to determine such a time frame by determining the half-life of the administered agents.

In certain embodiments, the prophylactic or therapeutic agents of the invention are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled physician.

In other embodiments, courses of treatment are administered concurrently to a mammal, i.e., individual doses of the therapeutics are administered separately yet within a time interval such that molecules of the invention can work together with the other agent or agents. For example, one component may be administered one time per week in combination with the other components that may be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the molecules of the invention and the prophylactic and/or therapeutic agent can act additively or, more preferably, synergistically. In one embodiment, a molecule of the invention is administered concurrently with one or more therapeutic agents in the same pharmaceutical composition. In another embodiment, a molecule of the invention is administered concurrently with one or more other therapeutic agents in separate pharmaceutical compositions. In still another embodiment, a molecule of the invention is administered prior to or subsequent to administration of another prophylactic or therapeutic agent. The invention contemplates administration of a molecule of the invention in combination with other prophylactic or therapeutic agents by the same or different routes of administration, e.g., oral and parenteral. In certain embodiments, when a molecule of the invention is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the Physician's Desk Reference ($56^{th}$ ed., 2002).

E. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of humanized antibodies of the invention and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

F. Kits

The invention provides a pharmaceutical pack or kit comprising one or more containers filled with humanized antibodies of the invention. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more humanized antibodies of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

G. Diagnostic Methods

The antibodies of the invention and their antigen-binding fragments can be used for diagnostic purposes, such as to detect, diagnose, or monitor diseases, disorders or infections associated with B7-H4 expression, or to determine or assist in the determination or identification of suitable patient populations or profiles. The invention provides for the detection or diagnosis of a disease, disorder or infection, particularly an autoimmune disease comprising: (a) assaying the expression of B7-H4 in cells or in a tissue sample of a subject using one or more antibodies (or fragments thereof) that immunospecifically bind to such antigens; and (b) comparing the level of the antigen with a control level, e.g., levels in normal tissue samples, whereby an increase or decrease in the assayed level of antigen compared to the control level of the antigen is indicative of the disease, disorder or infection. Such antibodies and fragments are preferably employed in immunoassays, such as the enzyme linked immunosorbent assay (ELISA), the radioimmunoassay (RIA) and fluorescence-activated cell sorting (FACS).

One aspect of the invention relates to the use of such antibodies and fragments, and particularly such antibodies and fragments that bind to human B7-H4, as reagents for IHC analysis in cells of an in vitro or in situ tissue sample or in vivo. For example, since B7-H4 is particularly expressed by cancer cells but not by normal tissue (Sica, G. L. et al. (2003) "*B7-H4, A Molecule Of The B7 Family, Negatively Regulates T Cell Immunity,*" Immunity 18: 849-861; Choi, I. H. et al. (2003) "*Genomic Organization And Expression Analysis Of B7-H4, An Immune Inhibitory Molecule Of The B7 Family,*" J. Immunol. 171:4650-4654), detection of its presence on a cell by such cell's binding to such antibodies or fragments is indicative and diagnostic of a cancer cell. Thus, the present invention provides a cytologic assay for diagnosing the presence of cancer in a subject.

Since B7-H4 is over-expressed upon HIV infection (Carter, C. A. et al. (2008) "*Cell Biology Of HIV-1 Infection Of Macrophages,*" Ann. Rev. Microbiol. 62:425-443; Noursadeghi, M. et al. (2006) "*HIV-1 Infection Of Mononuclear Phagocytic Cells: The Case For Bacterial Innate Immune Deficiency In AIDS,*" Lancet Infect. Dis. 6:794-804), the expression of B7-H4 on such cells (as detected by the antibodies and antigen-binding fragments of the present invention) may be used to diagnose HIV in humans.

Thus, the antibodies and fragments of the present invention have utility in the detection and diagnosis of a disease, disorder, or infection in a human. In one embodiment, such diagnosis comprises: a) administering to a subject (for example, parenterally, subcutaneously, or intraperitoneally) an effective amount of a labeled antibody or antigen-binding fragment that immunospecifically binds to B7-H4; b) waiting for a time interval following the administration for permitting the labeled molecule to preferentially concentrate at sites in the subject where B7-H4 is expressed (and for unbound labeled molecule to be cleared to background level); c) determining background level; and d) detecting the labeled antibody in the subject, such that localized detection of labeled antibody above the background level indicates that the subject has the disease, disorder, or infection. In accordance with this embodiment, the antibody is labeled with an imaging moiety which is detectable in vivo using an imaging system known to one of skill in the art. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In vivo tumor imaging is described in S. W. Burchiel et al., "*Immunopharmacokinetics of Radiolabeled Antibodies and Their Fragments,*" (Chapter 13 in TUMOR IMAGING: THE RADIOCHEMICAL DETECTION OF CANCER, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Having now generally described the invention, the same will be more readily understood through reference to the following examples, which are provided by way of illustration and are not intended to be limiting of the present invention unless specified.

Example 1

Isolation and Characterization of Anti-Human B7-H4 Antibodies

In order to produce antibodies that immunospecifically bind to B7-H4 arrayed on the surface of a live cell, mice were immunized with a B7-H4 Ig fusion ("B7-H4Ig") comprising the extracellular domain (ECD) of murine B7-H4 linked to the hinge and Fc region of a mouse IgG2a.

In order to minimize the production of hybridomas producing Fc-reactive antibodies in favor of hybridomas that were ECD-reactive, immunizations and boosts were conducted using a B7-H4Ig construct having a murine Fc region ("B7-H4mIg"). A murine Fc region was employed as being potentially less immunogenic (than a human Fc region) in a murine host and to therefore favor the production of hybridomas producing ECD-reactive antibodies. KLH was conjugated to the B7-H4mIg construct in order to increase its immunogenicity.

Serum from three mice was screened for its ability to bind human B7-H4Ig ("B7-H4hIg") following immunization and boosting (FIG. 1). Mouse 2 was found to have the highest titer of anti-human B7-H4hIg antibodies and was selected for use in hybridoma production. Hybridomas were produced by isolating splenocytes from Mouse 2 and fusing them to immortalized myeloma cells.

A plate-based binding assay using the B7-H4hIg construct was employed to capture the elicited antibody; antibodies were then characterized as being either IgG or IgM. As a specificity control, antibodies were also subjected to capture with a B7-DChIg construct (comprising the extracellular domain (ECD) of human DC linked to the hinge and Fc region of a human IgG1) ("B7-DChIg") and the extent of IgG capable of binding was measured.

Figure 2:
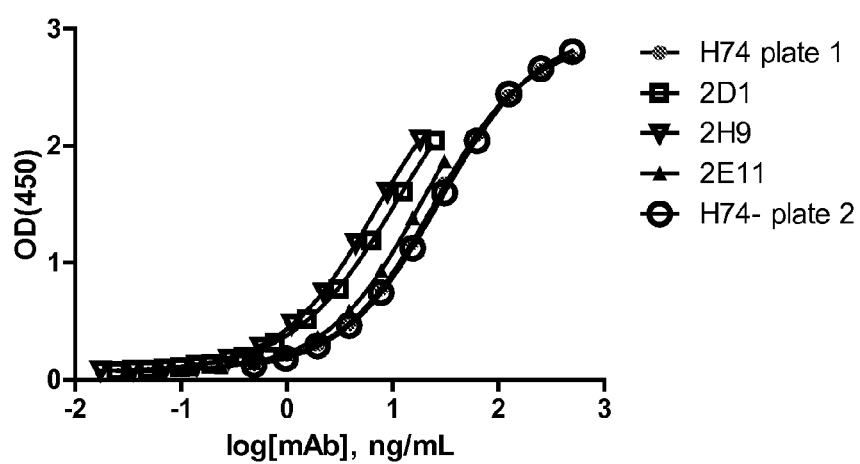
FIG. 2 shows binding of anti-B7-H4 antibodies to plate bound B7-H4hIg. Serial dilutions were made from H74 (a commercially available anti-B7-H4 antibody), 2D1, 2E11 and 2H9 stock solutions and added to 96-well ELISA plates coated with B7-H4hIg or B7-DChIg. After incubation and wash, horseradish peroxidase (HRP) conjugated anti-mouse IgG antibody was added to the plates. After incubation and wash, 3,3',5,5'-Tetramethylbenzidine (TMB) substrate was added. The colorimetric development was stopped by $H_2SO_4$ stop solution and read with a plate reader measuring absorbance at a 450 nm wavelength.

Seven hybridomas producing IgG and three hybridomas producing IgM whose antibodies were specific for the B7-H4 ECD were produced. Of these, five IgG1-producing clones (2E11, 2H7, 2H8, 2H9, 2H10), one IgG2-producing clone (2D1) and two IgM-producing clones (1H11, 2F2) were further analyzed. Their binding capacity was compared to that of a commercially available anti-human B7-H4 antibody, Clone H74 from eBioScience (FIG. 2). Antibody concentration and binding titer were determined for hybridoma supernatants. The following hybridomas: 2D1, 2H9, and 2E11, showed compatible or better specific binding activity to the B7-H4Ig construct but not to the B7-DChIg construct when compared to the H74; therefore, they were chosen as preferred clones for further analysis.

Example 2

Isolation of Anti-B7-H4 Antibodies

Figure 3:
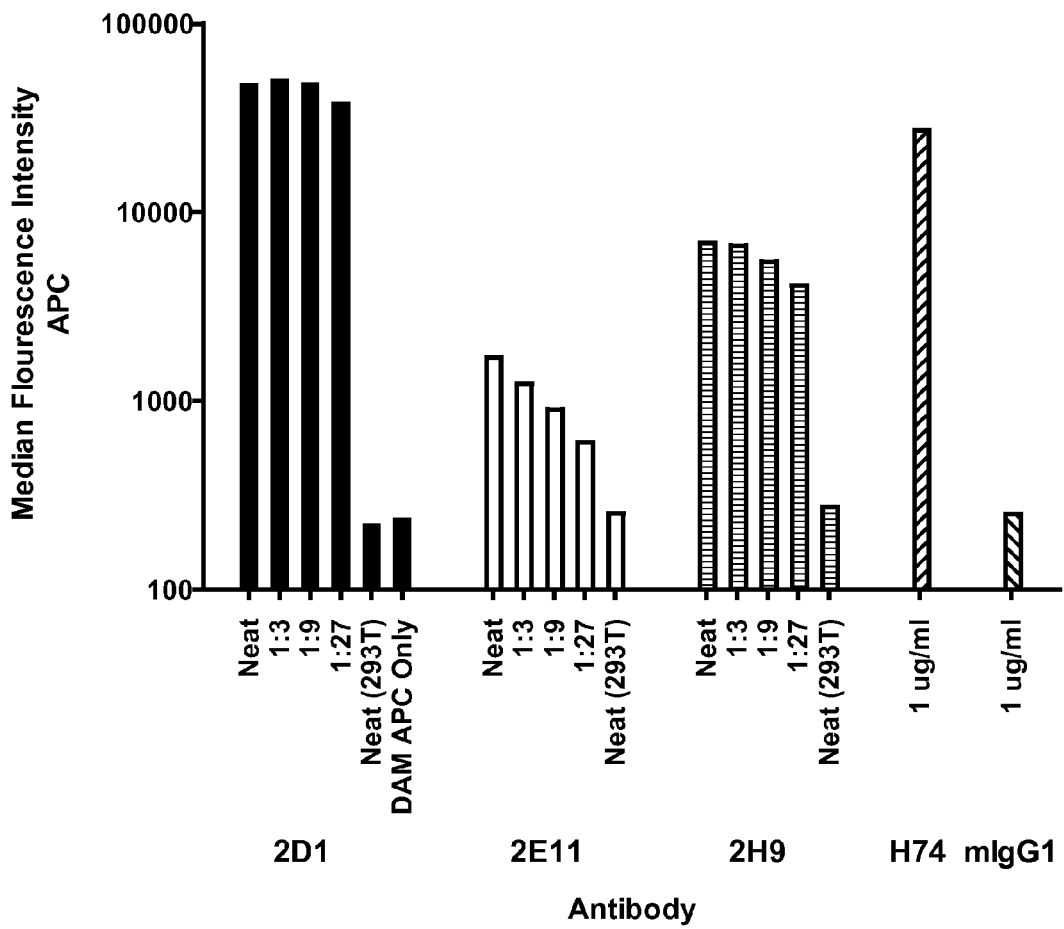
FIG. 3 shows anti-B7-H4 antibodies binding to 293T.B7-H4 cells. Antibodies 2D1, 2E11 and 2H9 were used either un-diluted (Neat), or diluted at 1:3, 1:9 and 1:27, to stain 293T.B7-H4 cells. For binding detection, APC labeled anti-mouse IgG antibody was utilized followed by FACS analysis of APC positive cells. H74 (a commercially available anti-B7-H4 antibody) at 1 μg/mL was used as positive control. Negative control was 1 μg/mL of mIgG1. 293T.B7-H4 cells incubated with APC labeled anti-mouse IgG antibody (DAM APC only), and parent 293 T cells stained with un-diluted 2D1 (Neat [293T]) further served as negative binding controls.
Figure 4A:
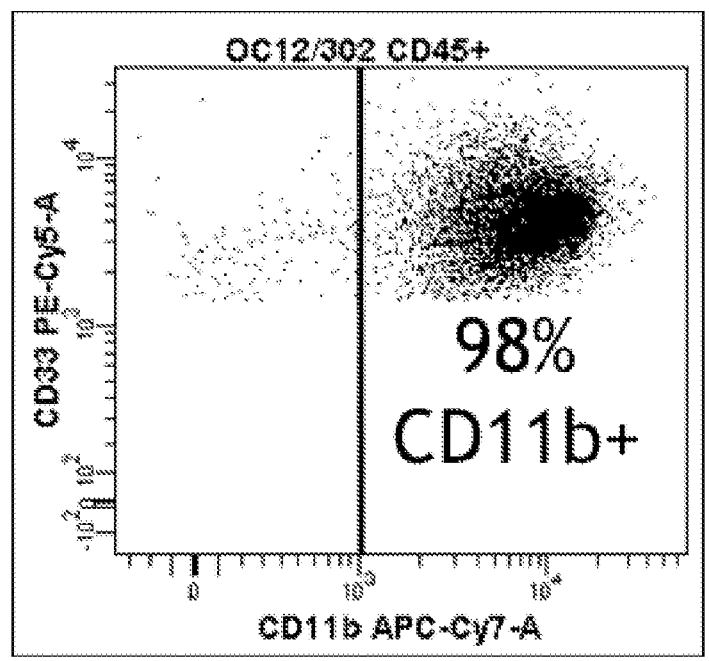
FIGS. 4A-4I, respectively, show the use of fluorescence-activated cell sorting (FACS) to determine the proportion of CD11b$^+$, CD19$^+$, CD14$^+$, CD123$^+$, CD86$^+$, CD80$^+$, HLA-DC$^+$, B7-H1$^+$, B7-H4$^+$, and B7-DC$^+$, TAMs isolated from ascites from ovarian cancer patients.
Figure 4B:
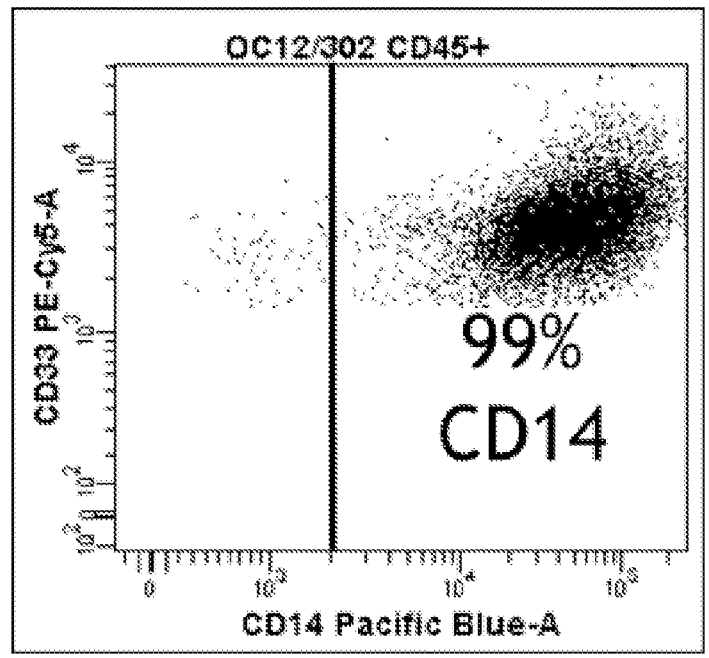
Figure 4C:
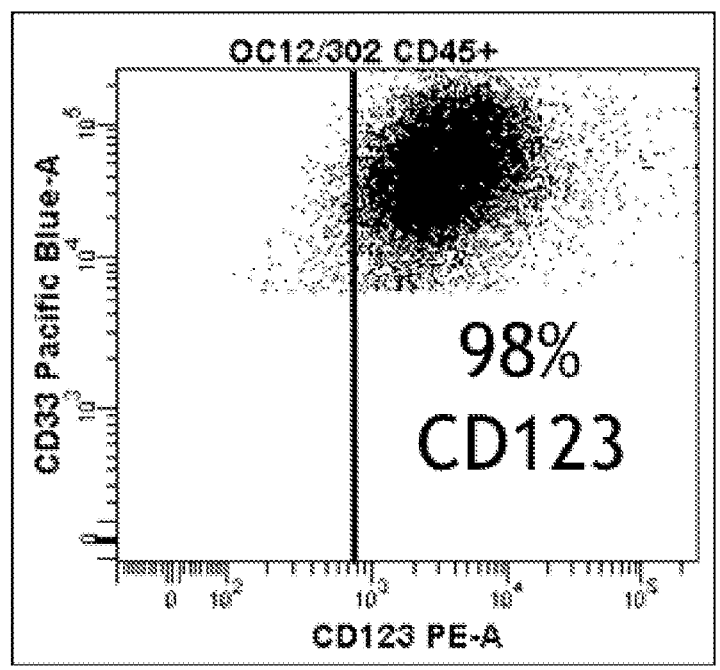
Figure 4D:
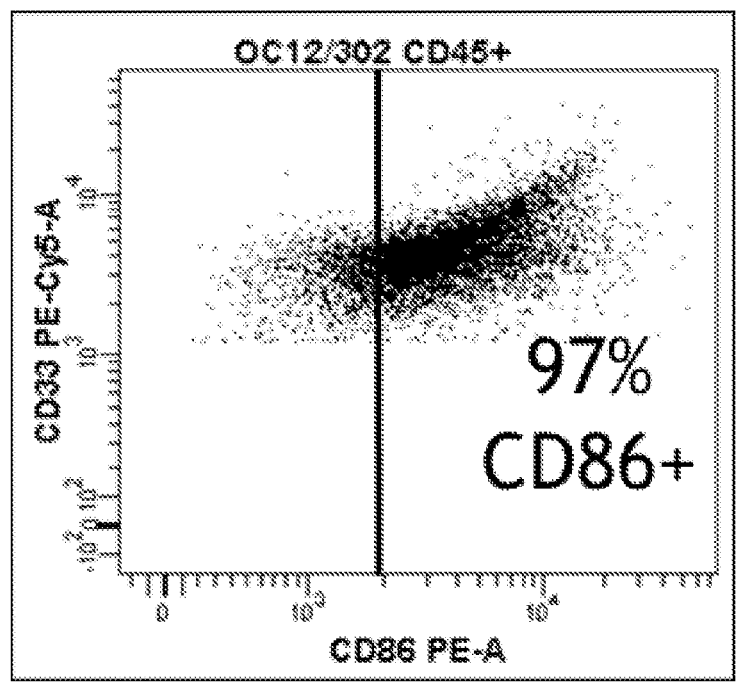
Figure 4E:
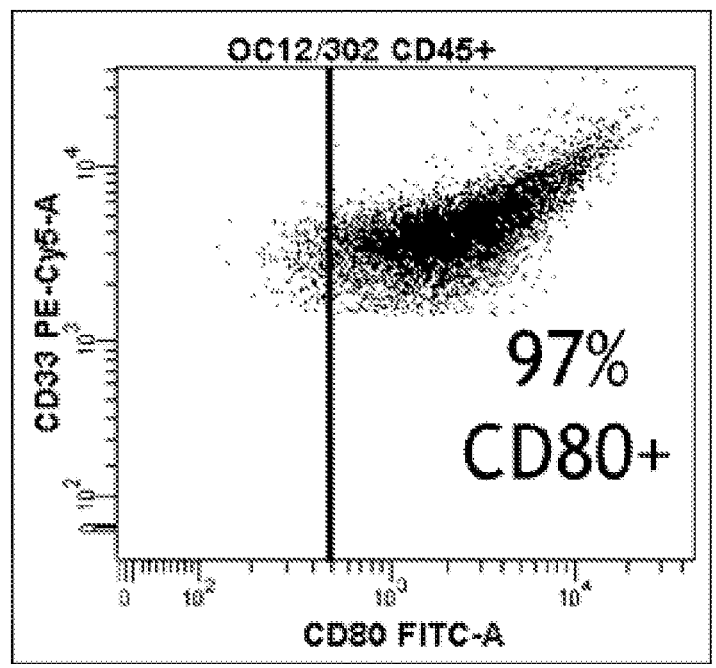
Figure 4F:
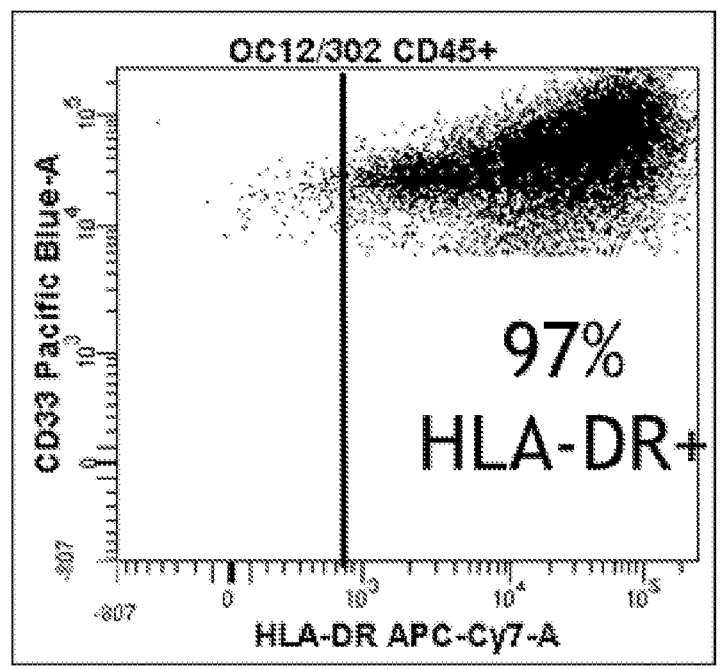
Figure 4G:
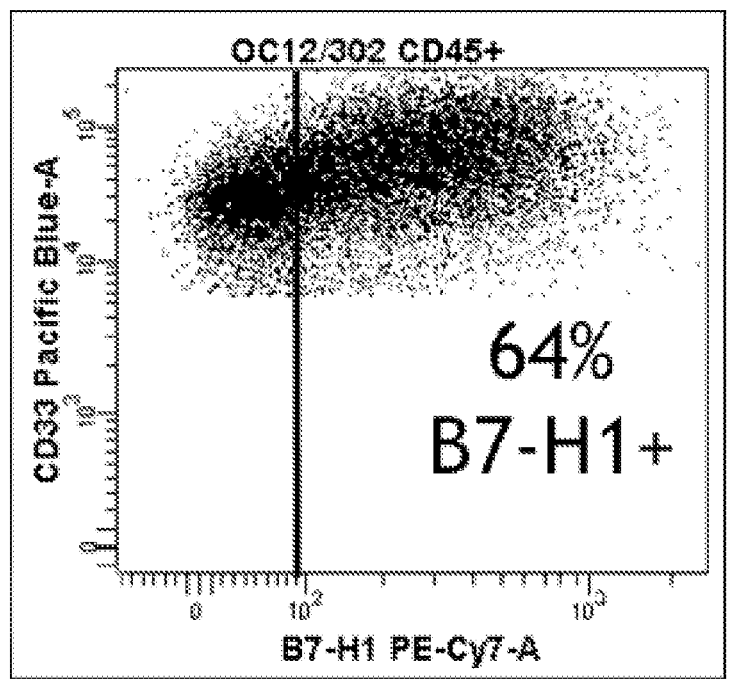
Figure 4H:
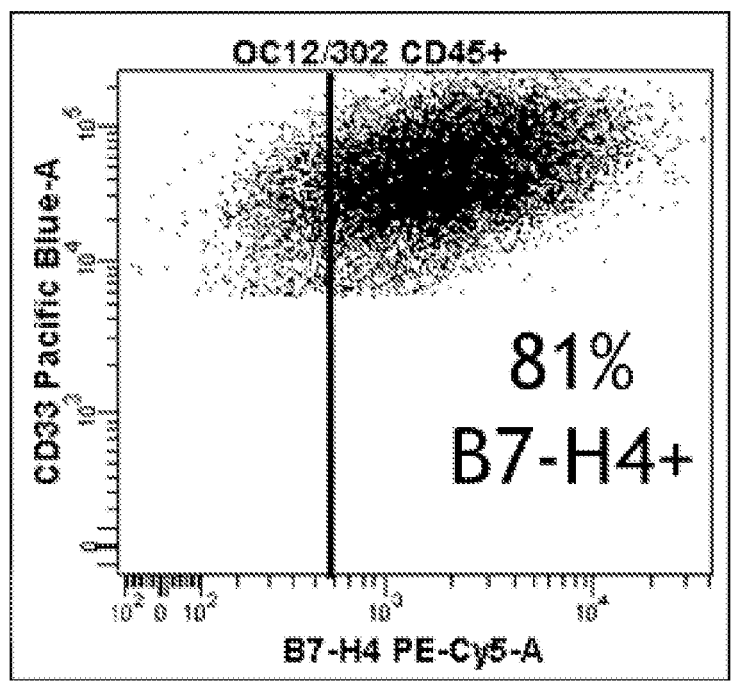
Figure 4I:
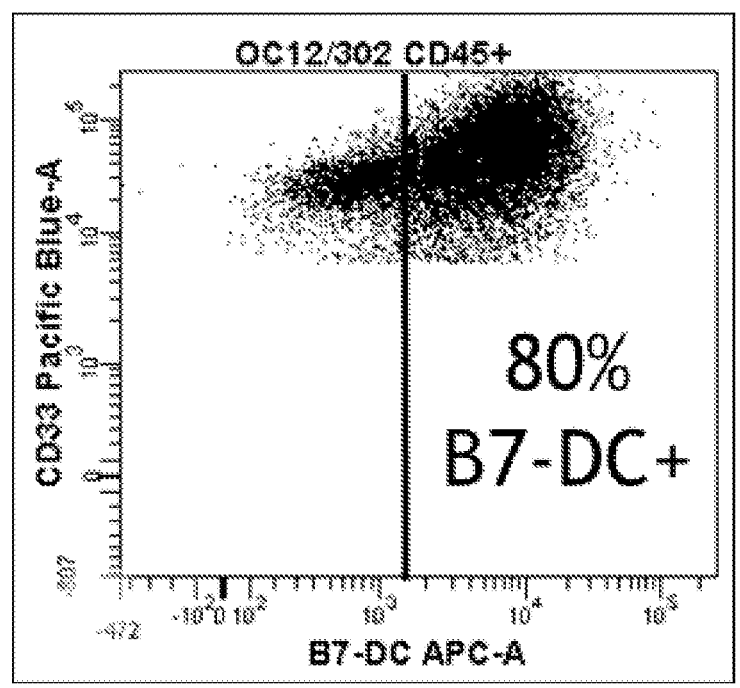
Figure 5A:
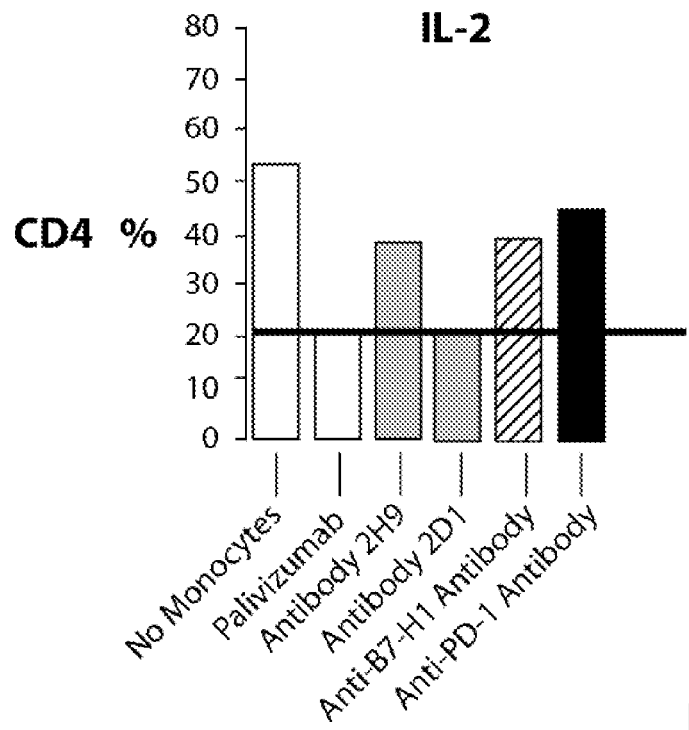
FIGS. 5A-5E show the ability of the molecules of the present invention to reverse IFNγ primed monocyte-mediated suppression. T cells were stained for IL-2 (CD4$^+$, T cells, FIG. 5A; CD8$^+$, T cells, FIG. 5B), TNFα (CD4$^+$, T cells, FIG. 5C; CD8$^+$, T cells, FIG. 5D) or IL-8 (CD4$^+$, T cells, FIG. 5E; CD8$^+$,T cells, FIG. 5F).
Figure 5B:
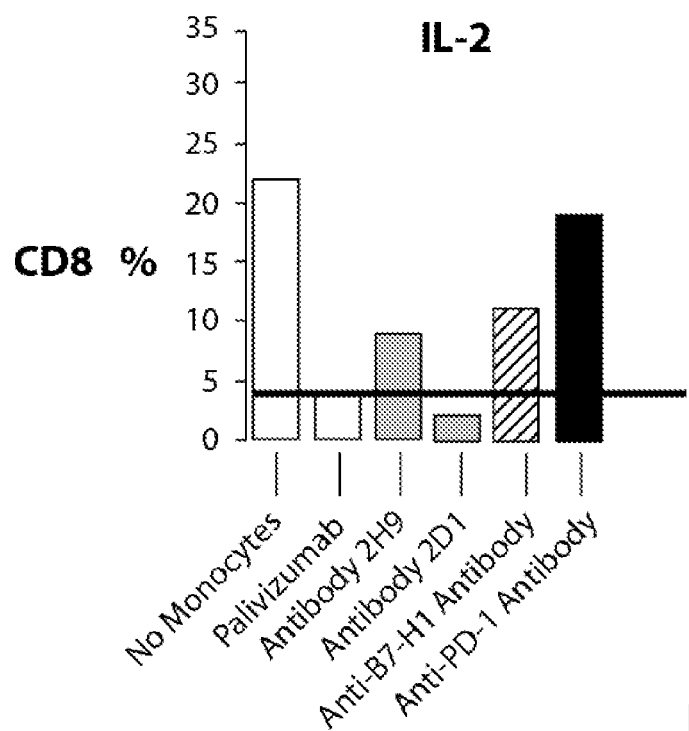
Figure 5C:
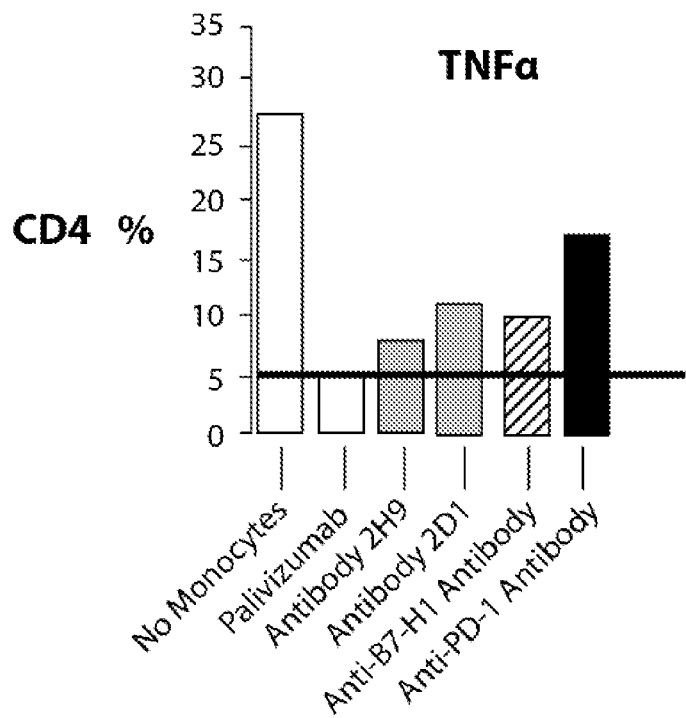
Figure 5D:
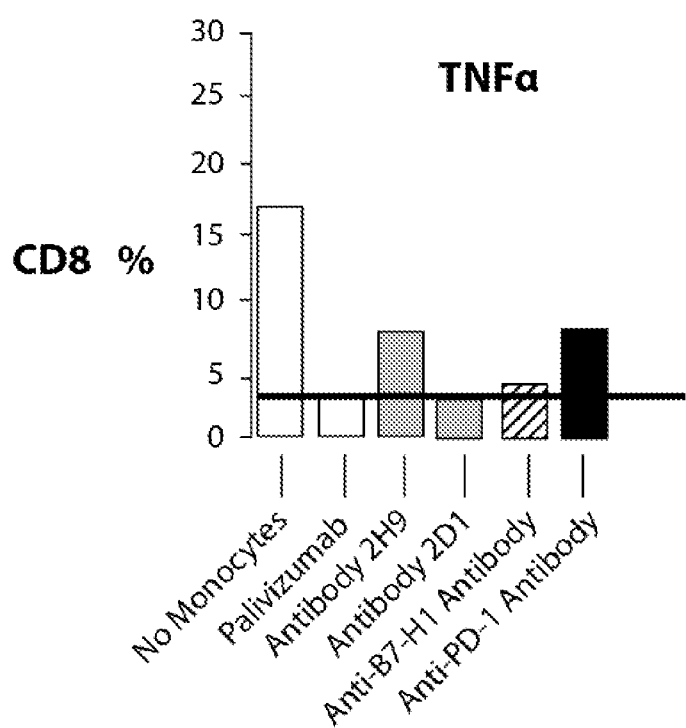
Figure 5E:
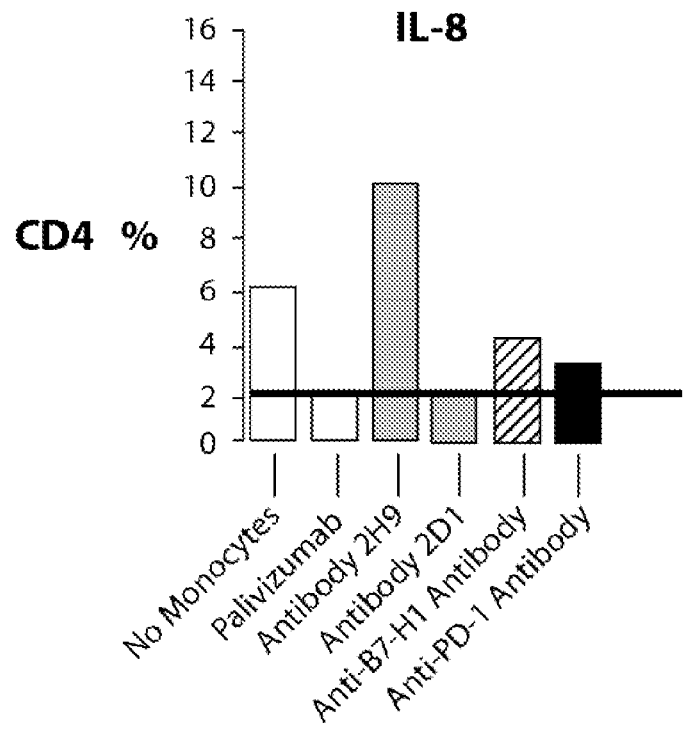
Figure 5F:
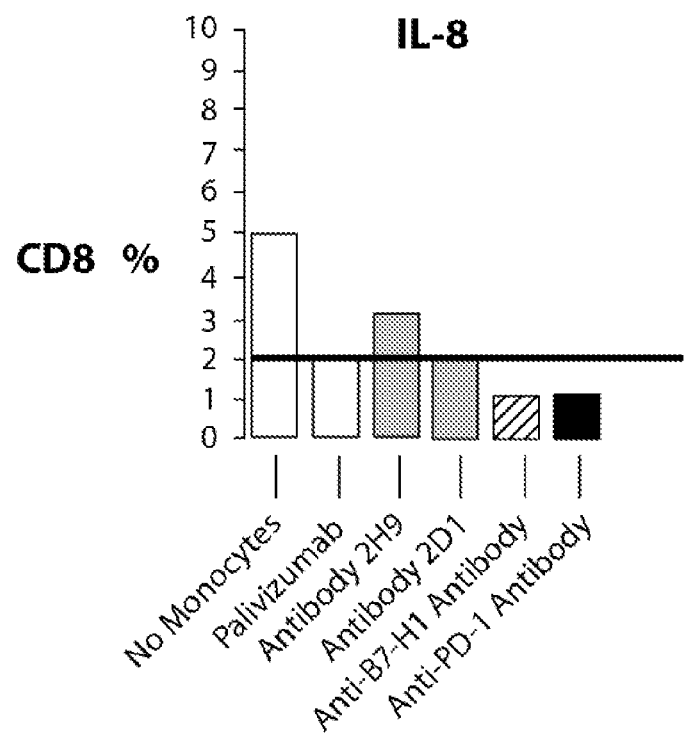

In order to demonstrate the ability of the anti-human B7-H4 antibodies to bind to B7-H4 expressed on the surface of a cell, human embryonic kidney 293 cells ("HEK293 cells") were stably transfected to express human B7-H4 on their surfaces. Neat and diluted hybridoma supernatants were then tested for the ability of their antibodies to bind to such cells or to control B7-H4$^+$ HEK293 cells. After washing, bound antibody was detected with allophycocyanin (APC)-conjugated, anti-mouse antibodies and the mean fluorescent intensity of the cells was determined (FIG. 3).

The results show that anti-human B7-H4 antibodies 2D1, 2E11 and 2H9 were all capable of immunospecifically binding to human B7-H4 arrayed on the surface of a live cell.

Example 3

Anti-B7-H4 Antibodies Reverse Immune Suppression of Tumor-Associated Macrophages (TAMs) of Ovarian Cancer Patients As discussed above, tumor environmental macrophages that are B7-H4$^+$ significantly suppress T cell activation. B7-H4$^-$ macrophages can be converted into B7-H4$^+$ macrophages by IL-10 and IL-6 in vitro (Kryczek, I. et al. (2006) "*Cutting Edge: Induction Of B7-H4 On APCs Through IL-10: Novel Suppressive Mode For Regulatory T Cells,*" J. Immunol. 177(1):40-44). Thus, the proportion of B7-H4$^+$ to B7-H4$^-$ macrophages and of B7-H4$^+$ to total tumor-associated macrophages correlates with tumor aggressiveness and the severity of cancer. Experiments are conducted to demonstrate the ability of the molecules of the present invention to elucidate such proportions so as to permit the correlation of B7-H4 expression on tumor-associated macrophages with tumor aggressiveness and the severity of cancer.

For such experiments, TAMs were isolated from the ovarian cancer patients' ascites and subjected to fluorescence-activated cell sorting (FACS) to determine the proportion of such macrophages that expressed T cell activation, suppression and cell cycling markers. T cell proliferation is preferably determined by thymidine incorporation. Preferably, an analysis of cell cycling in different phases is also conducted. FIGS. 4A-4I, respectively, show the expression of CD11b$^+$, CD19$^+$, CD14$^+$, CD123$^+$, CD86$^+$, CD80$^+$, HLA-DC$^+$, B7-H1$^+$, B7-H4$^+$ and B7-DC$^+$ on TAMs isolated from such ovarian ascites. The results indicate that 81% of the TAMs of the tumors tested were B7-H4$^+$.

Example 4

B7-H4/B7-H1/PD-1 Blocking Antibodies Reverse Immune Suppression of Ovarian Cancer Patients' TAMs As discussed above, tumor environmental B7-H4$^+$ macrophages have been found to significantly suppress T cell activation and such suppression can be reduced by blocking B7-H4. Additionally, B7-H4$^-$ macrophages can be converted in vitro into B7-H4$^+$ macrophages by cytokines (IL-10 and IL-6) that are found in the tumor environment. Experiments are conducted to demonstrate the ability of the molecules of the present invention to neutralize B7-H4-mediated immune suppression. The results of this investigation show that cells receiving anti-B7-H4, anti-B7-H1 or anti-PD-1 antibodies exhibit increased $^3$H-thymidine incorporation relative to human T cells upon anti-CD3 activation in the absence of TAMs (Control) or presence of TAMs treated with an isotype control mAb. Such increased incorporation indicates that anti-B7-H4 antibody is capable of blocking the suppression of TAMs mediated by B7-H4. Furthermore, anti-B7-H1 and anti-PD-1 antibodies are each capable of blocking the suppression of TAMs mediated by B7-H.

Example 5

B7-H4/B7-H1/PD-1 Blockade Antibodies Significantly Enhance CTL Response Post-OV TAM Coincubation in an Allo T Cell Assay In order to demonstrate the ability of the molecules of the present invention to enhance a cytotoxic lymphocyte (CTL) response, CD4+ and CD8+ T cells are incubated in the presence of ovarian tumor-derived TAMs and either control isotype antibody, anti-B7-H4 antibody, anti-B7-H1 antibody or anti-PD-1 antibody. The capacity of the T cells to express IL-17 and IFN-γ as a consequence of such coincubation is measured using FACS.

The results of this experiment show that after incubation with an isotype monoclonal antibody control, the CD4$^+$ T cells comprise a minor component of Th17 (IL-17-producing) T cells, and a minor component expressing IFN-γ. A similar result is obtained for CD8$^+$ T cells. In contrast, CD4$^+$ T cells incubated in the presence of anti-B7-H4 antibody, anti-B7-H1 antibody or anti-PD-1 antibody exhibit significant enhancement of IL-17 and IFN-γ, and CD8$^+$ T cells incubated in the presence of anti-B7-H4 antibody exhibit significant enhancement of IFN-γ expression.

Example 6

B7-H4 Blocking Antibodies can Reverse Monocyte Mediated Suppression

In order to demonstrate the ability of the molecules of the present invention to block immune suppression, IFN-γ primed monocytes from healthy donors were incubated with anti-B7-H4 antibody, anti-B7-H1 antibody, anti-PD-1 antibody, or a negative control antibody (SYNAGIS® palivizumab (Medimmune, Inc.), directed to an epitope in the A antigenic site of the F protein of respiratory syncytial virus (RSV)). Autologous T cells were activated with anti-CD3 antibody and co-incubated with the pre-treated monocytes at a ratio of 10 T cells per 1 macrophage, in the presence of antibody. The T cells were harvested and stained for CD4 and CD8, and were intracellularly stained for IL-2, TNF-α and IL-8.

The results of this investigation are shown in FIGS. 5A-5E. Incubation of the primed monocytes in the presence of the negative control antibody resulted in significant monocyte suppression. In the absence of monocytes there is no suppression of T cell activity.

Example 7

Molecular Construction and Production of Recombinant Anti-B7-H4 Antibodies

DNA amplification products obtained from hybridomas that express anti-B7-H4 antibodies 2H9, 2D1 and 2E11 were used as templates for full length IgG construction. Chimeric antibodies were produced having a human IgG4 backbone modified at position 228 (S228P). The S228P modification yields an IgG4 molecule with a hinge region having greater similarity to the hinge region of an IgG1 (Aalberse, R. C. et al. (2002) "*IgG4 Breaking The Rules*," Immunology 105:9-19; Angal, S. et al. (1993) "*A Single Amino Acid Substitution Abolishes The Heterogeneity Of Chimeric Mouse/Human (IgG4) Antibody*," Molec. Immunol 30:105-108; Bloom, J. W. et al. (1997) "*Intrachain Disulfide Bond In The Core Hinge Region Of Human IgG4*," Protein Sci 6:407-415; Schuurman, J. et al. (2001) "*The Interheavy Chain Disulfide Bonds Of IgG4 Are In Equilibrium With Intra-Chain Disulfide Bonds*," Molec. Immunol 38:1-8). The nucleotide and amino acid sequences corresponding to the mature full length IgG are as follows:

Nucleotide Sequence Encoding the Light Chain of Anti-B7-H4 Antibody 2D1 (SEQ ID NO:33):

```
gatgttgtga tgacccaaac tccactctcc ctgcctgtca
gtcttggaga tcaagcctcc atctcttgca gatctagtca
cagccttgta cacagtaatg gaaacaccta tttacattgg
tacctgcaga agccaggcca gtctccaaac ctcctgatct
acatagtttc caaccgattt tctggggtcc cagacaggtt
cagtggcagt ggatcaggga cagatttcac actcaagatc
agcagagtgg aggctgagga tctgggagtt tatttctgct
ctcaaagtac acatgttcct cccacgttcg gtgctgggac
```
caagctggag ctgaagcgga ccgtggccgc ccccagcgtg ttcatcttcc ctcccagcga cgagcagctg aagtctggca ccgccagcgt ggtgtgcctg ctgaacaact tctaccccg cgaggccaag gtgcagtgga aggtggacaa cgccctgcag agcggcaaca gccaggagag cgtgaccgag caggactcca aggacagcac ctacagcctg agcagcaccc tgaccctgag caaggccgac tacgagaagc acaaggtgta cgcctgcgag gtgacccacc agggactgtc tagccccgtg accaagagct tcaaccgggg cgagtgc Amino Acid Sequence of the Light Chain of Anti-B7-H4 Antibody 2D1 (SEQ ID NO:34) [the sequence of the variable domain (SEQ ID NO:3) is shown underlined]:

<u>DVVMTQTPLS LPVSLGDQAS ISCRSSHSLV HSNGNTYLHW</u>

<u>YLQKPGQSPN LLIYIVSNRF SGVPDRFSGS GSGTDFTLKI</u>

<u>SRVEAEDLGV YFCSQSTHVP PTFGAGTKLE</u> LKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC

Nucleotide Sequence Encoding the Heavy Chain of Anti-B7-H4 Antibody 2D1 (SEQ ID NO:35):

```
gaagtgcagc tggtggagtc tgggggaggc ttagtgaagc
ctggagggtc cctgaaactc tcctgtgcag cctctggatt
cactttcaat agccatggca tgtcttgggt tcgccagact
ccggaaaaga ggctggactg ggtcgcaacc attagtgatg
gtggtactta cacctactat ccagtcaatg taaagggccg
attcaccatc tccagagaca tgccaagaa caacctgtac
ctgcaaatga gccatctgaa gtccgaggac acagccatgt
attactgtgc aagagatggg gggggagggg cttactgggg
ccaagggact ctggtcactg tctctgcagc tagcaccaag
ggtccatcgg tcttcccact ggcgccttgc tccaggagca
cctccgagag cacagccgct ctgggttgcc tggtcaagga
ctacttcccc gaaccggtga cggtgtcgtg gaactcaggt
gccctgacca gcggcgtgca caccttcccg gctgtcctac
agtcctcagg actctactcc ctcagcagcg tggtgaccgt
gccctccagc agcttgggta cgaagaccta cacctgcaac
gtagatcaca agcccagcaa caccaaggtg gacaagagag
ttgagtccaa atatggtcct ccatgccac catgcccagc
acctgagttc ctgggtggac catcagtctt cctgttccca
ccaaaaccca aggacactct catgatctcc cggacccctg
aggtcacgtg cgtcgtagtt gacgtgagcc aggaagaccc
```

-continued

```
cgaggtccag ttcaactggt acgtggatgg cgtggaggtg
cataatgcca agacaaagcc gcgggaggag cagttcaaca
gcacgtaccg tgtggtcagc gtcctcaccg tcctgcacca
ggactggctg aacggcaagg agtacaagtg caaggtctcc
aacaaaggcc tcccgtcctc catcgagaaa accatctcca
aagccaaagg gcagccacga gagccacagg tgtacaccct
gcctccatcc caggaagaga tgaccaagaa ccaggtcagc
ctgacctgcc tggtcaaagg cttctaccct agcgacatcg
ccgtggagtg ggagagcaat gggcagccgg agaacaacta
caagaccacg cctccagtgc tggactccga cggctccttc
ttcctctaca gcaggctcac cgtggacaag agcaggtggc
aggagggtaa tgtcttctca tgctccgtga tgcatgaggc
tctgcacaac cactacacac agaagagcct gagcctgagc
cccggaaag
```

Amino Acid Sequence of the Heavy Chain of Anti-B7-H4 Antibody 2D1 (SEQ ID NO:36) [the sequence of the variable domain (SEQ ID NO:4) is shown underlined]:

```
EVQLVESGGG LVKPGGSLKL SCAASGFTFN SHGMSWVRQT
PEKRLDWVAT ISDGGTYTYY PVNVKGRFTI SRDNAKNNLY
LQMSHLKSED TAMYYCARDG GGGAYWGQGT LVTVSAASTK
GPSVFPLAPC SRSTSESTAA LGCLVKDYFP EPVTVSWNSG
ALTSGVHTFP AVLQSSGLYS LSSVVTVPSS SLGTKTYTCN
VDHKPSNTKV DKRVESKYGP PCPPCPAPEF LGGPSVFLFP
PKPKDTLMIS RTPEVTCVVV DVSQEDPEVQ FNWYVDGVEV
HNAKTKPREE QFNSTYRVVS VLTVLHQDWL NGKEYKCKVS
NKGLPSSIEK TISKAKGQPR EPQVYTLPPS QEEMTKNQVS
LTCLVKGFYP SDIAVEWESN GQPENNYKTT PPVLDSDGSF
FLYSRLTVDK SRWQEGNVFS CSVMHEALHN HYTQKSLSLS
PGK
```

Nucleotide Sequence Encoding the Light Chain of Anti-B7-H4 Antibody 2H9 (SEQ ID NO:37):

```
gacattgtgc tgacccaatc tccagcttct ttggctgtgt
ctctagggca gagggccacc atctcctgca gagccagcga
aagtattgat aattatggca ttagttttat gcactggtac
cagcagaaac caggacagcc acccaaactc ctcatctatc
gtgcatccaa cctagaatct gggatccctg ccaggttcag
tggcagtggg tctaggacag acttcaccct caccattaat
cctgtggaga ctgatgatgt tgcaacctat ttctgtcagc
aaagtgatga gggtcggacg ttcggtggag gcaccaagct
ggaaatcaag cggaccgtgg ccgcccccag cgtgttcatc
ttccctccca gcgacgagca gctgaagtct ggcaccgcca
gcgtggtgtg cctgctgaac aacttctacc cccgcgaggc
caaggtgcag tggaaggtgg acaacgccct gcagagcggc
aacagccagg agagcgtgac cgagcaggac tccaaggaca
gcacctacag cctgagcagc accctgaccc tgagcaaggc
cgactacgag aagcacaagg tgtacgcctg cgaggtgacc
caccagggac tgtctagccc cgtgaccaag agcttcaacc
ggggcgagtg c
```

Amino Acid Sequence of the Light Chain of Anti-B7-H4 Antibody 2H9 (SEQ ID NO:38) [the sequence of the variable domain (SEQ ID NO:7) is shown underlined]:

```
DIVLTQSPAS LAVSLGQRAT ISCRASESID NYGISFMHWY
QQKPGQPPKL LIYRASNLES GIPARFSGSG SRTDFTLTIN
PVETDDVATY FCQQSDEGRT FGGGTKLEIK RTVAAPSVFI
FPPSDEQLKS GTASVVCLLN NFYPREAKVQ WKVDNALQSG
NSQESVTEQD SKDSTYSLSS TLTLSKADYE KHKVYACEVT
HQGLSSPVTK SFNRGEC
```

Nucleotide Sequence Encoding the Heavy Chain of Anti-B7-H4 Antibody 2H9 (SEQ ID NO:39):

```
gaagtgcagc tggtggagtc tgggggaaac ttagtgaagc
ctggagggtc cctgaaactc tcctgtgcag cctctggatt
cactttcagt aactctgcca tgtcttgggt tcgccagact
ccggaaaaga ggctggagtg ggtcgcaacc attagtgatg
gtggtcgtta cacctactat ccagacaatg taagggccg
attcaccatc tccagagaca atgccaagaa caacctgtac
ctgcaaatga gccatctgaa gtctgaggac acagcccttt
attactgtgc aagagatcga ccccactggt acttcgatgt
ctgggcaca ggggccacgg tcaccgtctc ctcagctagc
accaagggtc catcggtctt cccactggcg ccttgctcca
ggagcacctc cgagagcaca gccgctctgg gttgcctggt
caaggactac ttccccgaac cggtgacggt gtcgtggaac
tcaggtgccc tgaccagcgg cgtgcacacc ttcccggctg
tcctacagtc ctcaggactc tactccctca gcagcgtggt
gaccgtgccc tccagcagct gggtacgaa gacctacacc
tgcaacgtag atcacaagcc cagcaacacc aaggtggaca
agagagttga gtccaaatat ggtcctccat gcccaccatg
cccagcacct gagttcctgg tgaccatc agtcttcctg
ttcccaccaa aacccaagga cactctcatg atctcccgga
cccctgaggt cacgtgcgtc gtagttgacg tgagccagga
agacccgag gtccagttca actggtacgt ggatggcgtg
```

```
gaggtgcata atgccaagac aaagccgcgg gaggagcagt
tcaacagcac gtaccgtgtg gtcagcgtcc tcaccgtcct
gcaccaggac tggctgaacg gcaaggagta caagtgcaag
gtctccaaca aaggcctccc gtcctccatc gagaaaacca
tctccaaagc caagggcag ccacgagagc cacaggtgta
caccctgcct ccatcccagg aagagatgac caagaaccag
gtcagcctga cctgcctggt caaaggcttc taccctagcg
acatcgccgt ggagtgggag agcaatgggc agccggagaa
caactacaag accacgcctc cagtgctgga ctccgacggc
tccttcttcc tctacagcag gctcaccgtg gacaagagca
ggtggcagga gggtaatgtc ttctcatgct ccgtgatgca
tgaggctctg cacaaccact acacacagaa gagcctgagc
ctgagccccg gaaag
```

Amino Acid Sequence of the Heavy Chain of Anti-B7-H4 Antibody 2H9 (SEQ ID NO:40) [the sequence of the variable domain (SEQ ID NO:8) is shown underlined]:

```
EVQLVESGGN LVKPGGSLKL SCAASGFTFS NSAMSWVRQT
PEKRLEWVAT ISDGGRYTYY PDNVKGRFTI SRDNAKNNLY
LQMSHLKSED TALYYCARDR PHWYFDVWGT GATVTVSSAS
TKGPSVFPLA PCSRSTSEST AALGCLVKDY FPEPVTVSWN
SGALTSGVHT FPAVLQSSGL YSLSSVVTVP SSSLGTKTYT
CNVDHKPSNT KVDKRVESKY GPPCPPCPAP EFLGGPSVFL
FPPKPKDTLM ISRTPEVTCV VVDVSQEDPE VQFNWYVDGV
EVHNAKTKPR EEQFNSTYRV VSVLTVLHQD WLNGKEYKCK
VSNKGLPSSI EKTISKAKGQ PREPQVYTLP PSQEEMTKNQ
VSLTCLVKGF YPSDIAVEWE SNGQPENNYK TTPPVLDSDG
SFFLYSRLTV DKSRWQEGNV FSCSVMHEAL HNHYTQKSLS
LSPGK
```

Nucleotide Sequence Encoding the Light Chain of Anti-B7-H4 Antibody 2E11 (SEQ ID NO:41):

```
gacatcgtga tgagccagag ccctagcagc ctggccgtgt
ccgtgggaga gaaagtgacc gtgtcctgca agagcagcca
gtccctgctg tactccacca accagagaac ctacctggcc
tggttccagc agaagcccgg ccagtctccc aagctgctga
tctactgggc cagcaccaga gaaagcggcg tgcccgacag
attcacaggc agcggctctg gcaccgactt cacccctgaca
atcagcagcg tgaaggccga ggacctggct gtgtactact
gccagcagta ctacaactac cccctgacct tcggcaccgg
caccaagctg gaactgaaga gaaccgtggc cgctcccagc
gtgttcatct tcccacctag cgacgagcag ctgaagtccg
```

```
gcacagcctc tgtcgtgtgc ctgctgaaca acttctaccc
ccgcgaggcc aaggtgcagt ggaaggtgga caacgccctg
cagagcggca acagccagga aagcgtgacc gagcaggaca
gcaaggactc cacctacagc ctgagcagca ccctgaccct
gagcaaggcc gactacgaga agcacaaggt gtacgcctgc
gaagtgaccc accagggcct gtctagcccc gtgaccaaga
gcttcaacag aggcgagtgc
```

Amino Acid Sequence of the Light Chain of Anti-B7-H4 Antibody 2E11 (SEQ ID NO:42) [the sequence of the variable domain (SEQ ID NO:5) is shown underlined]:

```
DIVMSQSPSS LAVSVGEKVT VSCKSSQSLL YSTNQRTYLA
WFQQKPGQSP KLLIYWASTR ESGVPDRFTG SGSGTDFTLT
ISSVKAEDLA VYYCQQYYNY PLTFGTGTKL ELKRTVAAPS
VFIFPPSDEQ LKSGTASVVC LLNNFYPREA KVQWKVDNAL
QSGNSQESVT EQDSKDSTYS LSSTLTLSKA DYEKHKVYAC
EVTHQGLSSP VTKSFNRGEC
```

Nucleotide Sequence Encoding the Heavy Chain of Anti-B7-H4 Antibody 2E11 (SEQ ID NO:43):

```
gaagtgaagc tggtggaatc tgagggcggc ctgttgcagc
ctggcagcag catgaagctg agctgtaccg ccagcggctt
caagttcacc gactactaca tggcctgggt gcgacaggtg
cccgagaagg gactggaatg ggtggccaac atcaactacg
acggcagctc cacctactac ctggacagcc tgaagtccag
attcatcatc agcagagaca cgccaagaa catcctgtac
ctgcagatga actccctgaa gtctgaggac accgctacct
actactgcgc cagaaagggc tacttcgact actggggcca
gggcaccacc ctgacagtgt ctagcgccag cacaaagggc
cccagcgtgt tccctctggc cccttgtagc agaagcacca
gcgagtctac agccgccctg ggctgcctcg tgaaggacta
cttcccgag cccgtgaccg tgtcctggaa ctctggcgct
ctgacctctg gggtgcacac cttccctgcc gtgctgcagt
ctagcggcct gtactctctg agcagcgtcg tgacagtgcc
cagcagcagc ctgggcacca agacctacac ctgtaacgtg
gaccacaagc ccagcaacac caaggtggac aagagagtgg
aatctaagta cggccctccc tgcccccctt gtcctgctcc
tgaatttctg ggcggaccct ccgtgttcct gttccccca
aagcccaagg acaccctgat gatcagcaga acccccgaag
```

-continued

```
tgacctgcgt ggtggtggac gtgtcccagg aagatcccga ggtgcagttc aattggtacg tggacggcgt ggaagtgcac aacgctaaga ccaagcccag agaggaacag ttcaacagca cctacagagt ggtgtccgtg ctgacagtgc tgcatcagga ctggctgaac ggcaaagagt acaagtgcaa ggtgtccaac aagggcctgc ctagcagcat cgaaaagacc atcagcaagg ccaagggcca gccccgggaa ccccaggtgt acacactgcc tccaagccag gaagagatga ccaagaacca ggtgtccctg acctgtctcg tgaaaggctt ctacccctcc gatatcgccg tggaatggga gagcaacggc cagcccgaga acaactacaa gaccacccc cctgtgctgg actccgatgg ctcattcttc ctgtacagca gactgaccgt ggacaagtcc aggtggcagg aaggcaacgt gttcagctgc agcgtgatgc acgaggccct gcacaaccac tacacccaga agtccctgag cctgagcccc ggc
```

Amino Acid Sequence of the Heavy Chain of Anti-B7-H4 Antibody 2E11 (SEQ ID NO:44) [the sequence of the variable domain (SEQ ID NO:6) is shown underlined]:

EVKLVESEGG LVQPGSSMKL SCTASGFKFT DYYMAWVRQV

PEKGLEWVAN INYDGSSTYY LDSLKSRFII SRDNAKNILY

LQMNSLKSED TATYYCARKG YFDYWGQGTT LTVSSASTKG

PSVFPLAPCS RSTSESTAAL GCLVKDYFPE PVTVSWNSGA

LTSGVHTFPA VLQSSGLYSL SSVVTVPSSS LGTKTYTCNV

DHKPSNTKVD KRVESKYGPP CPPCPAPEFL GGPSVFLFPP

KPKDTLMISR TPEVTCVVVD VSQEDPEVQF NWYVDGVEVH

NAKTKPREEQ FNSTYRVVSV LTVLHQDWLN GKEYKCKVSN

KGLPSSIEKT ISKAKGQPRE PQVYTLPPSQ EEMTKNQVSL

TCLVKGFYPS DIAVEWESNG QPENNYKTTP PVLDSDGSFF

LYSRLTVDKS RWQEGNVFSC SVMHEALHNH YTQKSLSLSP

G

The light and heavy chains were expressed from the above-described 2D1-, 2H9- and 2E11-encoding polynucleotides by fusing to such polynucleotides a 5' start codon (ATG)-containing Leader Sequence and a 3' stop codon (TAG for the heavy chain-encoding polynucleotides and TAA for the light chain 2D1- and 2H9-encoding polynucleotides; TGA for the heavy and light chain 2E11-encoding polynucleotide). The polynucleotide encoding the leader sequence used for the expression of the 2D1 and 2H9 heavy and light chains was (SEQ ID NO:45):

```
atggagaccg acaccctgct gctctgggtg ctgctgctct
gggtgcccgg ctccaccgga
``` which encodes the Leader Sequence (SEQ ID NO:46): METDTLLLWV LLLWVPGSTG.

The polynucleotide encoding the leader sequence used for the expression of the 2E11 light chain was (SEQ ID NO:47):

```
atgagcgtgc ccacacaggt gctgggactg ctgctgctgt
ggctgaccga cgccagatgc
``` which encodes the Leader Sequence (SEQ ID NO:48): MSVPTQVLGL LLLWLTDARC.

The polynucleotide encoding the leader sequence used for the expression of the 2E11 heavy chain was (SEQ ID NO:49):

```
atggaatggt cctgggtgtt cctgttcttc ctgagcgtga
ccaccggcgt gcacagc
``` which encodes the Leader Sequence (SEQ ID NO:50): MEWSWVFLFF LSVTTGVHS.

Plasmids containing the 2D1- and 2H9-encoding polynucleotides were transfected into CHO cells with LAFECTINE™ cationic lipid-based transfection reagent (LakePharma). Supernatants were collected 4 days after transfection, and the total IgG level in supernatants was determined using Fc ELISA™ (LakePharma) (Table 4). As shown in Table 5, all of the tested heavy chain and light chain combinations resulted in the production of antibody. The background of the ELISA is less than 1 ng/ml.

TABLE 4

| Heavy Chain | Light Chain | IgG Produced (ng/ml) |
|---|---|---|
| 2D1 | 2D1 | 448 |
| 2D1 | 2H9 | 30 |
| 2H9 | 2D1 | 372 |
| 2H9 | 2H9 | 268 |

Human B7-H4 protein antigen and control antigen were coated onto 96-well ELISA plates. The plates are then blocked with 3% BSA, and washed in PBS.

The conditioned media (4 days post transfection) were then tested for antigen binding in the 96-well ELISA. Anti-Fc-HRP was used as the detecting antibody. Plates were washed with PBS, and TMB (3,3',5,5'-tetramethylbenzidine) was added for HRP color reaction. Once color developed, the $OD_{650}$ in each well was determined on an absorbance microplate reader. As shown in Table 5, antibodies formed from the 2D1 heavy and light chains or from the 2H9 heavy and light chains exhibited strong binding towards B7-H4 antigen and failed to show significant binding towards control. Antibody composed of one 2D1 chain and one 2H9 chain failed to show significant binding.

TABLE 5

| Heavy Chain | Light Chain | IgG Produced (ng/ml) |
|---|---|---|
| 2D1 | 2D1 | 1.12 |
| 2D1 | 2H9 | 0.06 |
| 2H9 | 2D1 | 0.02 |
| 2H9 | 2H9 | 1.15 |

Figure 6:
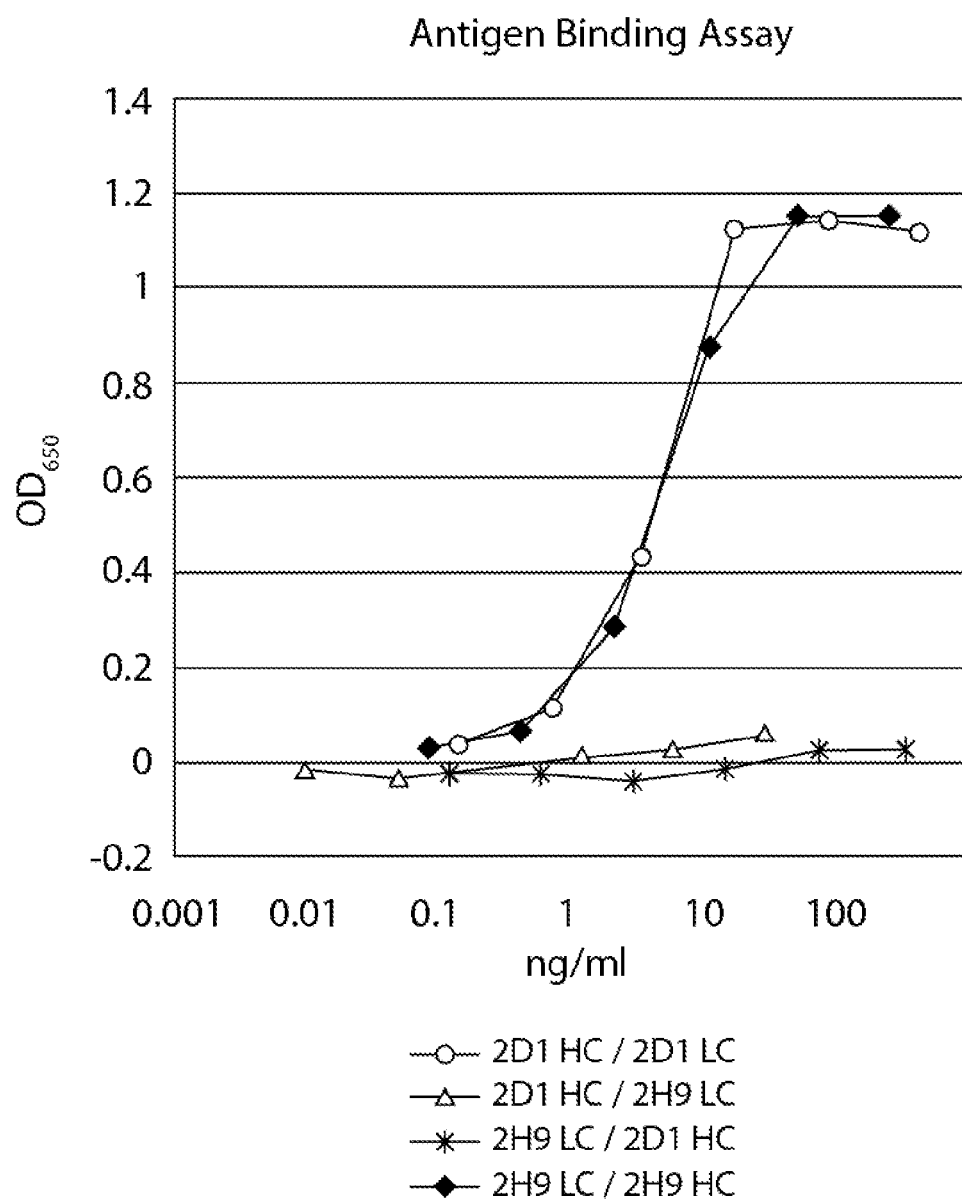
FIG. 6 shows the dose response capability of antibodies to bind to human B7-H4 antigen. The antibodies were produced through the recombinant expression of polynucleotides having the sequences of SEQ ID NO:33 (encoding the light chain of anti-B7-H4 antibody 2D1), SEQ ID NO:35, (encoding the heavy chain of anti-B7-H4 antibody 2D1), SEQ ID NO:37 (encoding the light chain of anti-B7-H4 antibody 2H9) and SEQ ID NO:39 (encoding the heavy chain of anti-B7-H4 antibody 2H9 (HC, Heavy Chain; LC, Light Chain).

In order to determine the potency of each antibody, the antigen binding assay was conducted using various concentrations of antibodies. FIG. 6 shows the dose response of the antibodies in binding target antigen.

The data indicate that polynucleotides having the sequence of SEQ ID NO:33 and SEQ ID NO:35 (light and heavy chain of anti-B7-H4 antibody 2D1, respectively) could be expressed and formed antibodies that were able to strongly and immunospecifically bind to human B7-H4 antigen. Likewise, the data indicate that polynucleotides having the sequence of SEQ ID NO:37 and SEQ ID NO:39 (light and heavy chain of anti-B7-H4 antibody 2H9, respectively) could be expressed, and formed antibodies that were able to strongly and immunospecifically bind to human B7-H4 antigen.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An antibody or an antigen-binding fragment thereof that specifically binds to human B7-H4, wherein the antibody or an antigen binding fragment thereof comprises a light chain variable region comprising the amino acid sequence of SEQ ID NO: 7; a heavy chain variable region comprising the amino acid sequence of SEQ ID NO: 8, or the combination thereof.

2. The antibody or an antigen binding fragment thereof of claim 1, wherein the antibody or antigen binding fragment thereof specifically binds to:
   (I) human B7-H4 arrayed on the surface of a cell;
   (II) human B7-H4 arrayed on the surface of a live cell at an endogenous concentration;
   (III) human B7-H4 arrayed on the surface of a live cell, and blocks binding between B7-H4 and its cellular receptor;
   (IV) human B7-H4 arrayed on the surface of a live cell, and inhibits immune suppression by binding to B7-H4 expressed on tumor-associated macrophages;
   (V) human B7-H4 arrayed on the surface of a live cell, and decreases the activity of a B7-H4-expressing tumor-associated macrophage in suppressing an immune response against tumor cells;
   (VI) human B7-H4 arrayed on the surface of a live tumor cell and inhibits suppression of an immune response by tumor cells expressing B7-H4; or
   (VII) human B7-H4 arrayed on the surface of a live tumor cell and causes tumor-specific cell lysis.

3. The antibody or an antigen binding fragment thereof of claim 1, wherein the antibody or an antigen binding fragment thereof is detectably labeled or comprises a conjugated toxin, drug, receptor, enzyme, receptor ligand.

4. The antibody or an antigen binding fragment thereof of claim 2, wherein said antibody or an antigen binding fragment thereof is capable of being internalized into said cell and of mediating the death of said cell.

5. The antibody or an antigen binding fragment thereof of claim 4, wherein said cell is a tumor cell, a pathogen-infected cell or a macrophage.

6. The antibody or an antigen binding fragment thereof of claim 1, which is
   a monoclonal antibody, a chimeric antibody, a humanized antibody, or an antigen binding fragment thereof.

7. The antibody or an antigen binding fragment thereof of claim 6, wherein said antibody or an antigen binding fragment thereof has ADCC activity and is capable of direct tumor killing activity, and/or is capable of inhibiting tumor-associated macrophage (TAM)-suppression of an immune response against a tumor or suppression of an immune response by tumor cells expressing B7-H4.

8. The antibody or an antigen binding fragment thereof of claim 6, wherein said antibody or an antigen binding fragment thereof is a bispecific or multispecific antibody that is capable of binding B7-H4 and a different molecule on the same cell.

9. A pharmaceutical composition for the treatment of cancer or infectious disease, comprising a therapeutically effective amount of the molecule of claim 1, and a physiologically acceptable carrier or excipient, wherein said molecule antagonizes a B7-H4-mediated suppression to up-modulate an immune response.

10. A method for the treatment of cancer or infectious disease in a subject exhibiting a symptom of said cancer or infectious disease or for the inhibition of cancer or infectious disease in a subject in advance of the exhibition of said symptom, comprising administering an effective amount of the pharmaceutical composition of claim 9.

11. The pharmaceutical composition of claim 9, wherein said composition is effective for the treatment of a chronic viral disease.

12. The antibody or an antigen binding fragment thereof of claim 1, wherein the light chain variable region comprises a complementarity determining region 1 (CDR1) comprising amino acids 24-38 of SEQ ID NO: 7; a CDR2 comprising amino acids 54-60 of SEQ ID NO: 7; and a CDR3 comprising amino acids 93-100 of SEQ ID NO: 7.

13. The antibody or an antigen binding fragment thereof of claim 1, wherein the heavy chain variable region comprises a CDR1 comprising amino acids 26-35 of SEQ ID NO: 8; a CDR2 comprising amino acids 50-66 of SEQ ID NO: 8; and a CDR3 comprising amino acids 99-107 of SEQ ID NO: 8.

14. The antibody or an antigen binding fragment thereof of claim 1, comprising a light chain comprising the amino acid sequence of SEQ ID NO: 38, a heavy chain comprising the amino acid sequence of SEQ ID NO: 40, or the combination thereof.

15. The antibody or an antigen binding fragment thereof of claim 6, which is a bispecific or a multispecific antibody.

16. An antibody or an antigen-binding fragment thereof that specifically binds to human B7-H4, wherein the antibody or an antigen binding fragment thereof comprises a light chain variable region comprising the amino acid sequence of SEQ ID NO: 3; a heavy chain variable region comprising the amino acid sequence of SEQ ID NO: 4; or the combination thereof.

17. The antibody or an antigen binding fragment thereof of claim 16, wherein the light chain variable region comprises a CDR1 comprising amino acids 24-39 of SEQ ID NO: 3; a CDR2comprising amino acids 55-61 of SEQ ID NO: 3; and a CDR3 comprising amino acids 94-102 of SEQ ID NO: 3; and the heavy chain variable region comprises a CDR1 comprising amino acids 26-35 of SEQ ID NO: 4; a CDR2 comprising amino acids 50-66 of SEQ ID NO: 4; and a CDR3comprising amino acids 99-105 of SEQ ID NO: 4.

18. The antibody or an antigen binding fragment thereof of claim 16, comprising a light chain comprising the amino acid sequence of SEQ ID NO: 34, a heavy chain comprising the amino acid sequence of SEQ ID NO: 36, or the combination thereof.

19. An antibody or an antigen-binding fragment thereof that specifically binds to human B7-H4, wherein the antibody or an antigen binding fragment thereof comprises a light chain variable region comprising the amino acid sequence of SEQ ID NO: 5; a heavy chain variable region comprising the amino acid sequence of SEQ ID NO: 6; or the combination thereof.

20. The antibody or an antigen binding fragment thereof of claim 19, wherein the light chain variable region comprises a CDR1 comprising amino acids 24-40 of SEQ ID NO: 5; a CDR2comprising amino acids 56-62 of SEQ ID NO: 5; and a CDR3 comprising amino acids 95-103 of SEQ ID NO: 5; and the heavy chain variable region comprises a CDR1 comprising amino acids 26-35 of SEQ ID NO: 6; a CDR2 comprising amino acids 50-66 of SEQ ID NO: 6; and a CDR3comprising amino acids 99-104 of SEQ ID NO: 6.

21. The antibody or an antigen binding fragment thereof of claim 19, comprising a light chain comprising the amino acid sequence of SEQ ID NO: 42, a heavy chain comprising the amino acid sequence of SEQ ID NO: 44, or the combination thereof.

22. The antibody or an antigen binding fragment thereof of claim 6, wherein said antibody or an antigen binding fragment thereof is an IgG1 antibody-or an antigen binding fragment thereof.

23. The antibody or an antigen binding fragment thereof of claim 6, wherein said antibody or an antigen binding fragment thereof is capable of inhibiting tumor-associated macrophage (TAM)-suppression of an immune response against a tumor.

24. The antibody or an antigen binding fragment thereof of claim 6, wherein said antibody or an antigen binding fragment thereof is capable of inhibiting suppression of an immune response by tumor cells expressing B7-H4.

* * * * *